US006620806B2

(12) United States Patent
Day et al.

(10) Patent No.: US 6,620,806 B2
(45) Date of Patent: Sep. 16, 2003

(54) METHODS AND KITS FOR IMPROVING VASCULAR HEALTH

(75) Inventors: Wesley W. Day, San Diego, CA (US); Andrew G. Lee, Old Lyme, CT (US); David D. Thompson, Gales Ferry, CT (US)

(73) Assignee: Pfizer Inc., New York, NY (US)

( * ) Notice: Subject to any disclaimer, the term of this patent is extended or adjusted under 35 U.S.C. 154(b) by 19 days.

(21) Appl. No.: 09/977,458

(22) Filed: Oct. 15, 2001

(65) Prior Publication Data

US 2002/0156090 A1 Oct. 24, 2002

Related U.S. Application Data

(60) Provisional application No. 60/241,532, filed on Oct. 17, 2000.

(51) Int. Cl.$^7$ .............................................. A61K 31/55
(52) U.S. Cl. ............. 514/217.03; 514/212; 514/217.08; 514/315; 514/317; 514/323; 514/307; 514/345; 514/428; 514/213; 514/582; 514/585; 514/648; 514/331; 514/414; 514/415
(58) Field of Search ................................. 514/428, 320, 514/305, 212, 323, 414, 415, 217.03, 217.08, 648, 317, 307, 315, 331, 345, 213, 482, 582, 585

(56) References Cited

U.S. PATENT DOCUMENTS

| | | | |
|---|---|---|---|
| 5,552,412 A | 9/1996 | Cameron et al. | |
| 5,595,722 A | 1/1997 | Grainger et al. | |
| 5,770,609 A | 6/1998 | Grianger et al. | |
| 5,789,400 A | 8/1998 | Cullinan et al. | |
| 5,889,042 A | 3/1999 | MacLean et al. | |
| 5,948,809 A | 9/1999 | Chiu et al. | |
| 5,968,918 A | 10/1999 | Kanda | |
| 5,990,129 A | 11/1999 | Bryant et al. | |
| 6,034,102 A | 3/2000 | Aiello | |
| 6,107,331 A | 8/2000 | MacLean et al. | |
| 6,153,622 A | 11/2000 | Cameron et al. | |
| 6,204,284 B1 | 3/2001 | Beer et al. | |
| 6,274,618 B1 | 8/2001 | MacLean et al. | |
| 2001/0056099 A1 * | 12/2001 | Day et al. ................... | 514/307 |

FOREIGN PATENT DOCUMENTS

| | | |
|---|---|---|
| WO | WO9746233 | 12/1997 |
| WO | WO9809619 | 3/1998 |
| WO | WO9909007 | 2/1999 |
| WO | WO 9947149 | 9/1999 |

OTHER PUBLICATIONS

Willson, T. M., et al., 3–[4–(1,2–Diphenylbut– 1–enyl)phenyl]acryclic acid: A non–steroidal estrogen with functional selectivity for bone over uterus in rats; *J. Med. Chem.*, (1994), vol. 37, p. 1550–1552.

DeValke–de Roo, G. W., et al., Both Raloxifene and Estrogen Reduce Major Cardiovascular Risk Factors in Healthy Postmenopausal Women; *Arterioscler. Thromb. Vasc. Biol.*, Dec. 1999, p. 2993–2994.

Nishino, M., et al., Lack of Association of Lipoprotein(a) Levels with Coronary Calcium Deposits in Asymptomatic Postmenopausal Women; *Journal of the American College of Cardiology*, vol. 35, No. 2, p. 314–320, (2000).

Nuti, R., et al., The Role of Calcitriol in the Treatment of Osteroporosis; *Calcified Tissue International*, (2000), vol. 66, p. 239–240.

Shlipak, M., et al., Estrogen and Progestin, Lipoprotein(a), and the Risk of Recurrent Coronary Heart Disease Events after Menopause; *JAMA*, vol. 283, No. 14, p. 1845–1852. Apr. 12, 2000.

Ridker, P.M., et al, C–reactive Protein and Other Markers of Inflammation in the Prediction of Cardiovascular Disease in Women; *The New England Journal of Medicine*, vol. 342, No. 12, p. 836–843, Mar. 23, 2000.

Gotto, A. M., et al, Relation Between Baseline and On–treatment Lipid Parameters and First Acute Major Coronary Events in the Air Force/Texas Coronary Atherosclerosis Prevention Study (AFCAPS/TexCAPS); *Circulation*, p. 477–484, Feb. 8, 2000.

Goldstein, S. R., A Pharmacological Review of Selective Oestrogen Receptor Modulators; *Human Reproduction Update*, vol. 6, No. 3, p. 212–224; (2000).

St. Clair, R. W. Estrogens and Atherosclerosis: Phytoestrogens and selective estrogen receptor modulators, *Current Opinion of Lipidology*, vol. 9, p. 457–463, (1998).

Goldfrank, D., et al., Raloxifene, a New Selective Estrogen Receptor Modulator, *J. Clin. Pharacol.*, vol. 39, p. 767–774, (1999).

Wilson, T. M., et al., Dissection of the Molecular Mechanism of Action of GW5638, a Novel Estrogen Receptor Ligand, Provides Insights into the Role of Estrogen Receptor in Bone; *Endocrinology*, vol. 138, No. 9, p. 3901–3911; (1997).

Walsh, B. W., The Effects of Hormone Replacement Therapy and Raloxifene on C–Reactive Protein and Homocysteine in Healthy Postmenopausal Women: A Randomized, Controlled Trial; *The Journal of Clinical Endocrinology and Metabolism*, vol. 85, No. 1, p. 214–.

Walsh, B. W., et al., Effects of Raloxifene on Serum Lipids and Coagulation Factors in Healthy Post Menopausal Women; *JAMA*, vol. 279, No. 18, p. 1445–, May 13, 1998.

Non–provisional U.S. patent application No. 09/365,540.
Non–provisional U.S. patent application No. 09/767,625.
Non–provisional U.S. patent application No. 09/757,817.
Non–provisional U.S. patent application No. 09/628,084.
Provisional U.S. patent application No. 60/250,071.

* cited by examiner

Primary Examiner—James H. Reamer
(74) Attorney, Agent, or Firm—Peter C. Richardson; Gregg C. Benson; Todd M. Crissey

(57) ABSTRACT

The present invention provides methods and kits for improving or maintaining vascular health, including preventing myocardial infarction or stroke; maintaining or improving vascular reactivity; treating acute or chronic renal failure, peripheral arterial occlusive disease, coronary artery disease, or Raynaud's phenomenon; or lowering plasma levels of Lp(a) using an estrogen agonist/antagonist.

27 Claims, No Drawings

METHODS AND KITS FOR IMPROVING VASCULAR HEALTH

CROSS-REFERENCE TO RELATED APPLICATION

This application claims priority of U.S. provisional application No. 60/241,532, filed Oct. 17, 2000.

FIELD OF THE INVENTION

This invention relates to methods and kits for improving vascular health, including preventing myocardial infarction or stroke; maintaining or improving vascular reactivity; treating acute or chronic renal failure, peripheral arterial occlusive disease, coronary artery disease, or Raynaud's phenomenon; or lowering plasma levels of Lp(a) using an estrogen agonist/antagonist.

BACKGROUND OF THE INVENTION

The hormone estrogen has a profound effect in the vascular system of both male and female subjects, although its administration is associated with other effects that can be undesirable. Estrogen increases vasodilatation and inhibits the response of blood vessels to injury and the development of atherosclerosis. Estrogen-induced vasodilatation occurs 5 to 20 minutes after estrogen has been administered and is not dependent on changes in gene expression; this action of estrogen is sometimes referred to as "nongenomic." The estrogen-induced inhibition of the response to vascular injury and the preventive effect of estrogen against atherosclerosis occur over a period of hours or days after estrogen treatment and are dependent on changes in gene expression in the vascular tissues; these actions are sometimes referred to as "genomic."

In premenopausal women, 17β-estradiol produced by the ovaries is the chief circulating estrogen. Serum estradiol concentrations are low in preadolescent girls and increase at menarche. In women, they range from about 100 pg per milliliter (367 pmol per liter) in the follicular phase to about 600 pg per milliliter (2200 pmol per liter) at the time of ovulation. They may rise to nearly 20,000 pg per milliliter (70,000 pmol per liter) during pregnancy. After menopause, serum estradiol concentrations fall to values similar to or lower than those in men of similar age (5 to 20 pg per milliliter [18 to 74 pmol per liter]) (Yen, S. S. C. and Jaffe, R. B., eds. *Reproductive Endocrinology: Physiology, Pathophysiology and Clinical Management*, 3rd ed. Philadelphia: W. B. Saunders, (1991)).

The ovaries are the principle source of estrogen in premenopausal women. The major secretory product is estradiol, synthesized by granulosa cells from androgenic precursors provided by thecal cells. Secreted estradiol is oxidized reversibly to estrone, and both of these estrogens can be converted to estriol. These transformations take place mainly in the liver, where interconversion between estrone and estradiol is catalyzed by 17-hydroxysteroid dehydrogenase.

In men and postmenopausal women, the principle source of estrogen is adipose tissue. In this and in other peripheral tissues, estrone is synthesized from dehydroepiandrosterone, which is secreted by the adrenal cortex. Thus, the contribution of adipose tissue estrogens is regulated, in part by the availability of androgenic precursors (Mendelson, C.R. and Simpson, E.R., *Mol. Cell Endocrinol.*, 52:169–176, (1987)).

There are two estrogen receptors, estrogen receptor a and estrogen receptor β, both of which are members of the superfamily of steroid hormone receptors. (Walter, P., et al., *Proc Nad Acad Sci USA* 1985;82:7889–93; Kuiper, G. G. J. M., et al; *Proc NadAcad Sci USA* 1996;93:5925–30) Estrogen receptors α and β have considerable homology and, like all steroid hormone receptors, are transcription factors that alter gene expression when they are activated. (Walter, P., et al. *Proc Nad Acad Sci USA* 1985;82:7889–93; Kuiper, G. G. J. M., et al.; *Proc Nad Acad Sci USA* 1996;93:5925–30; Shibata, H., et al. *Recent Prog Horm Res* 1997;52:141–65; Evans, R. M., *Science* 1988;240:889–95; Brown, M., *Hematol Oncol Clin North Am* 1994;8:101–12). Blood vessels are complex structures, with walls containing smooth-muscle cells and an endothelial cell lining. Vascular endothelial and smooth muscle cells bind estrogen with high affinity (Mendelsohn, M. E., et al., *Curr Opin Cardiol* 1994;9:619–26; Farhat, M. Y., et al., *FASEB J* 1996;10:615–24) and estrogen receptor α has been identified in both types of vascular cells in women and men, (Karas, R. H., et al., *Circulation* 1994;89:1943–50; Losordo, D. W., et al., *Circulation* 1994;89:1501–10; Venkov, C. D., et al., *Circulation* 1996;94:727–33; Kim-Schulze, S., et al., *Circulation* 1996;94:1402–7; Caulin-Glaser, T., et al., *J Clin Invest* 1996;98:36–42) as well as in myocardial cells (Grohe, C., et al., *FEBS Lett* 1997;416:107–12).

Estrogen receptor α activates specific target genes in vascular smooth-muscle and endothelial cells (Table 1) (Karas, R. H., et al., *Circulation* 1994;89:1943–50, Venkov, C. D., et al., *Circulation* 1996;94:727–33; Kim-Schulze, S., et al, *Circulation* 1996;94:1402–7; Caulin-Glaser, T., et al., *J Clin Invest* 1996;98:36–42; Koike, H., etal., *J Vasc Surg* 1996;23:477–82). Estrogen receptor β is structurally and functionally distinct from estrogen receptor α. Functional estrogen receptor β is also present in myocardial cells, in which it regulates the expression of nitric oxide synthases.

Estrogen alters serum lipid concentrations, coagulation and fibrinolytic systems, antioxidant systems, and the production of other vasoactive molecules, such as nitric oxide and prostaglandins, all of which can influence the development of vascular disease.

The effects of estrogen therapy on serum lipid concentrations result largely from estrogen-receptor-mediated effects on the hepatic expression of apoprotein genes (Table 1). Many studies, including one large, randomized, controlled trial (The Writing Group for the PEPI Trial, *JAMA* 1995;273:199–208. [Erratum, *JAMA* 1995;274:1676.]) have documented that estrogen therapy in post-menopausal women decreases serum total cholesterol and low density lipoprotein (LDL) cholesterol concentrations, increases serum high-density lipoprotein (HDL) cholesterol and triglyceride concentrations, and decreases serum Lp(a) lipoprotein concentrations. Increased Lp(a) levels have been associated with increased risk of recurrent coronary heart disease events after menopause (Shlipak, M. G., et al., *JAMA* 2000;283: 1845–1852). Hepatic expression of the genes for several coagulation and fibrinolytic proteins is also regulated by estrogen through estrogen receptors (Table 1).

Estrogen directly regulates vasomotor tone through both short-term and long-term effects on the vasculature. Long-term administration of estrogen is associated with decreased plasma concentrations of renin (Schunkert, H., et al., *Circulation* 1997;95:39–45), angiotensin-converting enzyme (Proudler, A., et al., *Lancet* 1995;346:89–90) and endothelin-1 (Ylikorkala, O., et al., J Clin Endocrinol Metab 1995;80:3384–7) and decreased vascular expression of the gene for angiotensin II receptor type 1 (Nickenig, G., et al., *Circulation* 1998;97:2197–201) as well as an increased ratio of nitric oxide to endothelin-1 in plasma (Best, P. J. M., et al., *Ann Intern Med* 1998;128:285–8). The net effect of these changes is to promote vasodilatation.

Estrogens can cause short-term vasodilatation by both endothelium-dependent and endothelium-independent pathways. These rapid effects do not appear to involve changes in gene expression. Two mechanisms for the rapid vasodilatory effects of estrogens have been explored in some depth: effects on ion-channel function and effects on nitric oxide. At physiologic concentrations, estrogen stimulates the opening of calcium-activated potassium channels through a nitric oxide- and cyclic guanosine monophosphate-dependent pathway (White, R. E., et al., *Circ Res* 1995;77:936–42; Wellman, G. C., et al., *Circ Res* 1996;79:1024–30) thus relaxing smooth muscle and promoting vasodilatation. These rapid effects of estrogen on vascular cells could be mediated by a known estrogen receptor, perhaps located in the plasma membrane (Pappas, T. C., et al., *FASEB J* 1995;9:404–10) that is able to activate nitric oxide synthase rapidly in a nongenomic manner. This suggestion is consistent with the observations that estrogen-induced stimulation of nitric oxide synthase activity in endothelial cells is blocked by specific estrogen-receptor antagonists (Chen, Z., et al., *J Clin Invest* 1999;103:401–6; Lantin-Hermoso, R. L., *Am J Physiol* 1997;273: L119–L126; Caulin-Glaser, T., et al., Circ Res 1997;81:885–92) and that estrogen receptor α can directly activate endothelial nitric oxide synthase.

Estrogen rapidly causes coronary vasodilatation ex vivo (Mendelsohn, M. E., et al., *Curr Opin Cardiol* 1994;9:619–26; Farhat, M. Y., et al., *FASEB J* 1996;10:615–24) and in vivo in cholesterol-fed ovariectomized primates (Williams, J. K., et al., *J Am Coll Cardiol* 1992;20:452–7) and other animals (Guetta, V., et al., *Circulation* 1997;96:2795–801). Estrogen dilates coronary and brachial arteries in post-menopausal women (Reis, S. E., et al., *Circulation* 1994;89:52–60; Gilligan, D. M., et al., *Circulation* 1994;89:2545–51; Gilligan, D. M., etal., *Circulation* 1994;90:786–91; Lieberman, E. H., etal., *Ann Intern Med* 1994;121:936–41; Collins, P., et al., *Circulation* 1995;92:24–30; Guetta, V, et al., *Circulation* 1997;96:2795–801) and, in some studies, in men (Collins, P., et al., *Circulation* 1995;92:24–30; Blumenthal, R.S., et al., *Am J Cardiol* 1997;80:1021–4; Reis, S. E., et al., *Circulation* 1998;97:23–5). Sublingual administration of 17β-estradiol in post-menopausal women increases the duration of treadmill exercise before the onset of ischemia (Rosano, G. M. C., etal., *Lancet* 1993;342:133–6).

Estrogen increases the expression of genes for important vasodilatory enzymes such as prostacyclin synthase and nitric oxide synthase (Table 1) (Weiner, C. P., et al., *Proc Natl Acad Sci USA* 1994;91;5212–6; Binko, J., et al., *Am J Physiol* 1998;274:H853–H859). Some of the rapid effects of estrogen may therefore be due to longer-term increases in the expression of the genes for these enzymes in vascular tissues. Estrogen may also increase the bioavailability of nitric oxide in vessels by increasing the expression of the gene for the inducible form of nitric oxide synthase (Binko, J., et al., *Am J Physiol* 1998;274:H853–H859). Long-term administration of estrogen increases acetylcholine-mediated coronary vasodilatation in nonhuman primates (Williams, J. K., et al., *Circulation* 1990;81:1680–7; Williams, J. K., et al, *Circulation* 1997;96:1970–5), male-to-female transsexuals (McCrohon, J. A., et al, *J Am Coll Cardiol* 1997;29:1432–6; New, G., et al, *J Am Coll Cardiol* 1997;29:1437–44), post-menopausal women (Herrington, D. M., et al, *Am J Cardiol* 1994;73: 951–2) and post-menopausal women with angina and normal coronary arteries (Roque, M., et al, *J Am Coll Cardiol* 1998;31 :139–43).

TABLE 1

ESTROGEN-REGULATED GENES OF POTENTIAL IMPORTANCE IN VASCULAR PHYSIOLOGY AND DISEASE.
(Source: Mendelsohn, M. E. and Karas, R. H., N Engl J Med, 1999; 340: 1801–11)

| GENE PRODUCT | PHYSIOLOGIC OR PATHO-PHYSIOLOGIC ROLE |
|---|---|
| Estrogen-regulated genes (vascular cells) | |
| Prostacyclin synthase | Vasodilatation |
| Endothelial nitric oxide synthase | Vasodilatation |
| Inducible nitric oxide synthase | Vasodilatation in response to vascular injury |
| Endothelin-1 | Vasoconstriction |
| Collagen | Vascular-matrix formation |
| Matrix metalloproteinase 2 | Vascular-matrix remodeling |
| E-selectin | Cell adhesion |
| Vascular-cell adhesion molecule | Cell adhesion |
| Vascular endothelial growth factor | Angiogenesis and endothelial-cell proliferation |
| Estrogen-regulated genes (nonvascular cells) | |
| Growth- and development-related genes | |
| Transforming growth factor $\beta_1$ | Wound healing |
| Epidermal growth factor receptor | Cell growth in response to vascular injury |
| Platelet-derived growth factor | Cell growth in response to vascular injury |
| flt-4 tyrosine kinase | Angiogenesis and endothelial-cell proliferation |
| Coagulation- and fibrinolysis-related genes | |
| Tissue factor | Hemostasis in response to thrombosis |
| Fibrinogen | Hemostasis in response to thrombosis |
| Protein S | Hemostasis in response to thrombosis |
| Coagulation factor VII | Hemostasis in response to thrombosis |
| Coagulation factor XII | Hemostasis in response to thrombosis |
| Plasminogen-activator inhibitor 1 | Hemostasis in response to thrombosis |
| Tissue plasminogen activator | Fibrinolysis |
| Antithrombin III | Anticoagulation |
| Signaling-related and miscellaneous genes | |
| Estrogen receptor α | Hormonal regulation and gene expression |
| Estrogen receptor β | Hormonal regulation and gene expression |
| Monocyte chemotactic protein 1 | Monocyte recruitment and atherosclerosis |
| I and HK2 (cardiac potassium channels) | Cardiac conduction |
| Connexin 43 | Cardiac conduction |
| Leptin | Fat metabolism and obesity |
| Apolipoproteins A, B, D, and E and Lp(a) | Lipid metabolism and atherosclerosis |
| Angiotensin-converting enzyme | Vasoconstriction |
| Angiotensin II receptor, type 1 | Vasoconstriction |

Estrogen accelerates endothelial cell growth in vitro and in vivo (Morales, D. E., et al., *Circulation* 1995;91:755–63; Krasinski, K., et al., *Circulation* 1997;95:1768–72). The rapid re-endothelialization induced by estrogen after vascular injury may be due in part to increased local expression of vascular endothelial growth factor. Estrogen also inhibits apoptosis of cultured human endothelial cells in an estrogen receptor-dependent manner (Spyridopoulos, I., et al., *Circulation* 1997;95:1505–14). Early restoration of endothelial integrity by estrogen may contribute to the attenuation of the response to injury by increasing the availability of nitric oxide, which can directly inhibit the proliferation of smooth-muscle cells (Cornwell, T. L., et al., *Am J Physiol*

1994;267:C1405–C1413). Estrogen directly inhibits the migration and proliferation of smooth-muscle cells in vitro (Kolodgic, F. D., et al., *Am J Pathol* 1996;148: 969–76; Bhalla, R. C., et a., *Am J Physiol* 1997;272:HI996–H2003).

Thus, estrogen has both rapid and longer-term effects on the blood-vessel wall. It is believed that estrogen influences the bioavailability of endothelial-derived nitric oxide and, through nitric oxide-mediated increases in cyclic guanosine monophosphate, causes the relaxation of vascular smooth-muscle cells. The longer-term effects of estrogen are due at least in part to changes in vascular-cell gene and protein expression that is mediated by estrogen receptor α, β, or both. Estrogen-regulated proteins influence vascular function in an autocrine or paracrine fashion.

The direct effects of estrogen on the vasculature promote vasodilatation and inhibit the development and progression of atherosclerosis. However, some of the nonvascular effects of estrogen may offset its beneficial vascular effects.

Breast cancer is a hormone-dependent disease. Women without functioning ovaries who never receive estrogen replacement do not develop breast cancer. The female-to-male ratio for the disease is about 150 to 1. A host of findings indicate that hormones play a critical role as promoters of the disease. For most epithelial malignancies, a log—log plot of incidence versus age shows a straight-line increase with every year of life. A similar plot for breast cancer shows the same straight line increase, but with a decrease in slope beginning at the age of menopause. The three dates in a woman's life that have a major impact on breast cancer incidence are age of menarche, age at first full-term pregnancy, and age of menopause. Women who experience menarche at age 16 have only 50 to 60 percent of the lifetime breast cancer risk of women who experience menarche at age 12. Similarly, menopause occurring 10 years before the median age (52 years), whether natural or surgically induced, reduces lifetime breast cancer risk by about 35 percent. Compared with nulliparous women, women who have a first full-term pregnancy by age 18 have 30 to 40 percent the risk of breast cancer. Thus, length of menstrual life—particularly the fraction occurring before the first full-term pregnancy—is a substantial component of the total risk of breast cancer. This factor can account for 70 to 80 percent of the variation in breast cancer frequency in different countries.

International variation has provided some of the most important clues on hormonal carcinogenesis. A woman living to age 80 in North America has 1 chance in 9 of developing invasive breast cancer. Asian women have one-fifth to one-tenth the risk of breast cancer of women in North America or Western Europe. Asian women have substantially lower concentrations of estrogens and progesterone. These differences cannot be explained on a genetic basis, because Asian women living in a Western environment have a risk identical to that of their Western counterparts. These women also differ markedly in height and weight from Asian women in Asia; height and weight are critical regulators of age of menarche and have substantial effects on plasma concentrations of estrogens. (Lippman, M. E., *Breast Cancer*, Chapter 91, in *Harrison's Principles of Internal Medicine*, 14th ed., 1998).

Menopause occurs naturally at an average age of 50 to 51 years in the USA. As ovaries age, response to pituitary gonadotropins (follicle-stimulating hormone [FSH] and luteinizing hormone [LH]) decreases, initially resulting in shorter follicular phases (thus, shorter menstrual cycles), fewer ovulations, decreased progesterone production, and more irregularity in cycles. Eventually, the follicle fails to respond and does not produce estrogen. The transitional phase, during which a woman passes out of the reproductive stage, begins before menopause. It is termed the climacteric or perimenopause, although many persons refer to it as menopause.

Premature menopause refers to ovarian failure of unknown cause that occurs before age 40. It may be associated with smoking, living at high altitude, or poor nutritional status. Artificial menopause may result from oophorectomy, chemotherapy, radiation of the pelvis, or any process that impairs ovarian blood supply.

Symptoms of the climacteric range from nonexistent to severe. Hot flushes (flashes) and sweating secondary to vasomotor instability affect 75% of women. Most have hot flushes for more than 1 year, and 25 to 50% for more than 5 years. The woman feels warm or hot and may perspire, sometimes profusely. The skin, especially of the head and neck, becomes red and warm. The flush, which may last from 30 seconds to 5 minutes, may be followed by chills. Vasomotor symptoms of the hot flush coincide with the onset of LH pulses, but not every increase in LH is associated with a hot flush, suggesting that hypothalamic control of LH pulses is independent of that of flushes. This independence is confirmed by the occurrence of hot flushes in women who have had pituitary failure and do not secrete LH and/or FSH.

Psychologic and emotional symptoms—including fatigue, irritability, insomnia, inability to concentrate, depression, memory loss, headache, anxiety, and nervousness and timidity can occur. Sleep disruption by recurrent hot flushes contributes to fatigue and irritability. Intermittent dizziness, paresthesias, palpitations, and tachycardia may also occur. Nausea, constipation, diarrhea, arthralgia, myalgia, cold hands and feet, and weight gain are also common.

The large reduction in estrogen leads to profound changes in the lower genital tract; e.g., the vaginal mucosa and vulvar skin become thinner, the normal bacterial flora changes, and the labia minora, clitoris, uterus, and ovaries decrease in size. Inflammation of the vaginal mucosa (atrophic vaginitis) can cause the mucosa to have a strawberry appearance and can lead to urinary frequency and urgency, vaginal dryness, and dyspareunia. Women tend to lose pelvic muscle tone and to develop urinary incontinence, cystitis, and vaginitis.

SUMMARY OF THE INVENTION

The present invention provides methods of preventing myocardial infarction or stroke; maintaining or improving vascular reactivity; or treating acute or chronic renal failure, peripheral arterial occlusive disease, coronary artery disease, or Raynaud's phenomenon, the methods comprising administering to a patient at risk of having a myocardial infarction or a stroke; in need of maintenance or improvement of vascular reactivity; or having acute or chronic renal failure, peripheral arterial occlusive disease, coronary artery disease, or Raynaud's phenomenon, a therapeutically effective amount of an estrogen agonist/antagonist.

In a preferred embodiment of the methods, the estrogen agonist/antagonist is a compound of formula (I):

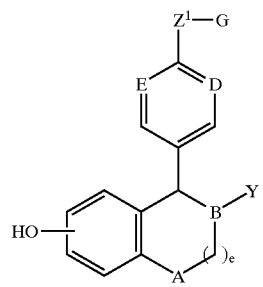

(I)

wherein:
A is selected from CH$_2$ and NR;
B, D and E are independently selected from CH and N;
Y is
(a) phenyl, optionally substituted with 1–3 substituents independently selected from R$^4$;
(b) naphthyl, optionally substituted with 1–3 substituents independently selected from R$^4$;
(c) C$_3$–C$_8$ cycloalkyl, optionally substituted with 1–2 substituents independently selected from R$^4$;
(d) C$_3$–C$_8$ cycloalkenyl, optionally substituted with 1–2 substituents independently selected from R$^4$;
(e) a five membered heterocycle containing up to two heteroatoms selected from the group consisting of —O—, —NR$^2$— and —S(O)$_n$—, optionally substituted with 1–3 substituents independently selected from R$^4$;
(f) a six membered heterocycle containing up to two heteroatoms selected from the group consisting of —O—, —NR$^2$— and —S(O)$_n$— optionally substituted with 1–3 substituents independently selected from R$^4$; or
(g) a bicyclic ring system consisting of a five or six membered heterocyclic ring fused to a phenyl ring, said heterocyclic ring containing up to two heteroatoms selected from the group consisting of —O—, —NR$^2$— and —S(O)$_n$—, optionally substituted with 1–3 substituents independently selected from R$^4$;
Z$^1$ is
(a) —(CH$_2$)$_p$W(CH$_2$)$_q$—;
(b) —O(CH$_2$)$_p$CR$^5$R$^6$—;
(c) —O(CH$_2$)$_p$W(CH$_2$)$_q$—;
(d) —OCHR$^2$CHR$^3$—; or
(e) —SCHR$^2$CHR$^3$—;
G is
(a) —NR$^7$R$^8$;
(b)

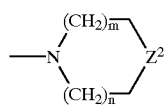

wherein n is 0, 1 or 2; m is 1, 2 or 3; Z$^2$ is —NH—, —O—, —S—, or —CH$_2$—; optionally fused on adjacent carbon atoms with one or two phenyl rings and, optionally independently substituted on carbon with one to three substituents and, optionally, independently on nitrogen with a chemically suitable substituent selected from R$^4$; or
(c) a bicyclic amine containing five to twelve carbon atoms, either bridged or fused and optionally substituted with 1–3 substituents independently selected from R$^4$; or Z$^1$ and G in combination may be

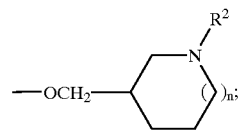

W is
(a) —CH$_2$—;
(b) —CH=CH—;
(c) —O—;
(d) —NR$^2$—;
(e) —S(O)$_n$—;
(f)

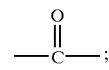

(g) —CR$^2$(OH)—;
(h) —CONR$^2$—;
(i) —NR$^2$CO—;
(j)

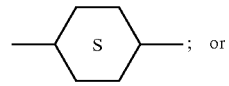 ; or (k) —C≡C—;
R is hydrogen or C$_1$–C$_6$ alkyl;
R$^2$ and R$^3$ are independently
(a) hydrogen; or
(b) C$_1$–C$_4$ alkyl;
R$^4$ is
(a) hydrogen;
(b) halogen;
(c) C$_1$–C6 alkyl;
(d) C$_1$–C$_4$ alkoxy;
(e) C$_1$–C$_4$ acyloxy;
(f) C$_1$–C$_4$ alkylthio;
(g) C$_1$–C$_4$ alkylsulfinyl;
(h) C$_1$–C$_4$ alkylsulfonyl;
(i) hydroxy (C$_1$–C$_4$)alkyl;
(j) aryl (C$_1$–C$_4$)alkyl;
(k) —CO$_2$H;
(l) —CN;
(m) —CONHOR;
(n) —SO$_2$NHR;
(o) —NH$_2$;
(p) C$_1$–C$_4$ alkylamino;
(q) C$_1$–C$_4$ dialkylamino;
(r) —NHSO$_2$R;
(s) —NO$_2$;
(t) -aryl; or
(u) —OH;
R$^5$ and R$^6$ are independently C$_1$–C$_8$ alkyl or together form a C$_3$–C$_{10}$ carbocyclic ring;
R$^7$ and R$^8$ are independently
(a) phenyl;

(b) a $C_3$–$C_{10}$ carbocyclic ring, saturated or unsaturated;

(c) a $C_3$–$C_{10}$ heterocyclic ring containing up to two heteroatoms, selected from —O—, —N— and —S—;

(d) H;

(e) $C_1$–$C_6$ alkyl; or (f) form a 3 to 8 membered nitrogen containing ring with $R^5$ or $R^6$;

$R^7$ and $R^8$ in either linear or ring form may optionally be substituted with up to three substituents independently selected from $C_1$–$C_6$ alkyl, halogen, alkoxy, hydroxy and carboxy;

a ring formed by $R^7$ and $R^8$ may be optionally fused to a phenyl ring;

e is 0, 1 or 2;

m is 1, 2 or 3;

n is 0, 1 or 2;

p is 0, 1, 2 or 3;

q is 0, 1, 2 or 3;

or an optical or geometric isomer thereof; or a pharmaceutically acceptable salt, N-oxide, ester, quaternary ammonium salt or prodrug thereof.

In another preferred embodiment of the methods, the estrogen agonist/antagonist is a compound of formula (IA)

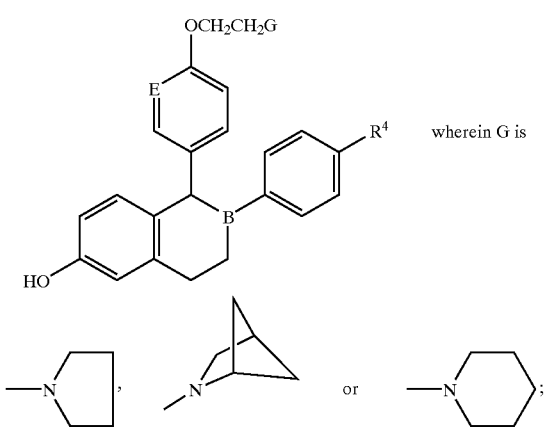

(IA)

wherein G is $R^4$ is H, OH, F, or Cl; and B and E are independently selected from CH and N or an optical or geometric isomer thereof; or a pharmaceutically acceptable salt, N-oxide, ester, quaternary ammonium salt, or a prodrug thereof.

In another preferred embodiment of the methods, the estrogen agonist/antagonist is (–)-cis-6-phenyl-5-[4-(2-pyrrolidin-1-yl-ethoxy)-phenyl]-5,6,7,8-tetrahydro-naphthalene-2-ol or an optical or geometric isomer thereof; a pharmaceutically acceptable salt, N-oxide, ester, quaternary ammonium salt, or a prodrug thereof.

In another preferred embodiment of the methods, the estrogen agonist/antagonist is (–)-cis-6-phenyl-5-[4-(2-pyrrolidin-1-yl-ethoxy)-phenyl]-5,6,7,8-tetrahydro-naphthalene-2-ol, D-tartrate salt.

In another preferred embodiment of the methods, the estrogen agonist/antagonist is a compound selected from the formulas V or VI:

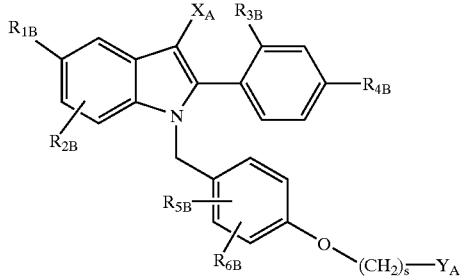

(V)

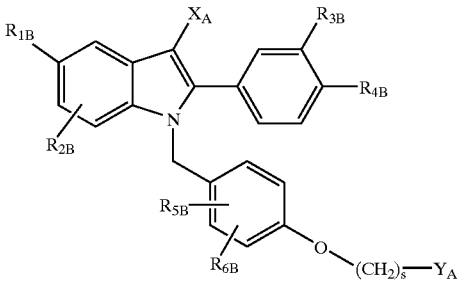

(VI)

wherein:

$R_{1B}$ is selected from H, OH, —O—C(O)—$C_1$–$C_{12}$ alkyl (straight chain or branched), —O—$C_1$–$C_{12}$ alkyl (straight chain or branched or cyclic), or halogens or $C_1$–$C_4$ halogenated ethers;

$R_{2B}$, $R_{3B}$, $R_{4B}$, $R_{5B}$, and $R_{6B}$ are independently selected from H, OH, —O—C(O)—$C_1$–$C_{12}$ (straight chain or branched), —O—$C_1$–$C_{12}$ (straight chain or branched or cyclic), halogens, or $C_1$–$C_4$ halogenated ethers, cyano, $C_1$–$C_6$ alkyl (straight chain or branched), or trifluoromethyl;

$X_A$ is selected from H, $C_1$–$C_6$ alkyl, cyano, nitro, trifluoromethyl, and halogen;

s is 2 or 3;

$Y_A$; is the moiety:

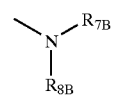

wherein:

a) $R_{7B}$ and $R_{8B}$ are independently selected from the group of H, $C_1$–$C_6$ alkyl, or phenyl optionally substituted by CN, $C_1$–$C_6$ alkyl (straight chain or branched), $C_1$–$C_6$ alkoxy (straight chain or branched), halogen, —OH, —$CF_3$, or —$OCF_3$; or b) $R_{7B}$ and $R_{8B}$ are concatenated to form a five-membered saturated heterocycle containing one nitrogen heteroatom, the heterocycle being optionally substituted with 1–3 substituents independently selected from the group consisting of hydrogen, hydroxyl, halo, $C_1$–$C_4$ alkyl, trihalomethyl, $C_1$–$C_4$ alkoxy, trihalomethoxy, $C_1$–$C_4$ acyloxy, $C_1$–$C_4$ alkylthio, $C_1$–$C_4$ alkylsulfinyl, $C_1$–$C_4$ alkylsulfonyl, hydroxy ($C_1$–$C_4$)alkyl, —$CO_2H$, —CN, —$CONHR_{1B}$, —$NH_2$, —NH($C_1$–$C_4$ alkyl), —N($C_1$–$C_4$ alkyl)$_2$, —$NHSO_2R_{1B}$, —$NHCOR_{1B}$, —$NO_2$, or phenyl optionally substituted with 1–3 ($C_1$–$C_4$)alkyl; or c) $R_{7B}$ and $R_{8B}$ are concatenated to form a six-membered saturated heterocycle containing one nitrogen heteroatom, the heterocycle being optionally substituted with 1–3 substituents independently selected from the group consisting of hydrogen, hydroxyl, halo, $C_1$–$C_4$ alkyl, trihalomethyl, $C_1$–$C_4$ alkoxy, trihalomethoxy, $C_1$–$C_4$ acyloxy, $C_1$–$C_4$ alkylthio, $C_1$–$C_4$alkylsulfinyl, $C_1$–$C_4$ alkylsulfonyl, hydroxy ($C_1$–$C_4$)alkyl, —$CO_2H$, —CN, —$CONHR_{1B}$, —$NH_2$, —NH($C_1$–$C_4$ alkyl), —N($C_1$–$C_4$ alkyl)$_2$, —$NHSO_2R_{1B}$, —$NHCOR_{1B}$, —$NO_2$, or phenyl optionally substituted with 1–3 ($C_1$–$C_4$)alkyl; or d) $R_{7B}$ and $R_{8B}$ are concatenated to form a seven-membered saturated heterocycle containing one nitrogen heteroatom, the heterocycle being optionally substituted with 1–3 substituents independently selected from the group consisting of hydrogen, hydroxyl, halo, $C_1$–$C_4$ alkyl, trihalomethyl, $C_1$–$C_4$ alkoxy, trihalomethoxy, $C_1$–$C_4$ acyloxy, $C_1$–$C_4$ alkylthio, $C_1$–$C_4$ alkylsulfinyl, $C_1$–$C_4$ alkylsulfonyl, hydroxy ($C_1$–$C_4$)alkyl, —$CO_2H$, —CN, —$CONHR_{1B}$, —$NH_2$, —NH($C_1$–$C_4$ alkyl), —N($C_1$–$C_4$ alkyl)$_2$, —$NHSO_2R_{1B}$, $NHCOR_{1B}$, —$NO_2$, or phenyl optionally substituted with 1–3 ($C_1$–$C_4$)alkyl; or e) $R_{7B}$ and $R_{8B}$ are concatenated to form an eight-membered saturated heterocycle containing one nitrogen heteroatom, the heterocycle being optionally substituted with 1–3 substituents independently selected from the group consisting of hydrogen, hydroxyl, halo, $C_1$–$C_4$ alkyl, trihalomethyl, $C_1$–$C_4$ alkoxy, trihalomethoxy, $C_1$–$C_4$ acyloxy, $C_1$–$C_4$ alkylthio, $C_1$–$C_4$ alkylsulfinyl, $C_1$–$C_4$ alkylsulfonyl, hydroxy ($C_1$–$C_4$)alkyl, —$CO_2H$, —CN, —$CONHR_{1B}$, —$NH_2$, —NH($C_1$–$C_4$ alkyl), —N($C_1$–$C_4$ alkyl)$_2$, —$NHSO_2R_{1B}$, —$NHCOR_{1B}$, —$NO_2$, or phenyl optionally substituted with 1–3 ($C_1$–$C_4$)alkyl; or f) $R_{7B}$ and $R_{8B}$ are concatenated to form a saturated bicyclic heterocycle containing from 6–12 carbon atoms either bridged or fused and containing one nitrogen heteroatom, the heterocycle being optionally substituted with 1–3 substituents independently selected from the group consisting of hydrogen, hydroxyl, halo, $C_1$–$C_4$ alkyl, trihalomethyl, $C_1$–$C_4$ alkoxy, trihalomethoxy, $C_1$–$C_4$ acyloxy, $C_1$–$C_4$ alkylthio, $C_1$–$C_4$ alkylsulfinyl, $C_1$–$C_4$ alkylsulfonyl, hydroxy ($C_1$–$C_4$)alkyl, —$CO_2H$, —CN, —$CONHR_{1B}$, —$NH_2$, —NH($C_1$–$C_4$ alkyl), —N($C_1$–$C_4$ alkyl)$_2$, —$NHSO_2R_{1B}$, —$NHCOR_{1B}$, —$NO_2$, or phenyl optionally substituted with 1–3 ($C_1$–$C_4$) alkyl;

or an optical or geometric isomer thereof; or a pharmaceutically acceptable salt, N-oxide, ester, quaternary ammonium salt or prodrug thereof.

In another preferred embodiment of the methods, the estrogen agonist/antagonist is the compound TSE-424 of formula Va below:

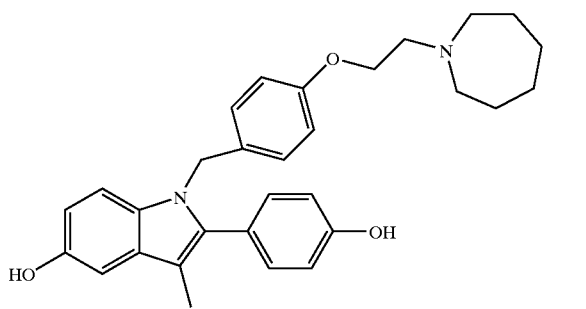

or an optical or geometric isomer thereof; or a pharmaceutically acceptable salt, N-oxide, ester, quaternary ammonium salt or prodrug thereof.

In another preferred embodiment of the methods, the estrogen agonist/antagonist is EM-652 of formula III below or is EM-800 of formula IV below:

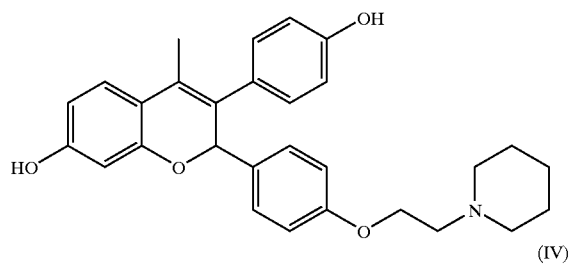

(III)

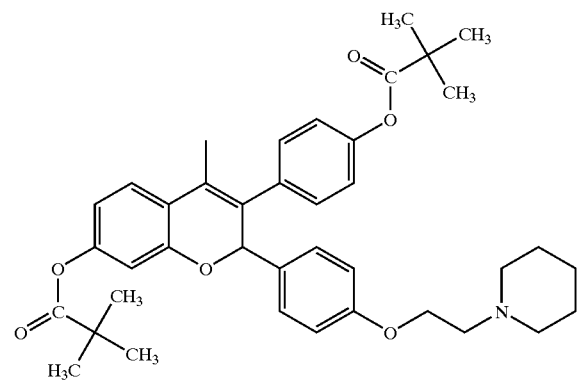

(IV)

or an optical or geometric isomer thereof; or a pharmaceutically acceptable salt, N-oxide, ester, quaternary ammonium salt or prodrug thereof.

In another embodiment of the methods, a second compound that is useful to prevent myocardial infarction or stroke; maintain or improving vascular reactivity; or treat acute or chronic renal failure, peripheral arterial occlusive disease, coronary artery disease, or Raynaud's phenomenon, is administered to the patient.

Also provided are methods of lowering the plasma concentration of Lp(a), the method comprising administering to a patient in need of plasma Lp(a) lowering a therapeutically effective amount of an estrogen agonist/antagonist.

In a preferred embodiment of the methods, the estrogen agonist/antagonist is a compound of formula (I):

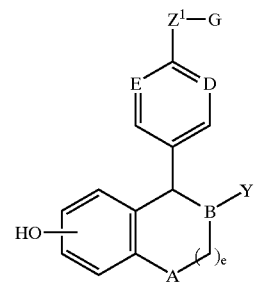

(I)

wherein:
A is selected from $CH_2$ and NR;
B, D and E are independently selected from CH and N;
Y is
(a) phenyl, optionally substituted with 1–3 substituents independently selected from $R^4$;
(b) naphthyl, optionally substituted with 1–3 substituents independently selected from $R^4$;

(c) C$_3$–C$_8$ cycloalkyl, optionally substituted with 1–2 substituents independently selected from R$^4$;

(d) C$_3$–C$_8$ cycloalkenyl, optionally substituted with 1–2 substituents independently selected from R$^4$;

(e) a five membered heterocycle containing up to two heteroatoms selected from the group consisting of —O—, —NR$^2$— and —S(O)$_n$—, optionally substituted with 1–3 substituents independently selected from R$^4$;

(f) a six membered heterocycle containing up to two heteroatoms selected from the group consisting of —O—, —NR$^2$— and —S(O)$_n$— optionally substituted with 1–3 substituents independently selected from R$^4$; or (g) a bicyclic ring system consisting of a five or six membered heterocyclic ring fused to a phenyl ring, said heterocyclic ring containing up to two heteroatoms selected from the group consisting of —O—, —NR$^2$— and —S(O)$_n$—, optionally substituted with 1–3 substituents independently selected from R$^4$;

Z$^1$ is (a) —(CH$_2$)$_p$W(CH$_2$)$_q$—;
(b) —O(CH$_2$)$_p$CR$^5$R$^6$—;
(c) —O(CH$_2$)$_p$W(CH$_2$)$_q$—;
(d) —OCHR$^2$CHR$^3$—; or
(e) —SCHR$^2$CHR$^3$—;

G is (a) —NR$^7$R$^8$;
(b)

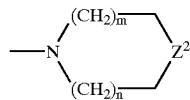

wherein n is 0, 1 or 2; m is 1, 2 or 3; Z$^2$ is —NH—, —O—, —S—, or —CH$_2$—; optionally fused on adjacent carbon atoms with one or two phenyl rings and, optionally independently substituted on carbon with one to three substituents and, optionally, independently on nitrogen with a chemically suitable substituent selected from R$^4$; or (c) a bicyclic amine containing five to twelve carbon atoms, either bridged or fused and optionally substituted with 1–3 substituents independently selected from R$^4$; or Z$^1$ and G in combination may be

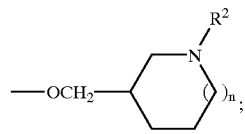

W is (a) —CH$_2$—;
(b) —CH=CH—;
(c) —O—;
(d) —NR$^2$—;
(e) —S(O)$_n$—;

(f)

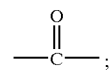

(g) —CR$^2$(OH)—;
(h) —CONR$^2$;
(i) —NR$^2$CO;
(j)

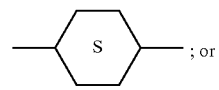

(k) —C≡C—;

R is hydrogen or C$_1$–C$_6$ alkyl;
R$^2$ and R$^3$ are independently
(a) hydrogen; or
(b) C$_1$–C$_4$ alkyl;

R$^4$ is
(a) hydrogen;
(b) halogen;
(c) C$_1$–C$_6$ alkyl;
(d) C$_1$–C$_4$ alkoxy;
(e) C$_1$–C$_4$ acyloxy;
(f) C$_1$–C$_4$ alkylthio;
(g) C$_1$–C$_4$ alkylsulfinyl;
(h) C$_1$–C4 alkylsulfonyl;
(i) hydroxy (C$_1$–C$_4$)alkyl;
(j) aryl (C$_1$–C$_4$)alkyl;
(k) —CO$_2$H;
(l) —CN;
(m) —CONHOR;
(n) —SO$_2$NHR;
(o) —NH$_2$;
(p) C$_1$–C$_4$ alkylamino;
(q) C$_1$–C$_4$ dialkylamino;
(r) —NHSO$_2$R;
(s) —NO$_2$;
(t) -aryl; or
(u) —OH;

R$^5$ and R$^6$ are independently C$_1$–C$_8$ alkyl or together form a C$_3$–C$_{10}$ carbocyclic ring;

R$^7$ and R$^8$ are independently
(a) phenyl;
(b) a C$_3$–C$_{10}$ carbocyclic ring, saturated or unsaturated;
(c) a C$_3$–C$_{10}$ heterocyclic ring containing up to two heteroatoms, selected from —O—, —N—and —S—;
(d) H;
(e) C$_1$–C$_6$ alkyl; or
(f) form a 3 to 8 membered nitrogen containing ring with R$^5$ or R$^6$;

R$^7$ and R$^8$ in either linear or ring form may optionally be substituted with up to three substituents independently selected from C$_1$–C$_6$ alkyl, halogen, alkoxy, hydroxy and carboxy;

a ring formed by R$^7$ and R$^8$ may be optionally fused to a phenyl ring;

e is 0, 1 or 2;

m is 1, 2 or 3;

n is 0, 1 or 2;

p is 0, 1, 2 or 3;

q is 0, 1, 2 or 3;

or an optical or geometric isomer thereof; or a pharmaceutically acceptable salt, N-oxide, ester, quaternary ammonium salt or prodrug thereof.

In another preferred embodiment of the methods, the estrogen agonist/antagonist is a compound of formula (IA):

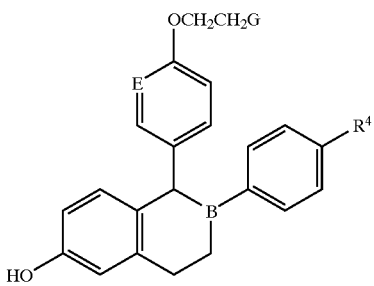
(IA)

wherein;

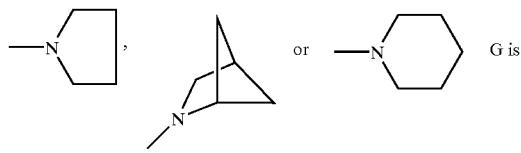

$R^4$ is H, OH, F, or Cl; and B and E are independently selected from CH and N or an optical or geometric isomer thereof; or a pharmaceutically acceptable salt, N-oxide, ester, quaternary ammonium salt, or a prodrug thereof.

In another preferred embodiment of the methods, the estrogen agonist/antagonist is (−)-cis-6-phenyl-5-[4-(2-pyrrolidin-1-yl-ethoxy)-phenyl]-5,6,7,8-tetrahydro-naphthalene-2-ol or an optical or geometric isomer thereof; a pharmaceutically acceptable salt, N-oxide, ester, quaternary ammonium salt, or a prodrug thereof.

In another preferred embodiment of the methods, the estrogen agonist/antagonist is (−)-cis-6-phenyl-5-[4-(2-pyrrolidin-1-yl-ethoxy)-phenyl]-5,6,7,8-tetrahydro-naphthalene-2-ol, D-tartrate salt.

In another preferred embodiment of the methods, the estrogen agonist/antagonist is a compound selected from the formulas V or VI:

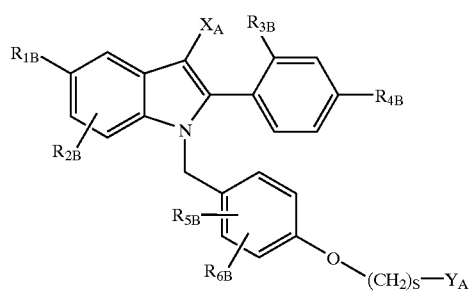
(V)

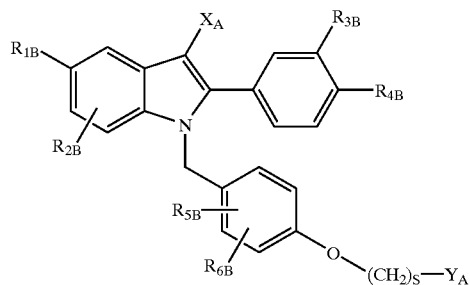
(VI)

wherein:
$R_{1B}$ is selected from H, OH, —O—C(O)—$C_1$-$C_{12}$ alkyl (straight chain or branched), —O—$C_1$-$C_{12}$ alkyl (straight chain or branched or cyclic), or halogens or $C_1$-$C_4$ halogenated ethers;

$R_{2B}$, $R_{3B}$, $R_{4B}$, $R_{5B}$, and $R_{6B}$ are independently selected from H, OH, —O—C(O)—$C_1$-$C_{12}$ (straight chain or branched), —$C_1$-$C_{12}$ (straight chain or branched or cyclic), halogens, or $C_1$-$C_4$ halogenated ethers, cyano, $C_1$-$C_6$ alkyl (straight chain or branched), or trifluoromethyl;

$X_A$ is selected from H, $C_1$-$C_6$ alkyl, cyano, nitro, trifluoromethyl, and halogen;

s is 2 or 3;

$Y_A$ is the moiety:

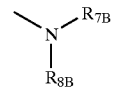

wherein:
a) $R_{7B}$ and $R_{8B}$ are independently selected from the group of H, $C_1$-$C_6$ alkyl, or phenyl optionally substituted by CN, $C_1$-$C_6$ alkyl (straight chain or branched), $C_1$-$C_8$ alkoxy (straight chain or branched), halogen, —OH, —$CF_3$, or —$OCF_3$; or b) $R_{7B}$ and $R_{8B}$ are concatenated to form a five-membered saturated heterocycle containing one nitrogen heteroatom, the heterocycle being optionally substituted with 1–3 substituents independently selected from the group consisting of hydrogen, hydroxyl, halo, $C_1$-$C_4$ alkyl, trihalomethyl, $C_1$-$C_4$ alkoxy, trihalomethoxy, $C_1$-$C_4$ acyloxy, $C_1$-$C_4$ alkylthio, $C_1$-$C_4$ alkylsulfinyl, $C_1$-$C_4$ alkylsulfonyl, hydroxy ($C_1$-$C_4$)alkyl, —$CO_2H$, —CN, —$CONHR_{1B}$, —$NH_2$, —NH($C_1$-$C_4$ alkyl), —N($C_1$-$C_4$ alkyl)$_2$, —$NHSO_2R_{1B}$, —$NHCOR_{1B}$, —$NO_2$, or phenyl optionally substituted with 1–3 ($C_1$-$C_4$)alkyl; or c) $R_{7B}$ and $R_{8B}$ are concatenated to form a six-membered saturated heterocycle containing one nitrogen heteroatom, the heterocycle being optionally substituted with 1–3 substituents independently selected from the group consisting of hydrogen, hydroxyl, halo, $C_1$-$C_4$ alkyl, trihalomethyl, $C_1$-$C_4$ alkoxy, trihalomethoxy, $C_1$-$C_4$ acyloxy, $C_1$-$C_4$ alkylthio, $C_1$-$C_4$alkylsulfinyl, $C_1$-$C_4$ alkylsulfonyl, hydroxy ($C_1$-$C_4$)alkyl, —$CO_2H$, —CN, —$CONHR_{1B}$, —$NH_2$, —NH($C_1$-$C_4$ alkyl), —N($C_1$-$C_4$ alkyl)$_2$, —$NHSO_2R_{1B}$, —$NHCOR_{1B}$, —$NO_2$, or phenyl optionally substituted with 1–3 ($C_1$-$C_4$)alkyl; or d) $R_{7B}$ and $R_{8B}$ are concatenated to form a seven-membered saturated heterocycle containing one nitrogen heteroatom, the heterocycle being optionally substituted with 1–3 substituents independently selected from the group consisting of hydrogen, hydroxyl, halo, $C_1$–$C_4$ alkyl, trihalomethyl, $C_1$–$C_4$ alkoxy, trihalomethoxy, $C_1$–$C_4$ acyloxy, $C_1$–$C_4$ alkylthio, $C_1$–$C_4$ alkylsulfinyl, $C_1$–$C_4$ alkylsulfonyl, hydroxy ($C_1$–$C_4$)alkyl, —$CO_2H$, —CN, —$CONHR_{1B}$, —$NH_2$, —NH($C_1$–$C_4$ alkyl), —N($C_1$–$C_4$ alkyl)$_2$, —$NHSO_2 R_{1B}$, —$NHCOR_{1B}$, —$NO_2$, or phenyl optionally substituted with 1–3 ($C_1$–$C_4$)alkyl; or e) $R_{7B}$ and $R_{8B}$ are concatenated to form an eight-membered saturated heterocycle containing one nitrogen heteroatom, the heterocycle being optionally substituted with 1–3 substituents independently selected from the group consisting of hydrogen, hydroxyl, halo, $C_1$–$C_4$ alkyl, trihalomethyl, $C_1$–$C_4$ alkoxy, trihalomethoxy, $C_1$–$C_4$ acyloxy, $C_1$–$C_4$ alkylthio, $C_1$–$C_4$ alkylsulfinyl, $C_1$–$C_4$ alkylsulfonyl, hydroxy ($C_1$–$C_4$)alkyl, —$CO_2H$, —CN, —$CONHR_{1B}$, —$NH_2$, —NH($C_1$–$C_4$ alkyl), —N($C_1$–$C_4$ alkyl)$_2$, —$NHSO_2R_{1B}$, —$NHCOR_{1B}$, —$NO_2$, or phenyl optionally substituted with 1–3 ($C_1$–$C_4$)alkyl; or f) $R_{7B}$ and $R_{8B}$ are concatenated to form a saturated bicyclic heterocycle containing from 6–12 carbon atoms either bridged or fused and containing one nitrogen heteroatom, the heterocycle being optionally substituted with 1–3 substituents independently selected from the group consisting of hydrogen, hydroxyl, halo, $C_1$–$C_4$ alkyl, trihalomethyl, $C_1$–$C_4$ alkoxy, trihalomethoxy, $C_1$–$C_4$ acyloxy, $C_1$–$C_4$ alkylthio, $C_1$–$C_4C_4$ alkylsulfinyl, $C_1$–$C_4$ alkylsulfonyl, hydroxy ($C_1$–$C_4$)alkyl, —$CO_2H$, —CN, —$CONHR_{1B}$, —$NH_2$, —NH($C_1$–$C_4$ alkyl), —N($C_1$–$C_4$ alkyl)$_2$, —$NHSO_2R_{1B}$, —$NHCOR_{1B}$, —$NO_2$, or phenyl optionally substituted with 1–3 ($C_1$–$C_4$) alkyl;

or an optical or geometric isomer thereof; or a pharmaceutically acceptable salt, N-oxide, ester, quaternary ammonium salt or prodrug thereof.

In another preferred embodiment of the methods, the estrogen agonist/antagonist is the compound TSE-424 of formula Va below:

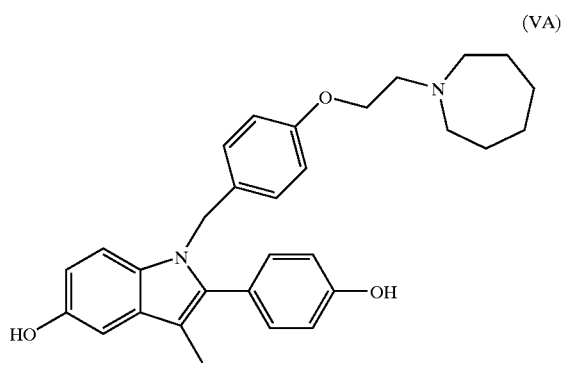

(VA)

or an optical or geometric isomer thereof; or a pharmaceutically acceptable salt, N-oxide, ester, quaternary ammonium salt or prodrug thereof.

In another preferred embodiment of the methods, the estrogen agonist/antagonist is EM-652 of formula III below or is EM-800 of formula IV below:

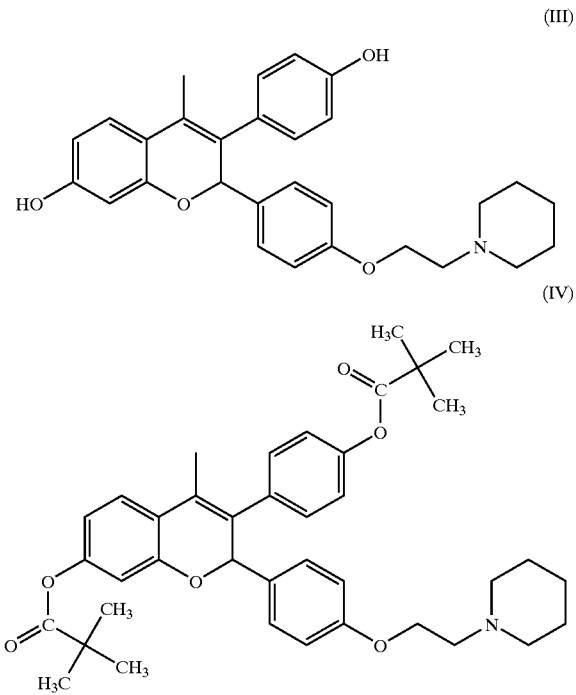

or an optical or geometric isomer thereof; or a pharmaceutically acceptable salt, N-oxide, ester, quaternary ammonium salt or prodrug thereof.

In another preferred embodiment of the methods, a second compound that is useful to prevent myocardial infarction or stroke; maintain or improving vascular reactivity; treat acute or chronic renal failure, peripheral arterial occlusive disease, coronary artery disease, or Raynaud's phenomenon; or lower plasma levels of Lp(a) is administered to the patient.

Also provided by the present invention are kits for use by a consumer to prevent myocardial infarction or stroke; maintain or improve vascular reactivity; treat acute or chronic renal failure, peripheral arterial occlusive disease, coronary artery disease, or Raynaud's phenomenon; or lower plasma levels of Lp(a), the kits comprising:

(a) a pharmaceutical composition comprising an estrogen agonist/antagonist and a pharmaceutically acceptable carrier, vehicle or diluent; and (b) instructions describing a method of using the pharmaceutical composition to prevent myocardial infarction or stroke; maintain or improve vascular reactivity; treat acute or chronic renal failure, peripheral arterial occlusive disease, cornary artery disease or Raynaud's phenomenon; or lower plasma levels of Lp(a).

In a preferred embodiment of the kits, the estrogen agonist/antagonist is a compound of formula (I):

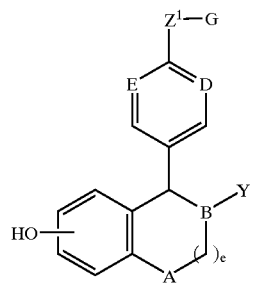

(I)

wherein:
A is selected from CH₂ and NR;
B, D and E are independently selected from CH and N;
Y is
(a) phenyl, optionally substituted with 1–3 substituents independently selected from R⁴;
(b) naphthyl, optionally substituted with 1–3 substituents independently selected from R⁴;
(c) $C_3$–$C_8$ cycloalkyl, optionally substituted with 1–2 substituents independently selected from $R_4$;
(d) $C_3$–$C_8$ cycloalkenyl, optionally substituted with 1–2 substituents independently selected from R⁴;
(e) a five membered heterocycle containing up to two heteroatoms selected from the group consisting of —O—, —NR²— and —S(O)$_n$—, optionally substituted with 1–3 substituents independently selected from R⁴;
(f) a six membered heterocycle containing up to two heteroatoms selected from the group consisting of —O—, —NR²— and —S(O)$_n$— optionally substituted with 1–3 substituents independently selected from R⁴; or
(g) a bicyclic ring system consisting of a five or six membered heterocyclic ring fused to a phenyl ring, said heterocyclic ring containing up to two heteroatoms selected from the group consisting of —O—, —NR²— and —S(O)$_n$—, optionally substituted with 1–3 substituents independently selected from R⁴;
Z¹ is
(a) —(CH₂)$_p$W(CH₂)$_q$—;
(b) —O(CH₂)$_p$CR⁵R⁶—;
(c) —O(CH₂)$_p$W(CH₂)$_q$—;
(d) —OCHR²CHR³; or
(e) —SCHR²CHR³—;
G is
(a) —NR⁷R⁸;
(b)

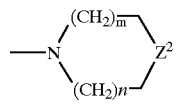

wherein n is 0, 1 or 2; m is 1, 2 or 3; Z² is —NH—, —O—, —S—, or —CH₂—; optionally fused on adjacent carbon atoms with one or two phenyl rings and, optionally independently substituted on carbon with one to three substituents and, optionally, independently on nitrogen with a chemically suitable substituent selected from R⁴; or
(c) a bicyclic amine containing five to twelve carbon atoms, either bridged or fused and optionally substituted with 1–3 substituents independently selected from R⁴; or Z¹ and G in combination may be

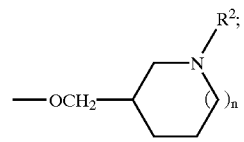

W is
(a) —CH₂—;
(b) —CH=CH—;
(c) —O—;
(d) —NR²—;
(e) —S(O)$_n$—;
(f)

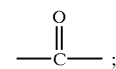

(g) —CR²(OH)—;
(h) —CONR²—;
(i) —NR²CO—;
(j)

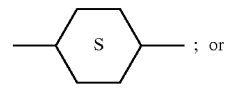

; or (k) —C≡C—;
R is hydrogen or $C_1$–$C_6$ alkyl;
R² and R³ are independently
(a) hydrogen; or
(b) $C_1$–$C_4$ alkyl;
R⁴ is
(a) hydrogen;
(b) halogen;
(c) $C_1$–$C_6$ alkyl;
(d) $C_1$–$C_4$ alkoxy;
(e) $C_1$–$C_4$ acyloxy;
(f) $C_1$–$C_4$ alkylthio;
(g) $C_1$–$C_4$ alkylsulfinyl;
(h) $C_1$–$C_4$ alkylsulfonyl;
(i) hydroxy ($C_1$–$C_4$)alkyl;
(j) aryl ($C_1$–$C_4$)alkyl;
(k) —CO₂H;
(l) —CN;
(m) —CONHOR;
(n) —SO₂NHR;
(o) —NH₂;
(p) $C_1$–$C_4$ alkylamino;
(q) $C_1$–$C_4$ dialkylamino;
(r) —NHSO₂R;
(s) —NO₂;
(t) —aryl; or
(u) —OH;
R⁵ and R⁶ are independently $C_1$–$C_8$ alkyl or together form a $C_3$–$C_{10}$ carbocyclic ring;
R⁷ and R⁸ are independently (a) phenyl;

(b) a $C_3$–$C_{10}$ carbocyclic ring, saturated or unsaturated;

(c) a $C_3$–$C_{10}$ heterocyclic ring containing up to two heteroatoms, selected from —O—, —N— and —S—;

(d) H;

(e) $C_1$–$C_6$ alkyl; or (f) form a 3 to 8 membered nitrogen containing ring with $R^5$ or $R^6$;

$R^7$ and $R^8$ in either linear or ring form may optionally be substituted with up to three substituents independently selected from $C_1$–$C_6$ alkyl, halogen, alkoxy, hydroxy and carboxy;

a ring formed by $R^7$ and $R^8$ may be optionally fused to a phenyl ring;

e is 0, 1 or 2;

m is 1, 2 or 3;

n is 0, 1 or 2;

p is 0, 1, 2 or 3;

q is 0, 1, 2 or 3;

or an optical or geometric isomer thereof; or a pharmaceutically acceptable salt, N-oxide, ester, quaternary ammonium salt or prodrug thereof.

In another preferred embodiment of the kits, the estrogen agonist/antagonist is a compound of formula (IA):

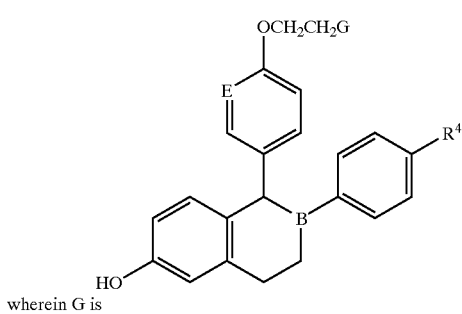

(IA)

wherein G is

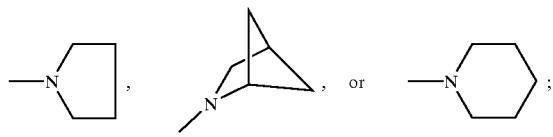

$R^4$ is H, OH, F, or Cl; and B and E are independently selected from CH and N or an optical or geometric isomer thereof; or a pharmaceutically acceptable salt, N-oxide, ester, quaternary ammonium salt, or a prodrug thereof.

In another preferred embodiment of the kits, the estrogen agonist/antagonist is (-)-cis-6-phenyl-5-[4-(2-pyrrolidin-1-yl-ethoxy)-phenyl]-5,6,7,8-tetrahydro-naphthalene-2-ol or an optical or geometric isomer thereof, or a pharmaceutically acceptable salt, N-oxide, ester, quaternary ammonium salt, or a prod rug thereof.

In another preferred embodiment of the kits, the estrogen agonist/antagonist is (-)-cis-6-phenyl-5-[4-(2-pyrrolidin-1-yl-ethoxy)-phenyl]-5,6,7,8-tetrahydro-naphthalene-2-ol, D-tartrate salt.

In another preferred embodiment of the kits, the estrogen agonist/antagonist is a compound selected from the formulas V or VI:

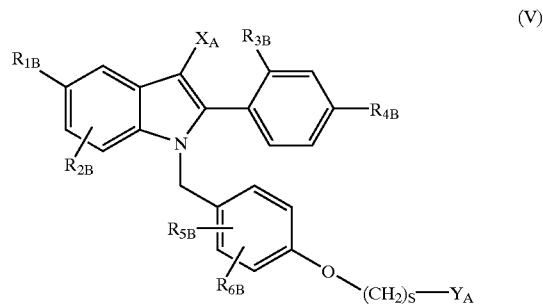

(V)

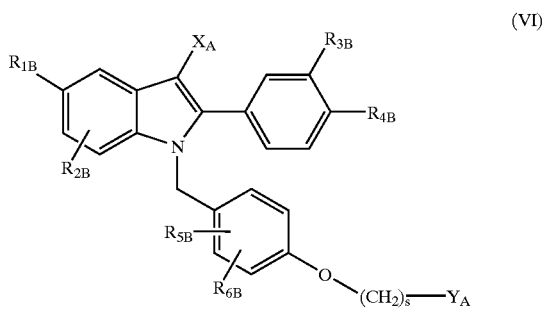

(VI)

wherein:

$R_{1B}$ is selected from H, OH, —O—C(O)—$C_1$–$C_{12}$ alkyl (straight chain or branched), —O—$C_1$–$C_{12}$ alkyl (straight chain or branched or cyclic), or halogens or $C_1$–$C_4$ halogenated ethers;

$R_{2B}$, $R_{3B}$, $R_{4B}$, $R_{5B}$, and $R_{6B}$ are independently selected from H, OH, —O—C(O)—$C_1$–$C_{12}$ (straight chain or branched), —O—$C_1$–$C_{12}$ (straight chain or branched or cyclic), halogens, or $C_1$–$C_4$ halogenated ethers, cyano, $C_1$–$C_6$ alkyl (straight chain or branched), or trifluoromethyl;

$X_A$ is selected from H, $C_1$–$C_6$ alkyl, cyano, nitro, trifluoromethyl, and halogen;

s is 2 or 3;

$Y_A$ is the moiety:

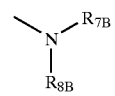

wherein:

a) $R_{7B}$ and $R_{8B}$ are independently selected from the group of H, $C_1$–$C_6$ alkyl, or phenyl optionally substituted by CN, $C_1$–$C_6$ alkyl (straight chain or branched), $C_1$–$C_6$ alkoxy (straight chain or branched), halogen, —OH, —$CF_3$, or —$OCF_3$; or b) $R_{7B}$ and $R_{8B}$ are concatenated to form a five-membered saturated heterocycle containing one nitrogen heteroatom, the heterocycle being optionally substituted with 1–3 substituents independently selected from the group consisting of hydrogen, hydroxyl, halo, $C_1$–$C_4$ alkyl, trihalomethyl, $C_1$–$C_4$ alkoxy, trihalomethoxy, $C_1$–$C_4$ acyloxy, $C_1$–$C_4$ alkylthio, $C_1$–$C_4$ alkylsulfinyl, $C_1$–$C_4$ alkylsulfonyl, hydroxy ($C_1$–$C_4$)alkyl, —$CO_2H$, —CN, —$CONHR_{1B}$, —$NH_2$, —NH($C_1$–$C_4$ alkyl), —N($C_1$–$C_4$ alkyl)$_2$, —NHSO$_2$R$_{1B}$, —NHCOR$_{1B}$, —NO$_2$, or phenyl optionally substituted with 1–3 ($C_1$–$C_4$)alkyl; or c) R$_{7B}$ and R$_{8B}$ are concatenated to form a six-membered saturated heterocycle containing one nitrogen heteroatom, the heterocycle being optionally substituted with 1–3 substituents independently selected from the group consisting of hydrogen, hydroxyl, halo, $C_1$–$C_4$ alkyl, trihalomethyl, $C_1$–$C_4$ alkoxy, trihalomethoxy, $C_1$–$C_4$ acyloxy, $C_1$–$C_4$ alkylthio, C–$C_4$alkylsulfinyl, $C_1$–$C_4$ alkylsulfonyl, hydroxy ($C_1$–$C_4$)alkyl, —CO$_2$H, —CN, —CONHR$_{1B}$, —NH$_2$, —NH($C_1$–$C_4$ alkyl), —N($C_1$–$C_4$ alkyl)$_2$, —NHSO$_2$R$_{1B}$, —NHCOR$_{1B}$, —NO$_2$, or phenyl optionally substituted with 1–3 ($C_1$–$C_4$)alkyl; or d) R$_{7B}$ and R$_{8B}$ are concatenated to form a seven-membered saturated heterocycle containing one nitrogen heteroatom, the heterocycle being optionally substituted with 1–3 substituents independently selected from the group consisting of hydrogen, hydroxyl, halo, $C_1$–$C_4$ alkyl, trihalomethyl, $C_1$–$C_4$ alkoxy, trihalomethoxy, $C_1$–$C_4$ acyloxy, $C_1$–$C_4$ alkylthio, $C_1$–$C_4$ alkylsulfinyl, $C_1$–$C_4$ alkylsulfonyl, hydroxy ($C_1$–$C_4$)alkyl, —CO$_2$H, —CN, —CONHR$_{1B}$, —NH$_2$, —NH($C_1$–$C_4$ alkyl), —N($C_1$–$C_4$ alkyl)$_2$, —NHSO$_2$R$_{1B}$, —NHCOR$_{1B}$, —NO$_2$, or phenyl optionally substituted with 1–3 ($C_1$–$C_4$)alkyl; or e) R$_{7B}$ and R$_{8B}$ are concatenated to form an eight-membered saturated heterocycle containing one nitrogen heteroatom, the heterocycle being optionally substituted with 1–3 substituents independently selected from the group consisting of hydrogen, hydroxyl, halo, $C_1$–$C_4$ alkyl, trihalomethyl, $C_1$–$C_4$ alkoxy, trihalomethoxy, $C_1$–$C_4$ acyloxy, $C_1$–$C_4$ alkylthio, $C_1$–$C_4$ alkylsulfinyl, $C_1$–$C_4$ alkylsulfonyl, hydroxy ($C_1$–$C_4$)alkyl, —CO$_2$H, —CN, —CONHR$_{1B}$, —NH$_2$, —NH($C_1$–$C_4$ alkyl), —N($C_1$–$C_4$ alkyl)$_2$, —NHSO$_2$R$_{1B}$, —NHCOR$_{1B}$, —NO$_2$, or phenyl optionally substituted with 1–3 ($C_1$–$C_4$)alkyl; or f) R$_{7B}$ and R$_{8B}$ are concatenated to form a saturated bicyclic heterocycle containing from 6–12 carbon atoms either bridged or fused and containing one nitrogen heteroatom, the heterocycle being optionally substituted with 1–3 substituents independently selected from the group consisting of hydrogen, hydroxyl, halo, $C_1$–$C_4$ alkyl, trihalomethyl, $C_1$–$C_4$ alkoxy, trihalomethoxy, $C_1$–$C_4$ acyloxy, $C_1$–$C_4$ alkylthio, $C_1$–$C_4$ alkylsulfinyl, $C_1$–$C_4$ alkylsulfonyl, hydroxy ($C_1$–$C_4$)alkyl, —CO$_2$H, —CN, —CONHR$_{1B}$, —NH$_2$, —NH($C_1$–$C_4$ alkyl), —N($C_1$–$C_4$ alkyl)$_2$, —NHSO$_2$R$_{1B}$, —NHCOR$_{1B}$, —NO$_2$, or phenyl optionally substituted with 1–3 ($C_1$–$C_4$) alkyl;

or an optical or geometric isomer thereof; or a pharmaceutically acceptable salt, N-oxide, ester, quaternary ammonium salt or prodrug thereof.

In another preferred embodiment of the kits, the estrogen agonist/antagonist is the compound TSE-424 of formula Va below:

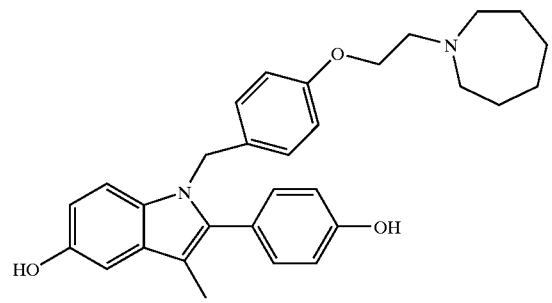

(Va)

or an optical or geometric isomer thereof; or a pharmaceutically acceptable salt, N-oxide, ester, quaternary ammonium salt or prodrug thereof.

In another preferred embodiment of the kits, the estrogen agonist/antagonist is EM-652 of formula III below or EM-800 of formula IV below:

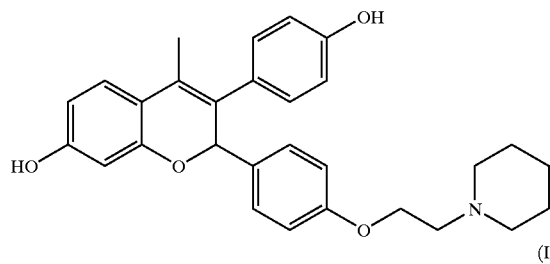

(III)

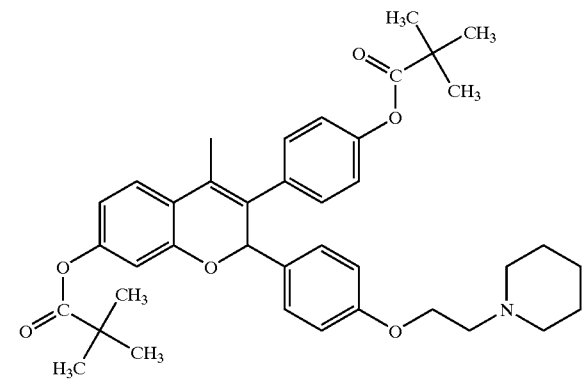

(IV)

or an optical or geometric isomer thereof; or a pharmaceutically acceptable salt, N-oxide, ester, quaternary ammonium salt or prodrug thereof.

In another preferred embodiment of the kits, the kits further comprises an additional compound that is useful to prevent myocardial infarction or stroke; maintain or improve vascular reactivity; treat acute or chronic renal failure, peripheral arterial occlusive disease, coronary artery disease or Raynaud's phenomenon; or lower plasma levels of Lp(a).

DETAILED DESCRIPTION OF THE INVENTION

This invention relates to methods and kits for improving or maintaining vascular health, including preventing myocardial infarction or stroke; maintaining or improving vascular reactivity; treating acute or chronic renal failure, peripheral arterial occlusive disease, coronary artery disease, Raynaud's phenomenon; or lowering plasma levels of Lp(a) using an estrogen agonist/antagonist.

The following terms are defined below:

The terms "treat", "treatment", and "treating" include preventative (e.g., prophylactic) and palliative treatment or the act of providing preventative or palliative treatment.

The term "patient" means animals, particularly mammals. Preferred patients are humans. Particularly preferred patients are postmenopausal women.

A patient in need of Lp(a) lowering is a patient who has a high plasma concentration of Lp(a). It is believed that a human patient who has a plasma concentration of Lp(a) that is higher that about 30 mg/dL is in need of plasma Lp(a) lowering. "Adverse effects associated with estrogen" include breast tenderness, bloating, headache, increased blood clotting and menstrual bleeding in women. Unopposed estrogen therapy increases the risk of endometrial carcinoma. Women on long-term estrogen therapy may have an increased risk that is not reversed by concurrent progestin (N Engl J Med 1995;332:1589).

The term "postmenopausal women" includes not only women of advanced age who have passed through menopause, but also women who have been hysterectomized or for some other reason have suppressed estrogen production, such as those who have undergone long-term administration of corticosteroids, suffer from Cushings' syndrome, or have gonadal dysgenesis.

"Breast cancer" is defined as a malignant proliferation of epithelial cells lining the ducts or lobules of the breast.

An "estrogen agonist/antagonist" is a compound that affects some of the same receptors that estrogen does, but not all, and in some instances, it antagonizes or blocks estrogen. It is also known as a "selective estrogen receptor modulator" (SERM). Estrogen agonists/antagonists may also be referred to as antiestrogens although they have some estrogenic activity at some estrogen receptors. Estrogen agonists/antagonists are therefore not what are commonly referred to as "pure antiestrogens". Antiestrogens that can also act as agonists are referred to as Type I antiestrogens. Type I antiestrogens activate the estrogen receptor to bind tightly in the nucleus for a prolonged time but with impaired receptor replenishment (Clark, et al., Steroids 1973;22:707, Capony et al., Mol Cell Endocrinol, 1975;3:233).

Vascular reactivity relates to a blood vessel's ability to dilate and contract after presented with certain stimuli. The ability of a blood vessel to react appropriately to stimuli is important. For example, constriction of blood vessels during an ischemic event results in further ischemia and can exacerbate the damage caused by the ischemia.

Stroke is one of the most common causes of death in the United States. The term cerebrovascular disease has also been used to describe stroke. A stroke can comprise both ischemic events, which are typically caused by arteriosclerotic or hypertensive stenosis, thrombosis or embolism, and hemorrhagic events, which typically result in bleeding in the brain tissue, the epidural, subdural or subarachnoid space, or combinations thereof.

Myocardial infarction is also call heart attack. A heart attack occurs when heart tissue is damaged by an inadequate supply of blood to the heart tissue.

Peripheral arterial occlusive disease is typically defined as occlusion of the blood supply to the extremities by atherosclerotic plaques (atheromas), a thrombus, or an embolism.

Raynaud's phenomenon is a disease that is secondary to other conditions and is characterized by spasms of the arterioles, usually in the digits and occasionally in other acral parts such as the nose or tongue with intermittent pallor or cyanosis. Raynaud's phenomenon is precipitated by exposure to cold or emotional upset. Frequently, paresthesia occurs.

The estrogen agonists/antagonists of the invention are effective in improving or maintaining vascular health. By improving or maintaining vascular health, the methods and kits of the invention are suitable for treating a variety of specific conditions. These conditions encompass myocardial infarction, stroke, vascular reactivity, coronary artery disease (CAD) such as atherosclerosis, acute and chronic renal failure, peripheral arterial occlusive disease, and Raynaud's phenomenon.

The estrogen agonists/antagonists of the invention are also useful in lowering serum lipoprotein (a) (Lp(a)) in a patient. By lowering Lp(a), the risk of future coronary heart disease events is lowered.

The estrogen agonists/antagonists of the invention may be administered systemically or locally. For systemic use, the estrogen agonists and antagonists herein are formulated for parenteral (e.g., intravenous, subcutaneous, intramuscular, intraperitoneal, intranasal or transdermal) or enteral (e.g., oral or rectal) delivery according to conventional methods. Intravenous administration can be by a series of injections or by continuous infusion over an extended period. Administration by injection or other routes of discretely spaced administration can be performed at intervals ranging from weekly to once to three or more times daily.

Preferred estrogen agonists/antagonists of the present invention include the compounds described in U.S. Pat. No. 5,552,412. Those compounds are described by the formula designated herein as formula (I) given below:

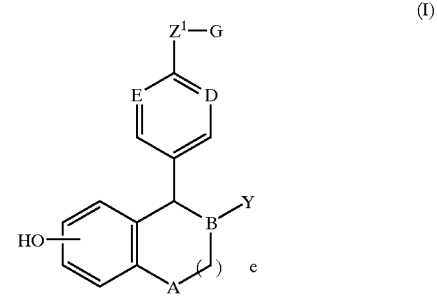

wherein:

A is selected from $CH_2$ and NR;

B, D and E are independently selected from CH and N;

Y is (a) phenyl, optionally substituted with 1–3 substituents independently selected from $R^4$;

(b) naphthyl, optionally substituted with 1–3 substituents independently selected from $R^4$;

(c) $C_3$–$C_8$ cycloalkyl, optionally substituted with 1–2 substituents independently selected from $R^4$;

(d) $C_3$–$C_8$ cycloalkenyl, optionally substituted with 1–2 substituents independently selected from $R^4$;

(e) a five membered heterocycle containing up to two heteroatoms selected from the group consisting of —O—, —NR$^2$— and —S(O)n—, optionally substituted with 1–3 substituents independently selected from R$^4$;

(f) a six membered heterocycle containing up to two heteroatoms selected from the group consisting of —O—, —NR$^2$— and —S(O)$_n$— optionally substituted with 1–3 substituents independently selected from R$^4$; or (g) a bicyclic ring system consisting of a five or six membered heterocyclic ring fused to a phenyl ring, said heterocyclic ring containing up to two heteroatoms selected from the group consisting of —O—, —NR$^2$— and —S(O)$_n$—, optionally substituted with 1–3 substituents independently selected from R$^4$;

Z$^1$ is
(a) —(CH$_2$)$_p$W(CH$_2$)$_q$—;
(b) —O(CH$_2$)$_p$CR$^5$R$^6$—;
(c) —O(CH$_2$)$_p$W(CH$_2$)$_q$—;
(d) —OCHR$^2$CHR$^3$—; or
(e) —SCHR$^2$CHR$^3$—;

G is
(a) —NR$^7$R$^8$;
(b)

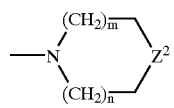

wherein n is 0, 1 or 2; m is 1, 2 or 3; Z$^2$ is —NH—, —O—, —S—, or —CH$_2$—; optionally fused on adjacent carbon atoms with one or two phenyl rings and, optionally independently substituted on carbon with one to three substituents and, optionally, independently on nitrogen with a chemically suitable substituent selected from R$^4$; or (c) a bicyclic amine containing five to twelve carbon atoms, either bridged or fused and optionally substituted with 1–3 substituents independently selected from R$^4$; or Z$^1$ and G in combination may be

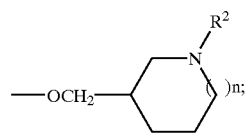

W is
(a) —CH$_2$—;
(b) —CH=CH—;
(c) —O—;
(d) —NR$^2$—;
(e) —S(O)$_n$—;
(f)

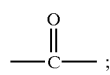

(g) —CR$^2$(OH)—;
(h) —CONR$^2$—;
(i) —NR$^2$CO—;

(j)

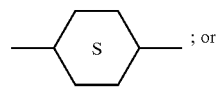

(k) —C≡C—;

R is hydrogen or C$_1$–C$_6$ alkyl;
R$^2$ and R$^3$ are independently
(a) hydrogen; or
(b) C$_1$–C$_4$ alkyl;

R$^4$ is
(a) hydrogen;
(b) halogen;
(c) C$_1$–C$_6$ alkyl;
(d) C$_1$–C$_4$ alkoxy;
(e) C$_1$–C$_4$ acyloxy;
(f) C$_1$–C$_4$ alkylthio;
(g) C$_1$–C$_4$ alkylsulfinyl;
(h) C$_1$–C$_4$ alkylsulfonyl;
(i) hydroxy (C$_1$–C$_4$)alkyl;
(j) aryl (C$_1$–C$_4$)alkyl;
(k) —CO$_2$H;
(l) —CN;
(m) —CONHOR;
(n) —SO$_2$NHR;
(o) —NH$_2$;
(p) C$_1$–C$_4$ alkylamino;
(q) C$_1$–C$_4$ dialkylamino;
(r) —NHSO$_2$R;
(s) —NO$_2$;
(t) —aryl; or
(u) —OH;

R$^5$ and R$^6$ are independently C$_1$–C$_8$ alkyl or together form a C$_3$–C$_{10}$ carbocyclic ring;

R$^7$ and R$^8$ are independently
(a) phenyl;
(b) a C$_3$–C$_{10}$ carbocyclic ring, saturated or unsaturated;
(c) a C$_3$–C$_{10}$ heterocyclic ring containing up to two heteroatoms, selected from —O—, —N— and —S—;
(d) H;
(e) C$_1$–C$_6$ alkyl; or
(f) form a 3 to 8 membered nitrogen containing ring with R$^5$ or R$^6$;

R$^7$ and R$^8$ in either linear or ring form may optionally be substituted with up to three substituents independently selected from C$_1$–C$_6$ alkyl, halogen, alkoxy, hydroxy and carboxy;

a ring formed by R$^7$ and R$^8$ may be optionally fused to a phenyl ring;

e is 0, 1 or 2;
m is 1, 2 or 3;
n is 0, 1 or 2;
p is 0, 1, 2 or 3;
q is 0, 1, 2 or 3;

and optical and geometric isomers thereof; and nontoxic pharmacologically acceptable acid addition salts, N-oxides, esters, quaternary ammonium salts and prodrugs thereof.

Additional preferred compounds of the invention also disclosed in U.S. Pat. No. 5,552,412 are described by the formula designated herein as formula (IA):

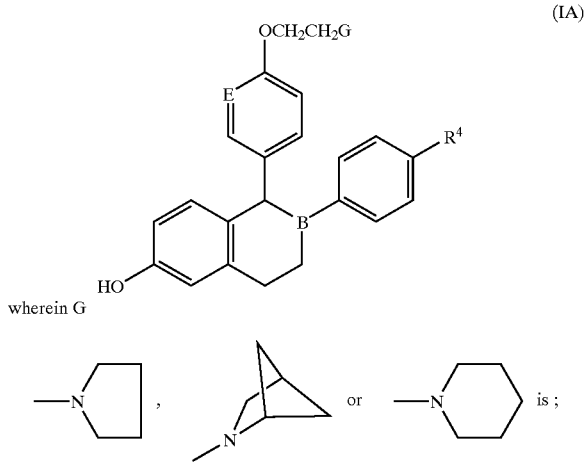

wherein G is;

R⁴ is H, OH, F, or Cl; and B and E are independently selected from CH and N.

Especially preferred compounds for the methods and kits of the invention are:
cis-6-(4-fluoro-phenyl)-5-[4-(2-piperidin-1-yl-ethoxy)-phenyl]-5,6,7,8-tetrahydro-naphthalen-2-ol;
(−)-cis-6-phenyl-5-[4-(2-pyrrolidin-1-yl-ethoxy)-phenyl]-5,6,7,8-tetrahydro-naphthalen-2-ol;
cis-6-phenyl-5-[4-(2-pyrrolidin-1-yl-ethoxy)-phenyl]-5,6,7,8-tetrahydro-naphthalen-2-ol;
cis-1-[6'-pyrrolidinoethoxy-3'-pyridyl]-2-phenyl-6-hydroxy-1,2,3,4-tetrahydronaphthalene;
1-(4'-pyrrolidinoethoxyphenyl)-2-(4"-fluorophenyl)-6-hydroxy-1,2,3,4-tetrahydroisoquinoline;
cis-6-(4-hydroxyphenyl)-5-[4-(2-piperidin-1-yl-ethoxy)-phenyl]-5,6,7,8-tetrahydro-naphthalen-2-ol; and
1-(4'-pyrrolidinoethoxyphenyl)-2-phenyl-6-hydroxy-1,2,3,4-tetrahydroisoquinoline and pharmaceutically acceptable salts thereof. An especially preferred salt of (−)-cis-6-phenyl-5-[4-(2-pyrrolidin-1-yl-ethoxy)-phenyl]-5,6,7,8-tetrahydro-naphthalen-2-ol is the D-tartrate salt.

Other preferred estrogen agonists/antagonists are disclosed in U.S. Pat. 5,047,431. The structure of these compounds are described by the formula designated herein as formula (II) below:

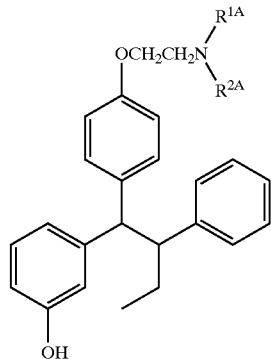

wherein
R¹ᴬ and R²ᴬ may be the same or different and are either H, methyl, ethyl or a benzyl group; and optical or geometric isomers thereof; and pharmaceutically acceptable salts, N-oxides, esters, quaternary ammonium salts, and prodrugs thereof including droloxifene.

Additional preferred estrogen agonists/antagonists are tamoxifen: (ethanamine,2-[-4-(1,2-diphenyl-1-butenyl)phenoxy]-N,N-dimethyl, (Z)-2-, 2-hydroxy-1,2,3-propanetricarboxylate (1:1)) and other compounds as disclosed in U.S. Pat. No. 4,536,516; 4-hydroxy tamoxifen (i.e., tamoxifen wherein the 2-phenyl moiety has a hydroxy group at the 4 position) and other compounds as disclosed in U.S. Pat. No. 4,623,660; raloxifene: (methanone, [6-hydroxy-2-(4-hydroxyphenyl)benzo[b]thien-3-yl][4-[2-(1-piperidinyl)ethoxy]phenyl]-, hydrochloride) and other compounds as disclosed in U.S. Pat. Nos. 4,418,068; 5,393,763; 5,457,117; 5,478,847 and 5,641,790; toremifene: (ethanamine, 2-[4-(4-chloro-1,2-diphenyl-1-butenyl)phenoxy]-N,N-dimethyl-, (Z)-, 2-hydroxy-1,2,3-propanetricarboxylate (1:1) and other compounds as disclosed in U.S. Pat. Nos. 4,696,949 and 4,996,225; centchroman: 1-[2-[[4-(-methoxy-2,2, dimethyl-3-phenyl-chroman4-yl)-phenoxy]-ethyl]-pyrrolidine and other compounds as disclosed in U.S. Pat. No. 3,822,287; idoxifene: pyrrolidine, 1-[-[4-[[1-(4-iodophenyl)-2-phenyl-1-butenyl]phenoxy]ethyl] and other compounds as disclosed in U.S. Pat. No. 4,839,155; 6-(4-hydroxy-phenyl)-5-[4-(2-piperidin-1-yl-ethoxy)-benzyl]-naphthalen-2-ol and other compounds as disclosed in U.S. Pat. Nos. 5,484,795; and {4-[2-(2-aza-bicyclo[2.2.1]hept-2-yl)-ethoxy]-phenyl}-[6-hydroxy-2-(4-hydroxy-phenyl)-benzo[b]thiophen-3-yl]-methanone and other compounds as disclosed in published international patent application WO 95/10513. Other preferred compounds include GW 5638 and GW 7604. The synthesis of these compounds is described in Willson et al., J. Med. Chem., 1994;37:1550–1552.

Further preferred estrogen agonists/antagonists include EM-652 (as shown in the formula designated herein as formula (III) and EM-800 (as shown in the formula designated herein as formula (IV)). The synthesis of EM-652 and EM-800 and the activity of various enantiomers is described in Gauthier et al., J. Med. Chem., 1997;40:2117–2122.

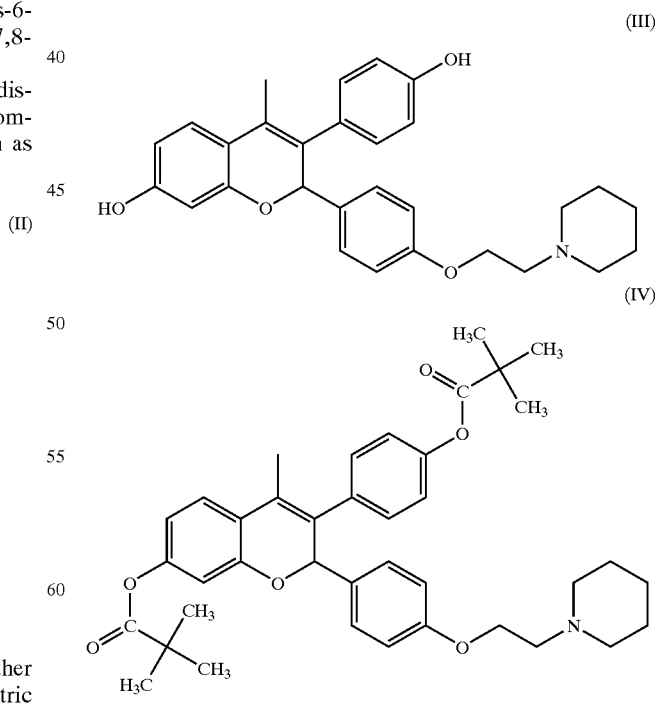

Further preferred estrogen agonists/antagonists include TSE 424 and other compounds disclosed in U.S. Pat. No.

5,998,402, U.S. Pat. No. 5,985,910, U.S. Pat. No. 5,780,497, U.S. Pat. No. 5,880,137, and European Patent Application EP 0802183 A1 including the compounds described by the formulae designated herein as formulae V and VI, below:

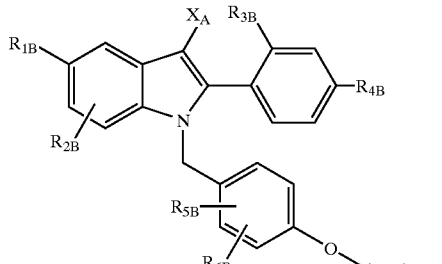

(V)

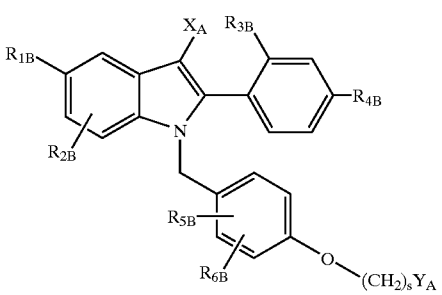

(VI)

wherein:

$R_{1B}$ is selected from H, OH or the $C_1-C_{12}$ esters (straight chain or branched) or $C_1-C_{12}$ (straight chain or branched or cyclic) alkyl ethers thereof, or halogens; or $C_1-C_4$ halogenated ethers including trifluoromethyl ether and trichloromethyl ether.

$R_{2B}$, $R_3B$, $R_{4B}$, $R_{5B}$, and $R_{6B}$ are independently selected from H, OH or the $C_1-C_{12}$ esters (straight chain or branched) or $C_1-C_{12}$ alkyl ethers (straight chain or branched or cyclic) thereof, halogens, or $C_1-C_4$ halogenated ethers including trifluoromethyl ether and trichloromethyl ether, cyano, $C_1-C_6$ alkyl (straight chain or branched), or trifluoromethyl;

$X_A$ is selected from H, $C_1-C_6$ alkyl, cyano, nitro, trifluoromethyl, and halogen;

s is 2 or 3;

$Y_A$ is selected from:

a) the moiety:

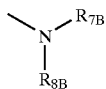

wherein $R_{7B}$ and $R_{8B}$ are independently selected from the group of H, $C_1-C_6$ alkyl, or phenyl optionally substituted by CN, $C_1-C_6$ alkyl (straight chain or branched), $C_1-C_6$ alkoxy (straight chain or branched), halogen, —OH, —CF$_3$, or —OCF$_3$;

b) a five-membered saturated, unsaturated or partially unsaturated heterocycle containing up to two heteroatoms selected from the group consisting of —O—, —NH—, —N($C_1-C_4$ alkyl)-, —N═, and —S(O)$_u$—, wherein u is an integer of from 0–2, optionally substituted with 1–3 substituents independently selected from the group consisting of hydrogen, hydroxyl, halo, $C_1-C_4$ alkyl, trihalomethyl, $C_1-C_4$ alkoxy, trihalomethoxy, $C_1-C_4$ acyloxy, $C_1-C_4$ alkylthio, $C_1-C_4$ alkylsulfinyl, $C_1-C_4$ alkylsulfonyl, hydroxy ($C_1-C_4$)alkyl, —CO$_2$H, —CN, —CONHR$_{1B}$, —NH$_2$, $C_1-C_4$ alkylamino, di($C_1-C_4$)alkylamino, —NHSO$_2$R$_{1B}$, —NHCOR$_{1B}$, —NO$_2$, and phenyl optionally substituted with 1–3 ($C_1-C_4$)alkyl;

c) a six-membered saturated, unsaturated or partially unsaturated heterocycle containing up to two heteroatoms selected from the group consisting of —O—, —NH—, —N($C_1-C_4$ alkyl)-, —N═, and —S(O)$_u$—, wherein u is an integer of from 0–2, optionally substituted with 1–3 substituents independently selected from the group consisting of hydrogen, hydroxyl, halo, $C_1-C_4$ alkyl, trihalomethyl, $C_1-C_4$ alkoxy, trihalomethoxy, $C_1-C_4$ acyloxy, $C_1-C_4$ alkylthio, $C_1-C_4$ alkylsulfinyl, $C_1-C_4$ alkylsulfonyl, hydroxy ($C_1-C_4$)alkyl, —CO$_2$H, —CN, —CONHR$_{1B}$, —NH$_2$, $C_1-C_4$ alkylamino, di($C_1-C_4$)alkylamino, —NHSO$_2$R$_{1B}$, —NHCOR$_{1B}$, —NO$_2$, and phenyl optionally substituted with 1–3 ($C_1-C_4$)alkyl;

d) a seven-membered saturated, unsaturated or partially unsaturated heterocycle containing up to two heteroatoms selected from the group consisting of —O—, —NH—, —N($C_1-C_4$ alkyl)-, —N═, and —S(O)$_u$—, wherein u is an integer of from 0–2, optionally substituted with 1–3 substituents independently selected from the group consisting of hydrogen, hydroxyl, halo, $C_1-C_4$ alkyl, trihalomethyl, $C_1-C_4$ alkoxy, trihalomethoxy, $C_1-C_4$ acyloxy, $C_1-C_4$ alkylthio, $C_1-C_4$ alkylsulfinyl, $C_1-C_4$ alkylsulfonyl, hydroxy ($C_1-C_4$)alkyl, —CO$_2$H, —CN, —CONHR$_{1B}$, —NH$_2$, $C_1-C_4$ alkylamino, di($C_1-C_4$)alkylamino, —NHSO$_2$R$_{1B}$, —NHCOR$_{1B}$, —NO$_2$, and phenyl optionally substituted with 1–3 ($C_1-C_4$)alkyl; or e) a bicyclic heterocycle containing from 6–12 carbon atoms either bridged or fused and containing up to two heteroatoms selected from the group consisting of —O—, —NH—, —N($C_1-C_4$ alkyl)-, and —S(O)$_u$—, wherein u is an integer of from 0–2, optionally substituted with 1–3 substituents independently selected from the group consisting of hydrogen, hydroxyl, halo, $C_1-C_4$ alkyl, trihalomethyl, $C_1-C_4$ alkoxy, trihalomethoxy, $C_1-C_4$ acyloxy, $C_1-C_4$ alkylthio, Cl—$C_4$ alkylsulfinyl, $C_1-C_4$ alkylsulfonyl, hydroxy ($C_1-C_4$)alkyl, —CO$_2$H, —CN, —CONHR$_{1B}$, —NH$_2$, —N═, $C_1-C_4$ alkylamino, di($C_1-C_4$)alkylamino, —NHSO$_2$R$_{1B}$, —NHCOR$_{1B}$, —NO$_2$, and phenyl optionally substituted with 1–3 ($C_1-C_4$) alkyl; and optical and geometric isomers thereof; and nontoxic pharmacologically acceptable acid addition salts, N-oxides, esters, quaternary ammonium salts, and prodrugs thereof.

The more preferred compounds of this invention are those having the general structures V or VI, above, wherein:

$R_{1B}$ is selected from H, OH or the $C_1-C_{12}$ esters or alkyl ethers thereof, and halogen;

$R_{2B}$, $R_{3B}$, $R_{4B}$, $R_{5B}$, and $R_{6B}$ are independently selected from H, OH or the $C_{1-C12}$ esters or alkyl ethers thereof, halogen, cyano, $C_1-C_6$ alkyl, or trihalomethyl, preferably trifluoromethyl, with the proviso that, when $R_{1B}$ is H, $R_{2B}$ is not OH;

$X_A$ is selected from H, $C_1-C_6$ alkyl, cyano, nitro, trifluoromethyl, and halogen;

$Y_A$ is the moiety:

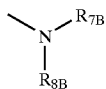

$R_{7B}$ and $R_{8B}$ are selected independently from H, $C_1$–$C_6$ alkyl, or combined by —$(CH_2)_w$—, wherein w is an integer of from 2 to 6, so as to form a ring, the ring being optionally substituted by up to three substituents selected from the group of hydrogen, hydroxyl, halo, $C_1$–$C_4$ alkyl, trihalomethyl, $C_1$–$C_4$ alkoxy, trihalomethoxy, $C_1$–$C_4$ alkylthio, $C_1$–$C_4$ alkylsulfinyl, $C_1$–$C_4$ alkylsulfonyl, hydroxy ($C_1$–$C_4$)alkyl, —$CO_2H$, —CN, —CONH ($C_1$–$C_4$alkyl), —$NH_2$, $C_1$–$C_4$ alkylamino, $C_1$–$C_4$ dialkylamino, —$NHSO_2(C_1$–$C_4$alkyl), —$CO(C_1$–$C_4$alkyl), and —$NO_2$; and optical and geometric isomers thereof; and nontoxic pharmacologically acceptable acid addition salts, N-oxides, esters, quaternary ammonium salts, and prodrugs thereof.

The rings formed by a concatenated $R_{7B}$ and $R_{8B}$, mentioned above, may include, but are not limited to, aziridine, azetidine, pyrrolidine, piperidine, hexamethyleneamine or heptamethyleneamine rings.

The most preferred compounds of structural formulas V and VI, above, are those wherein $R_{1B}$ is OH; $R_{2B}$–$R_{6B}$ are as defined above; $X_A$ is selected from the group of Cl, $NO_2$, CN, $CF_3$, or $CH_3$; $Y_A$ is the moiety

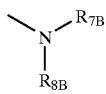

and $R_{7B}$ and $R_{8B}$ are concatenated together as —$(CH_2)_t$—, wherein t is an integer of from 4 to 6, to form a ring optionally substituted by up to three subsituents selected from the group of hydrogen, hydroxyl, halo, $C_1$–$C_4$ alkyl, trihalomethyl, $C_1$–$C_4$ alkoxy, trihalomethoxy, $C_1$–$C_4$ alkylthio, $C_1$–$C_4$ alkylsulfinyl, $C_1$–$C_4$ alkylsulfonyl, hydroxy ($C_1$–$C_4$) alkyl, —$CO_2H$, —CN, —CONH($C_1$–$C_4$) alkyl, —$NH_2$, $C_1$–$C_4$ alkylamino, di($C_1$–$C_4$) alkylamino, —$NHSO_2(C_1$–$C_4$)alkyl, —$NHCO(C_1$–$C_4$)alkyl, and —$NO_2$; and optical and geometric isomers thereof; and nontoxic pharmacologically acceptable acid addition salts, N-oxides, esters, quaternary ammonium salts, and prodrugs thereof. Another preferred compound is TSE-424 as described by the formula designated herein as formula (Va) below:

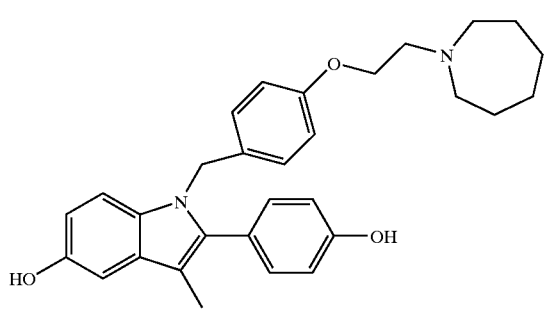

(Va)

The pharmaceutically acceptable acid addition salts of the estrogen agonists/antagonists of this invention may be formed of the compound itself, or of any of its esters, and include the pharmaceutically acceptable salts which are often used in pharmaceutical chemistry. For example, salts may be formed with inorganic or organic acids such as hydrochloric acid, hydrobromic acid, hydroiodic acid, sulfonic acids including such agents as naphthalenesulfonic, methanesulfonic and toluenesulfonic acids, sulfuric acid, nitric acid, phosphoric acid, tartaric acid, pyrosulfuric acid, metaphosphoric acid, succinic acid, formic acid, phthalic acid, lactic acid and the like, most preferable with hydrochloric acid, citric acid, benzoic acid, maleic acid, acetic acid or propionic acid.

The estrogen agonists/antagonists of this invention, as discussed above, can be administered in the form of pharmaceutically acceptable salts. The salts are conveniently formed, as is usual in organic chemistry, by reacting the compound of this invention with a suitable acid, such as has been described above. The salts are quickly formed in high yields at moderate temperatures, and often are prepared by merely isolating the compound from a suitable acidic wash as the final step of the synthesis. The salt-forming acid is dissolved in an appropriate organic solvent, or aqueous organic solvent, such as an alkanol, ketone or ester. On the other hand, if the compound of this invention is desired in the free base form, it is isolated from a basic final wash step, according to the usual practice. A preferred technique for preparing hydrochlorides is to dissolve the free base in a suitable solvent and dry the solution thoroughly, as over molecular sieves, before bubbling hydrogen chloride gas through it. A preferred salt of (–)-cis-6-phenyl-5-[4-(2-pyrrolidin-1-yl-ethoxy)-phenyl]-5,6,7,8-tetrahydronaphthalene-2-ol is the D-(–)-tartrate salt. It will also be recognized that it is possible to administer amorphous forms of the estrogen agonists/antagonists.

The expression "pharmaceutically acceptable salts" includes both pharmaceutically acceptable acid addition salts and pharmaceutically acceptable cationic salts. The expression "pharmaceutically-acceptable cationic salts" is intended to define but is not limited to such salts as the alkali metal salts, (e.g. sodium and potassium), alkaline earth metal salts (e.g., calcium and magnesium), aluminum salts, ammonium salts, and salts with organic amines such as benzathine (N,N'-dibenzylethylenediamine), choline, diethanolamine, ethylenediamine, meglumine (N-methylglucamine), benethamine (N-benzylphenethylamine), diethylamine, piperazine, tromethamine (2-amino-2-hydroxymethyl-1,3-propanediol) and procaine. The expression "pharmaceutically-acceptable acid addition salts" is intended to define but is not limited to such salts as the hydrochloride, hydrobromide, sulfate, hydrogen sulfate, phosphate, hydrogen phosphate, dihydrogenphosphate, acetate, succinate, citrate, methanesulfonate (mesylate) and ptoluenesulfonate (tosylate) salts.

One of ordinary skill in the art will recognize that certain estrogen agonists/antagonists of this invention will contain one or more atoms which may be in a particular stereochemical, tautomeric, or geometric configuration, giving rise to stereoisomers, tautomers and configurational isomers. All such tautomers and isomers and mixtures thereof are included in this invention. Hydrates and solvates of the compounds of this invention are also included.

The subject invention also includes isotopically-labeled estrogen agonists/antagonists, which are structurally identical to those disclosed above, but for the fact that one or more atoms are replaced by an atom having an atomic mass or mass number different from the atomic mass or mass number usually found in nature. Examples of isotopes that can be incorporated into compounds of the invention include isotopes of hydrogen, carbon, nitrogen, oxygen, phosphorous, sulfur, fluorine and chlorine, such as $^2$H, $^3$H, $^{13}$C, $^{14}$C, $^{15}$N, $^{18}$O, $^{17}$O, $^{31}$P, $^{32}$P, $^{35}$S, $^{18}$F and $^{36}$Cl, respectively. Compounds of the present invention, prodrugs thereof, and pharmaceutically acceptable salts of said compounds and of said prodrugs which contain the aforementioned isotopes and/or other isotopes of other atoms are within the scope of this invention. Certain isotopically labeled compounds of the present invention, for example those into which radioactive isotopes such as $^3$H and $^{14}$C are incorporated, are useful in drug and/or substrate tissue distribution assays. Tritiated, i.e., $^3$H, and carbon-14, i.e., $^{14}$C, isotopes are particularly preferred for their ease of preparation and detectability. Further, substitution with heavier isotopes such as deuterium, i.e., $^2$H, may afford certain therapeutic advantages resulting from greater metabolic stability, for example increased in vivo half-life or reduced dosage requirements and, hence, may be preferred in some circumstances. Isotopically labeled compounds of this invention and prodrugs thereof can generally be prepared by carrying out known or referenced procedures and by substituting a readily available isotopically labeled reagent for a non-isotopically labeled reagent.

Those of ordinary skill in the art will recognize that physiologically active compounds which have accessible hydroxy groups can be administered in the form of pharmaceutically acceptable esters. The compounds of this invention can be effectively administered as an ester, formed on the hydroxy groups, just as one skilled in pharmaceutical chemistry would expect. It is possible, as has long been known in pharmaceutical chemistry, to adjust the rate or duration of action of the compound by appropriate choices of ester groups.

Certain ester groups are preferred when a compound of this invention contains an ester. The estrogen agonists/antagonists including the compounds of formula I, IA, II, III, IV, V, Va, or VI may contain ester groups at various positions as defined herein above, where these groups are represented as —COOR$^9$, R$^9$ is $C_1$–$C_{14}$ alkyl, $C_1$–$C_3$ chloroalkyl, $C_1$–$C_3$ fluoroalkyl, $C_5$–$C_7$ cycloalkyl, phenyl, or phenyl mono- or disubstituted with $C_1$–$C_4$ alkyl, $C_1$–$C_4$ alkoxy, hydroxy, nitro, chloro, fluoro or tri(chloro or fluoro)methyl.

As used herein, the term "effective amount" means an amount of compound that is capable of treating the described pathological conditions. The specific dose of a compound administered according to this invention will, of course, be determined by the particular circumstances surrounding the case including, for example, the compound administered, the route of administration, the state of being of the patient, and the severity of the pathological condition being treated.

The dose of a compound of this invention to be administered to a subject is rather widely variable and subject to the judgement of the attending physician. It should be noted that it may be necessary to adjust the dose of a compound when it is administered in the form of a salt, such as a laureate, the salt forming moiety of which has an appreciable molecular weight.

The following dosage amounts and other dosage amounts set forth elsewhere in this description and in the appendant claims are for an average human subject having a weight of about 65 kg to about 70 kg. The skilled practitioner will readily be able to determine the dosage amount required for a subject whose weight falls outside the 65 kg to 70 kg range, based upon the medical history of the subject. All doses set forth herein, and in the appendant claims, are daily doses of the free base form of the estrogen agonists/antagonists. Calculation of the dosage amount for other forms of the free base form such as salts or hydrates is easily accomplished by performing a simple ratio relative to the molecular weights of the species involved.

The general range of effective administration rates of the estrogen agonists/antagonists is from about 0.001 mg/day to about 200 mg/day. A preferred rate range is from about 0.010 mg/day to about 100 mg/day. Of course, it is often practical to administer the daily dose of compound in portions, at various hours of the day. However, in any given case, the amount of compound administered will depend on such factors as the potency of the specific estrogen agonist/antagonist, the solubility of the compound, the formulation used and the route of administration.

Methods of formulation are well known in the art and are disclosed, for example, in *Remington's Pharmaceutical Sciences,* Mack Publishing Company, Easton, Pa., 19th Edition (1995). Pharmaceutical compositions for use within the present invention can be in the form of sterile, non-pyrogenic liquid solutions or suspensions, coated capsules, suppositories, lyophilized powders, transdermal patches or other forms known in the art.

Capsules are prepared by mixing the compound with a suitable diluent and filling the proper amount of the mixture in capsules. The usual diluents include inert powdered substances such as starch of many different kinds, powdered cellulose, especially crystalline and microcrystalline cellulose, sugars such as fructose, mannitol and sucrose, grain flours and similar edible powders.

Tablets are prepared by direct compression, by wet granulation, or by dry granulation. Their formulations usually incorporate diluents, binders, lubricants and disintegrators as well as the compound. Typical diluents include, for example, various types of starch, lactose, mannitol, kaolin, calcium phosphate or sulfate, inorganic salts such as sodium chloride and powdered sugar. Powdered cellulose derivatives are also useful. Typical tablet binders are substances such as starch, gelatin and sugars such as lactose, fructose, glucose and the like. Natural and synthetic gums are also convenient, including acacia, alginates, methylcellulose, polyvinylpyrrolidine and the like. Polyethylene glycol, ethylcellulose and waxes can also serve as binders.

A lubricant may be necessary in a tablet formulation to prevent the tablet and punches from sticking in the die. The lubricant is chosen from such slippery solids as talc, magnesium and calcium stearate, stearic acid and hydrogenated vegetable oils.

Tablet disintegrators are substances which facilitate the disintegration of a tablet to release a compound when the tablet becomes wet. They include starches, clays, celluloses, algins and gums, more particularly, corn and potato starches, methylcellulose, agar, bentonite, wood cellulose, powdered natural sponge, cation-exchange resins, alginic acid, guar gum, citrus pulp and carboxymethylcellulose, for example, may be used as well as sodium lauryl sulfate.

Tablets are often coated with sugar as a flavorant and sealant, or with film-forming protecting agents to modify the dissolution properties of the tablet. The compounds may also be formulated as chewable tablets, by using large amounts of pleasant-tasting substances such as mannitol in the formulation, as is now well-established in the art.

When it is desired to administer a compound as a suppository, the typical bases may be used. Cocoa butter is a traditional suppository base, which may be modified by addition of waxes to raise its melting point slightly. Water-miscible suppository bases comprising, particularly, polyethylene glycols of various molecular weights are in wide use.

The effect of the compounds may be delayed or prolonged by proper formulation. For example, a slowly soluble pellet of the compound may be prepared and incorporated in a tablet or capsule. The technique may be improved by making pellets of several different dissolution rates and filling capsules with a mixture of the pellets. Tablets or capsules may be coated with a film which resists dissolution for a predictable period of time. Topical formulations may be designed to yield delayed and/or prolonged percutaneous absorption of a compound. Even the parenteral preparations may be made long-acting, by dissolving or suspending the compound in oily or emulsified vehicles which allow it to disperse only slowly in the serum.

The term "prodrug" means a compound that is transformed in vivo to yield a compound of the present invention. The transformation may occur by various mechanisms, such as through hydrolysis in blood. A discussion of the use of prodrugs is provided by T. Higuchi and W. Stella, "Prodrugs as Novel Delivery Systems," Vol. 14 of the *A.C.S. Symposium Series*, and in *Bioreversible Carriers in Drug Design*, ed. Edward B. Roche, American Pharmaceutical Association and Pergamon Press, 1987.

For example, if a compound of the present invention contains a carboxylic acid functional group, a prodrug can comprise an ester formed by the replacement of the hydrogen atom of the acid group with a group such as ($C_1$–$C_8$) alkyl, ($C_2$–$C_{12}$) alkanoyloxymethyl, 1-(alkanoyloxy)ethyl having from 4 to 9 carbon atoms, 1-methyl-1-(alkanoyloxy)-ethyl having from 5 to 10 carbon atoms, alkoxycarbonyloxymethyl having from 3 to 6 carbon atoms, 1-(alkoxycarbonyloxy)ethyl having from 4 to 7 carbon atoms, 1-methyl-1-(alkoxycarbonyloxy)ethyl having from 5 to 8 carbon atoms, N-(alkoxycarbonyl)aminomethyl having from 3 to 9 carbon atoms, 1-(N-(alkoxycarbonyl)amino) ethyl having from 4 to 10 carbon atoms, 3-phthalidyl, 4-crotonolactonyl, gamma-butyrolacton-4-yl, di-N,N—($C_1$–$C_2$)alkylamino($C_2$–$C_3$)alkyl (such as β-dimethylaminoethyl), carbamoyl-($C_1$–$C_2$)alkyl, N,N-di ($C_1$–$C_2$)alkylcarbamoyl-($C_1$–$C_2$)alkyl and piperidino-, pyrrolidino- or morpholino($C_2$–$C_3$)alkyl.

Similarly, if a compound of the present invention comprises an alcohol functional group, a prodrug can be formed by the replacement of the hydrogen atom of the alcohol group with a group such as ($C_1$–$C_6$)alkanoyloxymethyl, 1—(($C_1$–$C_6$)alkanoyloxy)ethyl, 1-methyl-1-(($C_1$–$C_6$) alkanoyloxy)ethyl, ($C_1$–$C_6$)alkoxycarbonyloxymethyl, N—($C_1$–$C_6$)alkoxycarbonylaminomethyl, succinoyl, ($C_1$–$C_6$)alkanoyl, α-amino($C_1$–$C_4$)alkanoyl, arylacyl and α-aminoacyl, or α-aminoacyl-α-aminoacyl, where each α-aminoacyl group is independently selected from the naturally occurring L-amino acids, $P(O)(OH)_2$, —$P(O)(O$($C_1$–$C_6$)alkyl$)_2$ or glycosyl (the radical resulting from the removal of a hydroxyl group of the hemiacetal form of a carbohydrate).

If a compound of the present invention comprises an amine functional group, a prodrug can be formed by the replacement of a hydrogen atom in the amine group with a group such as $R^X$-carbonyl, $R^X$O-carbonyl, $NR^X R^{X_1}$-carbonyl where $R^X$ and $R^{X_1}$ are each independently ($C_1$–$C_{10}$) alkyl, ($C_3$–$C_7$)cycloalkyl, benzyl, or $R^X$-carbonyl is a natural α-aminoacyl or natural α-aminoacyl-natural α-aminoacyl, —C(OH)C(O)$OY^X$ wherein $Y^{X1}$ is H, ($C_1$–$C_6$)alkyl or benzyl, —C($OY^{X0}$) $Y^{X1}$ wherein $Y^{X0}$ is ($C_1$–$C_4$) alkyl and $Y^{X1}$ is ($C_1$–$C_6$)alkyl, carboxy($C_1$–$C_6$)alkyl, amino($C_1$–$C_4$) alkyl or mono-N- or di-N,N-($C_1$–$C_6$)alkylaminoalkyl, —C($Y^{X2}$) $Y^{X3}$ wherein $Y^{X2}$ is H or methyl and $Y^{X3}$ is mono-N- or di-N,N-($C_1$–$C_6$)alkylamino, morpholino, piperidin-1-yl or pyrrolidin-1-yl.

Advantageously, the present invention also provides kits for use by a consumer to prevent myocardial infarction or stroke; maintain or improve vascular reactivity; treat acute or chronic renal failure, peripheral arterial occlusive disease, coronary artery disease, or Raynaud's phenomenon; or lower plasma levels of Lp(a). The kits comprise a) a pharmaceutical composition comprising an estrogen agonist/antagonist and a pharmaceutically acceptable carrier, vehicle or diluent; and b) instructions describing a method of using the pharmaceutical compositions to prevent myocardial infarction or stroke; maintain or improve vascular reactivity; treat acute or chronic renal failure, peripheral arterial occlusive disease, coronary artery disease, or Raynaud's phenomenon; or lower plasma levels of Lp(a). The instructions may also indicate that the kit is to improve or maintain vascular health and/or lower serum lipoprotein (a) levels while substantially reducing the concomitant liability of adverse effects associated with estrogen administration.

A "kit" as used in the instant application includes a container for containing the pharmaceutical compositions and may also include divided containers such as a divided bottle or a divided foil packet. The container can be in any conventional shape or form as known in the art which is made of a pharmaceutically acceptable material, for example a paper or cardboard box, a glass or plastic bottle or jar, a re-sealable bag (for example, to hold a "refill" of tablets for placement into a different container), or a blister pack with individual doses for pressing out of the pack according to a therapeutic schedule. The container employed can depend on the exact dosage form involved, for example a conventional cardboard box would not generally be used to hold a liquid suspension. It is feasible that more than one container can be used together in a single package to market a single dosage form. For example, tablets may be contained in a bottle, which is in turn contained within a box.

An example of such a kit is a so-called blister pack. Blister packs are well known in the packaging industry and are being widely used for the packaging of pharmaceutical unit dosage forms (tablets, capsules, and the like). Blister packs generally consist of a sheet of relatively stiff material covered with a foil of a preferably transparent plastic material. During the packaging process, recesses are formed in the plastic foil. The recesses have the size and shape of individual tablets or capsules to be packed or may have the size and shape to accommodate multiple tablets and/or capsules to be packed. Next, the tablets or capsules are placed in the recesses accordingly and the sheet of relatively stiff material is sealed against the plastic foil at the face of the foil which is opposite from the direction in which the recesses were formed. As a result, the tablets or capsules are individually sealed or collectively sealed, as desired, in the recesses between the plastic foil and the sheet. Preferably the strength of the sheet is such that the tablets or capsules can be removed from the blister pack by manually applying pressure on the recesses whereby an opening is formed in the sheet at the place of the recess. The tablet or capsule can then be removed via said opening.

It may be desirable to provide a written memory aid, where the written memory aid is of the type containing information and/or instructions for the physician, pharmacist or subject, e.g., in the form of numbers next to the tablets or capsules whereby the numbers correspond with the days of the regimen which the tablets or capsules so specified should be ingested or a card which contains the same type of information. Another example of such a memory aid is a calendar printed on the card e.g., as follows "First Week, Monday, Tuesday," . . . etc . . . . "Second Week, Monday, Tuesday, . . . " etc. Other variations of memory aids will be readily apparent. A "daily dose" can be a single tablet or capsule or several tablets or capsules to be taken on a given day.

Another specific embodiment of a kit is a dispenser designed to dispense the daily doses one at a time. Preferably, the dispenser is equipped with a memory-aid, so as to further facilitate compliance with the regimen. An example of such a memory-aid is a mechanical counter which indicates the number of daily doses that has been dispensed. Another example of such a memory-aid is a battery-powered micro-chip memory coupled with a liquid crystal readout, or audible reminder signal which, for example, reads out the date that the last daily dose has been taken and/or reminds one when the next dose is to be taken.

The kits and methods of the present invention may also include, in addition to an estrogen agonist/antagonist, one or more additional pharmaceutically active compounds. Preferably, any additional compound is an estrogen agonist/ antagonist or another compound that is useful to prevent myocardial infarction or stroke; maintain or improving vascular reactivity; or treat acute or chronic renal failure, peripheral arterial occlusive disease, coronary artery disease, or Raynaud's phenomenon. Moreover, the additional compound can also be another compound that lowers the plasma concentration of Lp(a) in a patient. Compounds that are used to treat stroke include anticoagulants such as heparin and antiplatelet drugs such as aspirin and ticlopidine.

In addition, an estrogen agonist/antagonist can be administered in combination with other pharmaceutical agents such as cholesterol biosynthesis inhibitors and cholesterol absorption inhibitors, especially HMG-CoA reductase inhibitors and HMG-CoA synthase inhibitors, HMG-CoA reductase and synthase gene expression inhibitors, CETP inhibitors, biles acid sequesterants, fibrates, ACAT inhibitors, squalene synthetase inhibitors, anti-oxidants and niacin. The estrogen agonists/antagonists of the present invention may also be administered in combination with naturally occurring compounds that act to lower plasma cholesterol levels. These naturally occurring compounds are commonly called nutraceuticals and include, for example, garlic extract, Benecol®, and niacin.

Specific cholesterol absorption inhibitors and cholesterol biosynthesis inhibitors are described in detail below. Additional cholesterol absorption inhibitors are known to those skilled in the art and are described, for example, in PCT WO 94/00480.

Any HMG-CoA reductase inhibitor may be employed as an additional compound in the combination therapy aspect of the present invention. The term HMG-CoA reductase inhibitor refers to a compound that inhibits the biosynthesis of hydroxymethylglutaryl-coenzyme A to mevalonic acid as catalyzed by the enzyme HMG-CoA reductase. Such inhibition may be determined readily by one of skill in the art according to standard assays (e.g., Methods of Enzymology, 71: 455–509 (1981); and the references cited therein). A variety of these compounds are described and referenced below. U.S. Pat. No. 4,231,938 discloses certain compounds isolated after cultivation of a microorganism belonging to the genus Aspergillus, such as lovastatin. Also, U.S. Pat. No. 4,444,784 discloses synthetic derivatives of the aforementioned compounds, such as simvastatin. Additionally, U.S. Pat. No. 4,739,073 discloses certain substituted indoles, such as fluvastatin. Further, U.S. Pat. No. 4,346,227 discloses ML-236B derivatives, such as pravastatin. In addition, EP 491,226 teaches certain pyridyldihydroxyheptenoic acids, such as rivastatin. Also, U.S. Pat. No. 4,647, 576 discloses certain 6-[2-(substituted-pyrrol-1-yl)-alkyl]-pyran-2-ones such as atorvastatin. Other HMG-CoA reductase inhibitors will be known to those skilled in the art. Examples of marketed products containing HMG-CoA reductase inhibitors that can be used in combination with compounds of the presnet invention include Baycol®, Lescol®, Lipitor®, Mevacor®, Pravachol® and Zocor®.

Any HMG-CoA synthase inhibitor may be used as the second compound in the combination therapy aspect of this invention. The term HMG-CoA synthase inhibitor refers to a compound which inhibits the biosynthesis of hydroxymethylglutaryl-coenzyme A from acetyl-coenzyme A and acetoacetyl-coenzyme A, catalyzed by the enzyme HMG-CoA synthase. Such inhibition may be determined readily by one of skill in the art according to standard assays (e.g., Methods of Enzymology, 35:155–160 (1975); and Methods of Enzymology, 110: 19–26 (1985); and the references cited therein). A variety of these compounds are described and referenced below. U.S. Pat. No. 5,120,729 discloses certain beta-lactam derivatives. U.S. Pat. No. 5,064,856 discloses certain spiro-lactone derivatives prepared by culturing the microorganism MF5253. U.S. Pat. No. 4,847,271 discloses certain oxetane compounds such as 11-(3-hydroxymethyl-4-oxo-2-oxetayl)-3,5,7-trimethyl-2,4-undecadienoic acid derivatives. Other HMG-CoA synthase inhibitors will be known to those skilled in the art.

Any compound that decreases HMG-CoA reductase gene expression may be used as the second compound in the combination therapy aspect of this invention. These agents may be HMG-CoA reductase transcription inhibitors that block the transcription of DNA or translation inhibitors that prevent translation of mRNA coding for HMG-CoA reductase into protein. Such inhibitors may either affect transcription or translation directly, or may be biotransformed into compounds that have the aforementioned attributes by one or more enzymes in the cholesterol biosynthetic cascade or may lead to the accumulation of an isoprene metabolite that has the aforementioned activities. Such regulation is readily determined by those skilled in the art according to standard assays (Methods of Enzymology, 110: 9–19 1985). Several such compounds are described and referenced below however other inhibitors of HMG-CoA reductase gene expression will be known to those skilled in the art. U.S. Pat. No. 5,041,432 discloses certain 15-substituted lanosterol derivatives. Other oxygenated sterols that suppress the biosynthesis of HMG-CoA reductase are discussed by E. I. Mercer (Prog. Lip. Res., 32:357–416 1993).

Any compound having activity as a CETP inhibitor can serve as the second compound in the combination therapy aspect of the instant invention.

The term CETP inhibitor refers to compounds that inhibit the cholesteryl ester transfer protein (CETP) mediated transport of various cholesteryl esters and triglycerides from HDL to LDL and VLDL. A variety of these compounds are described and referenced below however other CETP inhibitors will be known to those skilled in the art. U.S. Pat. No. 5,512,548 discloses certain polypeptide derivatives having activity as CETP inhibitors, while certain CETP-inhibitory rosenonolactone derivatives and phosphate-containing analogs of cholesteryl ester are disclosed in J. Antibiot., 49(8): 815–816 (1996), and Bioorg. Med. Chem. Lett.; 6:1951–1954 (1996), respectively. Other CETP inhibitors that can be used in combination with compounds of the present invention are disclosed in WO 99/20302, EP 796846, EP818197, EP 818448, WO 99/14204, WO 99/41237, WO 95/04755, WO 96/15141, WO 96/05227, DE 19704244, DE19741051, DE 19741399, DE 19704243, DE 19709125, DE 19627430, DE 19832159, DE 19741400, JP 11049743, and JP 09059155. Preferred CETP inhibitors that can be used in combination with the compounds of the present invention include

[2R,4S] 4-[(3,5-bis-trifluoromethyl-benzyl)-methoxycarbonyl-amino]-2-ethyl-6-trifluoromethyl-3,4-dihydro-2H-quinoline-1-carboxylic acid isopropyl ester;

[2S,4S] 4-[(3,5-bis-trifluoromethyl-benzyl)-methoxycarbonyl-amino]-2-methoxymethyl-6-trifluoromethyl-3,4-dihydro-2H-quinoline-1-carboxylic acid isopropyl ester;

[2R,4S] 4-[(3,5-bis-trifluoromethyl-benzyl)-methoxycarbonyl-amino]-2-ethyl-6-trifluoromethyl-3,4-dihydro-2H-quinoline-1-carboxylic acid 2-hydroxy-ethyl ester;

[2S,4S] 4-[(3,5-bis-trifluoromethyl-benzyl)-methoxycarbonyl-amino]-2-cyclopropyl-6-trifluoromethyl-3,4-dihydro-2H-quinoline-1-carboxylic acid ethyl ester;

[2R,4S] 4-[(3,5-bis-trifluoromethyl-benzyl)-methoxycarbonyl-amino]-2-ethyl-6-trifluoromethyl-3,4-dihydro-2H-quinoline-1-carboxylic acid ethyl ester;

[2S,4S] 4-[(3,5-bis-trifluoromethyl-benzyl)-methoxycarbonyl-amino]-2-cyclopropyl-6-trifluoromethyl-3,4-dihydro-2H-quinoline-1-carboxylic acid propyl ester; and

[2R,4S] 4-[(3,5-bis-trifluoromethyl-benzyl)-methoxycarbonyl-amino]-2-ethyl-6-trifluoromethyl-3,4-dihydro-2H-quinoline-1-carboxylic acid propyl ester,

[2S,4S] 4-[(3,5-bis-trifluoromethyl-benzyl)-methoxycarbonyl-amino]-2-isopropyl-6-trifluoromethyl-3,4-dihydro-2H-quinoline-1-carboxylic acid isopropyl ester;

[2S,4S] 4-[(3,5-bis-trifluoromethyl-benzyl)-methoxycarbonyl-amino]-6-chloro-2-cyclopropyl-3,4-dihydro-2H-quinoline-1-carboxylic acid isopropyl ester;

[2S,4S] 2-cyclopropyl4-[(3,5-dichloro-benzyl)-methoxycarbonyl-amino]-6-trifluoromethyl-3,4-dihydro-2H-quinoline-1-carboxylic acid isopropyl ester;

[2S,4S] 4-[(3,5-bis-trifluoromethyl-benzyl)-methoxycarbonyl-amino]-2-cyclopropyl-6-trifluoromethyl-3,4-dihydro-2H-quinoline-1-carboxylic acid tert-butyl ester;

[2S,4S] 4-[(3,5-bis-trifluoromethyl-benzyl)-methoxycarbonyl-amino]-2-cyclopropyl-6-trifluoromethyl-3,4-dihydro-2H-quinoline-1-carboxylic acid isopropyl ester;

[2S,4S] 4-[(3,5-bis-trifluoromethyl-benzyl)-methoxycarbonyl-amino]-2-cyclobutyl-6-trifluoromethyl-3,4-dihydro-2H-quinoline-1-carboxylic acid isopropyl ester;

[2R,4S] 4-[(3,5-bis-trifluoromethyl-benzyl)-methoxycarbonyl-amino]-2-ethyl-6-trifluoromethyl-3,4-dihydro-2H-quinoline-1-carboxylic acid isopropyl ester;

[2S,4S] 4-[(3,5-bis-trifluoromethyl-benzyl)-methoxycarbonyl-amino]-2-methoxymethyl-6-trifluoromethyl-3,4-dihydro-2H-quinoline-1-carboxylic acid isopropyl ester;

[2R,4S] 4-[(3,5-bis-trifluoromethyl-benzyl)-methoxycarbonyl-amino]-2-ethyl-6-trifluoromethyl-3,4-dihydro-2H-quinoline-1-carboxylic acid 2-hydroxy-ethyl ester;

[2S,4S] 4-[(3,5-bis-trifluoromethyl-benzyl)-methoxycarbonyl-amino]-2-cyclopropyl-6-trifluoromethyl-3,4-dihydro-2H-quinoline-1-carboxylic acid ethyl ester;

[2R,4S] 4-[(3,5-bis-trifluoromethyl-benzyl)-methoxycarbonyl-amino]-2-ethyl-6-trifluoromethyl-3,4-dihydro-2H-quinoline-1-carboxylic acid ethyl ester;

[2S,4S] 4-[(3,5-bis-trifluoromethyl-benzyl)-methoxycarbonyl-amino]-2-cyclopropyl-6-trifluoromethyl-3,4-dihydro-2H-quinoline-1-carboxylic acid propyl ester; and

[2R,4S] 4-[(3,5-bis-trifluoromethyl-benzyl)-methoxycarbonyl-amino]-2-ethyl-6-trifluoromethyl-3,4-dihydro-2H-quinoline-1-carboxylic acid propyl ester, and pharmaceutically acceptable salts and prodrugs thereof and salts of the prodrugs.

Any ACAT inhibitor can serve as the second compound in the combination therapy aspect of this invention. The term ACAT inhibitor refers to compounds that inhibit the intracellular esterification of dietary cholesterol by the enzyme acyl CoA: cholesterol acyltransferase. Such inhibition may be determined readily by one of skill in the art according to standard assays, such as the method of Heider et al. described in *Journal of Lipid Research.*, 24:1127 (1983). A variety of these compounds are described and referenced below; however, other ACAT inhibitors will be known to those skilled in the art. U.S. Pat. No. 5,510,379 discloses certain carboxysulfonates, while WO 96/26948 and WO 96/10559 both disclose urea derivatives having ACAT inhibitory activity.

Any compound having activity as a squalene synthetase inhibitor can serve as an additional compound in the combination therapy aspect of the instant invention. The term squalene synthetase inhibitor refers to compounds that inhibit the condensation of two molecules of farnesylpyrophosphate to form squalene, a reaction that is catalyzed by the enzyme squalene synthetase. Such inhibition is readily determined by those skilled in the art according to standard methodology (*Methods of Enzymology,* 15:393–454 (1969); and *Methods of Enzymology,* 110: 359–373 (1985); and references cited therein). A summary of squalene synthetase inhibitors has been complied in *Curr. Op. Ther. Patents,* 861–4, (1993). European patent application publication Number 0 567 026 A1 discloses certain 4,1-benzoxazepine derivatives as squalene synthetase inhibitors and their use in the treatment of hypercholesterolemia and as fungicides. European patent application publication Number 0 645 378 A1 discloses certain seven- or eight-membered heterocycles as squalene synthetase inhibitors and their use in the treatment and prevention hypercholesterolemia and fungal infections. European patent application publication Number 0 645 377 A1 discloses certain benzoxazepine derivatives as squalene synthetase inhibitors useful for the treatment of hypercholesterolemia or coronary sclerosis. European patent application publication Number 0 611 749 A1 discloses certain substituted amic acid derivatives useful for the treatment of arteriosclerosis. European patent application publication Number 0 705 607 A2 discloses certain condensed seven- or eight-membered heterocyclic compounds useful as antihypertriglyceridemic agents. PCT publication WO 96/09827 discloses certain combinations of cholesterol absorption inhibitors and cholesterol biosynthesis inhibitors including benzoxazepine derivatives and benzothiazepine derivatives. European patent application publication Number 0 701 725 A1 discloses a process for preparing certain optically-active compounds, including benzoxazepine derivatives, having plasma cholesterol and triglyceride lowering activities. Other compounds that are marketed for hyperlipidemia, including hypercholesterolemia and which are intended to help prevent or treat atherosclerosis include bile acid sequestrants, such as Colestid® and LoCholest® and Questran®; and fibric acid derivatives, such as Atromid®, Lopid® and Tricor®. These compounds can also be used in combination with a compound of the present invention.

It is also contemplated that the compounds of the present invention be administered with a lipase inhibitor and/or a glucosidase inhibitor, which are typically used in the treatment of conditions resulting from the presence of excess triglycerides, free fatty acids, cholesterol, cholesterol esters or glucose including, inter alia, obesity, hyperlipidemia, hyperlipoproteinemia, Syndrome X, and the like.

In a combination with a compound of the present invention, any lipase inhibitor or glucosidase inhibitor may be employed. Preferred lipase inhibitors comprise gastric or pancreatic lipase inhibitors such as orlistat. Preferred glucosidase inhibitors comprise amylase inhibitors.

A lipase inhibitor is a compound that inhibits the metabolic cleavage of dietary triglycerides into free fatty acids and monoglycerides. Under normal physiological conditions, lipolysis occurs via a two-step process that involves acylation of an activated serine moiety of the lipase enzyme. This leads to the production of a fatty acid-lipase hemiacetal intermediate, which is then cleaved to release a diglyceride. Following further deacylation, the lipase-fatty acid intermediate is cleaved, resulting in free lipase, a monoglyceride and a fatty acid. The resultant free fatty acids and monoglycerides are incorporated into bile acid-phospholipid micelles, which are subsequently absorbed at the level of the brush border of the small intestine. The micelles eventually enter the peripheral circulation as chylomicrons. Accordingly, compounds, including lipase inhibitors that selectively limit or inhibit the absorption of ingested fat precursors are useful in the treatment of conditions including obesity, hyperlipidemia, hyperlipoproteinemia, Syndrome X, and the like.

Pancreatic lipase mediates the metabolic cleavage of fatty acids from triglycerides at the 1- and 3-carbon positions. The primary site of the metabolism of ingested fats is in the duodenum and proximal jejunum by pancreatic lipase, which is usually secreted in vast excess of the amounts necessary for the breakdown of fats in the upper small intestine. Because pancreatic lipase is the primary enzyme required for the absorption of dietary triglycerides, inhibitors have utility in the treatment of obesity and the other related conditions.

Gastric lipase is an immunologically distinct lipase that is responsible for approximately 10 to 40% of the digestion of dietary fats. Gastric lipase is secreted in response to mechanical stimulation, ingestion of food, the presence of a fatty meal or by sympathetic agents. Gastric lipolysis of ingested fats is of physiological importance in the provision of fatty acids needed to trigger pancreatic lipase activity in the intestine and is also of importance for fat absorption in a variety of physiological and pathological conditions associated with pancreatic insufficiency. See, for example, C. K. Abrams, et al., *Gastroenterology*, 92, 125 (1987).

A variety of lipase inhibitors are known to one of ordinary skill in the art. However, in the practice of the methods, pharmaceutical compositions and kits of the instant invention, generally preferred lipase inhibitors are those inhibitors that are selected from the group consisting of lipstatin, tetrahydrolipstatin (orlistat), FL-386, WAY-121898, Bay-N-3176, valilactone, esterastin, ebelactone A, ebelactone B and RHC 80267.

The pancreatic lipase inhibitors lipstatin, 2S, 3S, 5S, 10Z)-5-[(S)-2-formamido-4-methyl-valeryloxy]-2-hexyl-3-hydroxy-7,10-hexadecanoic acid lactone, and tetrahydrolipstatin (orlistat), 2S, 3S, 5S)-5-[(S)-2-formamido-4-methyl-valeryloxy]-2-hexyl-3-hydroxy-hexadecanoic acid lactone, and the variously substituted N-formyllecunie derivatives and stereoisomers thereof, are disclosed in U.S. Pat. No. 4,598,089.

The pancreatic lipase inhibitor FL-386, 1-[4-(2-methylpropyl)cyclohexyl]-2-[(phenylsulfonyl)oxy]-ethanone, and the variously substituted sulfonate derivatives related thereto, are disclosed in U.S. Pat. No. 4,452,813.

The pancreatic lipase inhibitor WAY-121898, 4-phenoxyphenyl-4-methylpiperidin-1-yl-carboxylate, and the various carbamate esters and pharmaceutically acceptable salts related thereto, are disclosed in U.S. Pat. Nos. 5,512,565; 5,391,571 and 5,602,151.

The lipase inhibitor Bay-N-3176, N-3-trifluoromethylphenyl-N'-3-chloro-4'-trifluoromethylphenylurea, and the various urea derivatives related thereto, are disclosed in U.S. Pat. No. 4,405,644.

The pancreatic lipase inhibitor valilactone, and a process for the preparation thereof by the microbial cultivation of Actinomycetes strain MG147–CF2, are disclosed in Kitahara, et al., *J. Antibiotics*, 40 (11), 1647–1650 (1987).

The lipase inhibitor esteracin, and certain processes for the preparation thereof by the microbial cultivation of Streptomyces strain ATCC 31336, are disclosed in U.S. Pat. Nos. 4,189,438 and 4,242,453.

The pancreatic lipase inhibitors ebelactone A and ebelactone B, and a process for the preparation thereof by the microbial cultivation of Actinomycetes strain MG7-G1, are disclosed in Umezawa, et al., *J Antibiotics*, 33, 1594–1596 (1980). The use of ebelactones A and B in the suppression of monoglyceride formation is disclosed in Japanese Kokai 08–143457, published Jun. 4, 1996.

The lipase inhibitor RHC 80267, cyclo-O,O'-[(1,6-hexanediyl)-bis-(iminocarbonyl)]dioxime, and the various bis(iminocarbonyl)dioximes related thereto may be prepared as described in Petersen et al., *Liebig's Annalen*, 562, 205–229 (1949). The ability of RHC 80267 to inhibit the activity of myocardial lipoprotein lipase is disclosed in Carroll et al., *Lipids*, 27, pp. 305–307 (1992) and Chuang et al., *J. Mol. Cell Cardiol.*, 22, 1009–1016 (1990).

A glucosidase inhibitor inhibits the enzymatic hydrolysis of complex carbohydrates by glycoside hydrolases, for example amylase or maltase, into bioavailable simple sugars, for example, glucose. The rapid metabolic action of glucosidases, particularly following the intake of high levels of carbohydrates, results in a state of alimentary hyperglycemia which, in adipose or diabetic subjects, leads to enhanced secretion of insulin, increased fat synthesis and a reduction in fat degradation. Following such hyperglycemias, hypoglycemia frequently occurs, due to the augmented levels of insulin present. Additionally, it is known that both hypoglycemias and chyme remaining in the stomach promotes the production of gastric juice which initiates or favors the development of gastritis or duodenal ulcers. Accordingly, glucosidase inhibitors are known to have utility in accelerating the passage of carbohydrates through the stomach and inhibiting the absorption of glucose from the intestine. Furthermore, the conversion of carbohydrates into lipids of the fatty tissue and the subsequent incorporation of alimentary fat into fatty tissue deposits is accordingly reduced or delayed, with the concomitant benefit of reducing or preventing the deleterious abnormalities resulting therefrom.

In combination with a compound of the present invention, any glucosidase inhibitor may be employed, however, a generally preferred glucosidase inhibitor comprises an amylase inhibitor. An amylase inhibitor is a glucosidase inhibitor that inhibits the enzymatic degradation of starch or glycogen into maltose. The inhibition of such enzymatic degradation is beneficial in reducing amounts of bioavailable sugars, including glucose and maltose, and the concomitant deleterious conditions resulting therefrom.

A variety of glucosidase and amylase inhibitors are known to one of ordinary skill in the art. However, in the practice of the methods and pharmaceutical compositions of the instant invention, generally preferred glucosidase inhibitors are those inhibitors that are selected from the group consisting of acarbose, adiposine, voglibose, miglitol, emiglitate, MDL-25637, camiglibose, tendamistate, AI-3688, trestatin, pradimicin-Q and salbostatin.

The glucosidase inhibitor acarbose, O-4,6-dideoxy-4-[[(1S,4R,5S,6S)-4,5,6-trihydroxy-3-(hydroxymethyl)-2-cyclohexen-1-yl]amino]-α-glucopyranosyl-(1 →>4)-O-α-D-glucopyranosyl-(1 →>4)-D-glucose, the various amino sugar derivatives related thereto and a process for the preparation thereof by the microbial cultivation of Actinoplanes strains SE 50 (CBS 961.70), SB 18 (CBS 957.70), SE 82 (CBS 615.71), SE 50/13 (614.71) and SE 50/110 (674.73) are disclosed in U.S. Pat. Nos. 4,062,950 and 4,174,439 respectively.

The glucosidase inhibitor adiposine, consisting of adiposine forms 1 and 2, is disclosed in U.S. Pat. No. 4,254, 256. Additionally, a process for the preparation and purification of adiposine is disclosed in Namiki et al., *J. Antiobiotics*, 35, 1234–1236 (1982).

The glucosidase inhibitor voglibose, 3,4-dideoxy-4-[[2-hydroxy-1-(hydroxymethyl)ethyl]amino]-2—C-(hydroxymethyl)-D-epi-inositol, and the various N-substituted pseudo-aminosugars related thereto, are disclosed in U.S. Pat. No. 4,701,559.

The glucosidase inhibitor miglitol, (2R,3R,4R,5S)-1-(2-hydroxyethyl)-2-(hydroxymethyl)-3,4,5-piperidinetriol, and the various 3,4,5-trihydroxypiperidines related thereto, are disclosed in U.S. Pat. No. 4,639,436.

The glucosidase inhibitor emiglitate, ethyl p-[2-[(2R,3R, 4R,5S)-3,4,5-trihydroxy-2-(hydroxymethyl)piperidino] ethoxy]-benzoate, the various derivatives related thereto and pharmaceutically acceptable acid addition salts thereof, are disclosed in U.S. Pat. No. 5,192,772.

The glucosidase inhibitor MDL-25637, 2,6-dideoxy-7-O-β-D-glucopyrano-syl-2,6-imino-D-glycero-L-gluco-heptitol, the various homodisaccharides related thereto and the pharmaceutically acceptable acid addition salts thereof, are disclosed in U.S. Pat. No. 4,634,765.

The glucosidase inhibitor camiglibose, methyl 6-deoxy-6-[(2R,3R,4R,5S)-3,4,5-trihydroxy-2-(hydroxymethyl) piperidino]-α-D-glucopyranoside sesquihydrate, the deoxy-nojirimycin derivatives related thereto, the various pharmaceutically acceptable salts thereof and synthetic methods for the preparation thereof, are disclosed in U.S. Pat. Nos. 5,157,116 and 5,504,078.

The amylase inhibitor tendamistat, the various cyclic peptides related thereto and processes for the preparation thereof by the microbial cultivation of *Streptomyces tendae* strains 4158 or HAG 1226, are disclosed in U.S. Pat. No. 4,451,455.

The amylase inhibitor AI-3688, the various cyclic polypeptides related thereto, and a process for the preparation thereof by the microbial cultivation of *Streptomyces aureofaciens* strain FH 1656, are disclosed in U.S. Pat. No. 4,623,714.

The amylase inhibitor trestatin, consisting of a mixture of trestatin A, trestatin B and trestatin C, the various trehalose-containing aminosugars related thereto and a process for the preparation thereof by the microbial cultivation of *Streptomyces dimorphogenes* strains NR-320-OM7HB and NR-320-OM7HBS, are disclosed in U.S. Pat. No. 4,273, 765.

The glucosidase inhibitor pradimicin-Q and a process for the preparation thereof by the microbial cultivation of *Actinomadura verrucospora* strains R 103–3 or A10102, are disclosed in U.S. Pat. Nos. 5,091,418 and 5,217,877 respectively.

The glycosidase inhibitor salbostatin, the various pseudosaccharides related thereto, the various pharmaceutically acceptable salts thereof and a process for the preparation thereof by the microbial cultivation of *Streptomyces albus* strain ATCC 21838, are disclosed in U.S. Pat. No. 5,091, 524.

Preferred lipase inhibitors comprise compounds selected from the group consisting of lipstatin, tetrahydrolipstatin, FL-386, WAY-121898, Bay-n-3176, valilactone, esteracin, ebelactone A, ebelactone B, RHC 80267, stereoisomers thereof, and pharmaceutically acceptable salts of said compounds and stereoisomers. The compound tetrahydrolipstatin is especially preferred.

Preferred glucosidase inhibitors comprise compounds selected from the group consisting of acarbose, adiposine, voglibose, miglitol, emiglitate, MDL-25637, camiglibose, pradimicin-Q, and salbostatin. An especially preferred glucosidase inhibitor is acarbose. Especially preferred glucosidase inhibitors further comprise amylase inhibitors that are selected from the group consisting of tendamistate, AI-3688 and trestatin.

In addition, it is contemplated that the estrogen agonist/antagonist can be used in combination with MTP inhibitors and/or apo B secretion inhibitors.

A variety of apo B secretion/MTP inhibitors are known to one of ordinary skill in the art. Although any apo B secretion/MTP inhibitor may be used in the practice of the methods and pharmaceutical compositions of the instant invention, generally preferred apo B secretion/MTP inhibitors include those compounds that are disclosed in, for example, European Patent Application Publication Numbers EP 643057, EP 719763, EP 753517, EP 764647, EP 765878, EP 779276, EP 779279, EP 799828, EP 799829, EP 802186, EP 802188, EP 802192, and EP 802197; PCT Application Publication Numbers WO 96/13499, WO 96/33193, WO 96/40640, WO 97/26240, WO 97/43255, WO 97/43257, WO 98/16526 and WO 98/23593; and U.S. Pat. Nos. 5,595, 872; 5,646,162; 5,684,014; 5,712,279; 5,739,135 and 5,789, 197.

Especially preferred apo-B secretion/MTP inhibitors are those biphenyl-2-carboxylic acid-tetrahydroisoquinolin-6-yl amide derivatives disclosed in PCT Application Publication Numbers WO 96/40640 and WO 98/23593. Especially preferred apo B secretion/MTP inhibitors disclosed in PCT Application Publication Numbers WO 96/40640 and WO 98/23593, and useful in the methods and pharmaceutical compositions of the present invention, are 4'-trifluoromethyl-biphenyl-2-carboxylic acid-[2-(1H-[1,2, 4]triazol-3-ylmethyl)-1,2,3,4-tetrahydroisoquin-6-yl]-amide and 4'-trifluoromethyl-biphenyl-2-carboxylic acid-[2-(acetylaminoethyl)-1,2,3,4-tetrahydroisoquinolin-6-yl]-amide.

Another especially preferred class of apo B secretion/MTP inhibitors is disclosed in U.S. Pat. Nos. 5,595,872; 5,721,279; 5,739,135 and 5,789,197.

Especially preferred apo B secretion/MTP inhibitors disclosed in U.S. Pat. Nos. 5,595,872; 5,721,279; 5,739,135 and 5,789,197 and useful in the methods and pharmaceutical compositions of the present invention, are 9-(4-{4-[4'trifluoromethyl-biphenyl-2-carbonyl)-amino]-piperidin-1-yl}-butyl-9H-fluorene-9-carboxylic acid-(2,2,2-trifluoroethyl)-amide and 9-{4-[4-(2-benzothiazol-2-yl-benzoylamino)-piperidin-1-yl]-butyl}-9H-fluorene-9-carboxylic acid-(2,2,2-trifluoroethyl)-amide.

Another class of especially preferred apo B secretion/MTP inhibitors is disclosed in PCT Application Publication Number WO 98/16526.

Especially preferred apo B secretion/MTP inhibitors disclosed in PCT Application Publication Number WO 98/16526, and useful in the methods and pharmaceutical compositions of the present invention, are [11a-R]-8-[(4-cyanophenyl)methoxy]-2-cyclopentyl-7-(prop-2-enyl)-2,3,11,11a-tetrahydro-6H-pyrazino[1,2b]isoquinoline-1,4-dione and [11a-R]-cyclopentyl-7-(prop-2-enyl)-8-[(pyridin-2-yl)methoxy]-2,3,11,11a-tetrahydro-6H-pyrazino[1,2b]isoquinoline-1,4-dione.

Another especially preferred class of apo B secretion/MTP inhibitors is disclosed in U.S. Pat. No. 5,684,014.

An especially preferred apo B secretion/MTP inhibitor disclosed in U.S. Pat. No. 5,684,014, and useful in the methods and pharmaceutical compositions of the present invention, is 2-cyclopentyl-2-[4-(2,4-dimethyl-pyrido[2,3-b]indol-9-ylmethyl)-phenyl]-N-(2-hydroxy-1-phenyl-ethyl)-acetamide.

Yet another class of especially preferred apo B secretion/MTP inhibitors is disclosed in U.S. Pat. No. 5,646,162.

An especially preferred apo B secretion/MTP inhibitor disclosed in U.S. Pat. No. 5,646,162 and useful in the methods and pharmaceutical compositions of the present invention, is 2-cyclopentyl-N-(2-hydroxy-1-phenylethyl)-2-[4-(quinolin-2-ylmethoxy)-phenyl]-acetamide.

Compounds that are used to treat Raynaud's phenomenon include nifedipine and phenoxybenzamine. These compounds and others used to treat Raynaud's disease can be used in combination with estrogen agonists/antagonists.

The estrogen agonists/antagonists of the present invention can also be administered in combination with antihypertensives. Examples of classes of compounds that can be used to treat hypertension include calcium blockers, ACE inhibitors, diuretics, angiotensin II receptor blockers, β-blockers, and α-adrenergic blockers. In addition, combinations of compounds in the above-recited classes have been used to treat hypertension. Some examples of specific compounds that can be used in combination with an estrogen agonsit/antagonist include quinapril; amlodipine, including the besylate salt; nifedipine; doxazosin, including the mesylate salt; and prazosin, including the hydrochloride salt.

In the combination aspect of the methods and kits of the present invention, the estrogen agonist/antagonist and any additional compounds can be administered in the same dosage form or in separate dosage forms. The dosage forms can be the same (e.g., both tablets) or different. Likewise, the compounds can be administered at the same time or at different times. All variations are intended to be included in the present methods and kits.

The examples presented below are intended to exemplify particular embodiments of the invention and are not intended to limit the specification, including the claims, in any manner.

All documents cited herein, including patents and patent applications, are hereby incorporated by reference.

EXAMPLE
Brachial Artery Reactivity—Clinical Trial

Brachial Artery Imaging and Analysis
Introduction

One of the primary outcomes for this study will be the change in endothelial-dependent vasodilator capacity in the brachial artery following 8 weeks of treatment with (–)-cis-6-phenyl-5-[4-(2-pyrrolidin-1-yl-ethoxy)-phenyl]-5,6,7,8-tetrahydro-naphthalene-2-ol, conjugated equine estrogen or placebo. The vasodilator stimulus used will be an increase in brachial artery flow caused by ischemic hyperemia in the distal limb. The changes in diameter of the brachial artery will be imaged using high resolution 2-D ultrasound with the measurement of change in diameter being based on image processing techniques specifically designed to measure diameter of the brachial artery using automated boundary detection algorithms. Through the use of standardized protocols for subject preparation, image acquisition and image analysis, accurate and precise measurement of brachial artery diameter and wall thickness have been developed, validated and employed in numerous clinical studies.

Participants are allowed to rest in the supine position for 10 minutes in a quiet room. A blood pressure cuff is placed on the right forearm just below the antecubital fossa and the arm is supported with sand bags to allow inflation and deflation of the blood pressure cuff within movement of the arm. The blood pressure and heart rate are measured in the left arm using an automated sphygmomanometer. Once a comfortable and secure position has been established and the blood pressure is determined, images of the brachial artery at baseline are obtained (see section entitled "Image Acquisition"). After baseline imaging, the blood pressure cuff is rapidly inflated to 30 mm Hg greater than the systolic blood pressure for 5 minutes. The brachial artery is imaged again starting 30 seconds prior to cuff release and continuing for a total of 3 minutes following cuff release.

Image Acquisition

The right brachial artery is examined approximately 7 cm proximal to the bend of the elbow using a high resolution ultrasound system. A brief doppler signal is recorded in the vessel to confirm identification. Once the near and far wall boundaries are visualized with careful transducer movements, the transducer is maintained at this location throughout the examination. Careful observation of surrounding tissues provide internal landmarks to confirm that this is accomplished. Baseline images are then recorded for approximately 2 minutes on a video recorder. During the 5-minute interval during which the right blood pressure cuff is inflated to 30 mmHg above systolic pressure, the sonographer alternately views the B-mode image and the doppler signal to confirm that a high quality image is being maintained and that a significant modification of blood flow is being achieved in the vessel. During the final 30 seconds prior to rapid cuff deflation, high quality B-mode images are recorded. Immediately after cuff release, doppler signals are recorded for 10–15 seconds to observe the peak flow after cuff release, after which high quality B-mode images are continuously recorded for 3 minutes.

Image Analysis

The videotape is completely reviewed by the image analysis technicians prior to analysis. After identifying the portion of the tape demonstrating the brachial artery at baseline, 30 frames are digitized with a frame grabber into 512×512×8 bit grey scales and stored on the image analysis computer. Using a semi-automated boundary detection algorithm, the medial-advenitial boundary on the near and far wall of the brachial artery is located over an arterial segment 2.0–2.5 cm in length. If a boundary point is obviously displaced from the true location of the medial-adventitial boundary, then the image analysis technician will manually edit the boundary point in question. However, every effort is made to minimize the editing used. The average diameter of the artery is automatically calculated and the mean diameter from the 3-D baseline frames is used to determine the baseline diameter. The exact same procedure is repeated to determine the diameter of the artery just prior to cuff release. Similar methods are used to determine the maximum diameter that occurs during the 3 minutes immediately following cuff release. Time from cuff release to point of maximum dilation will also be recorded.

Primary and Secondary Outcome Measures

The primary outcome measure is relative change in mean arterial diameter calculated as follows:

$$\frac{\text{max diameter}}{\text{baseline diameter}} \times 100.$$

Time to maximum dilation and percent change from end of cuff occlusion to maximum dilation will also be determined.

What is claimed is:

1. A method of maintaining or improving vascular reactivity; or treating acute or chronic renal failure, peripheral arterial occlusive disease, coronary artery disease, or Raynaud's phenomenon, the method comprising administering to a patient in need of maintenance or improvement of vascular reactivity; or having acute or chronic renal failure, peripheral arterial occlusive disease, coronary artery disease, or Raynaud's phenomenon, a therapeutically effective amount of an estrogen agonist/antagonist.

2. The method of claim 1 wherein the estrogen agonist/antagonist is a compound of formula (I):

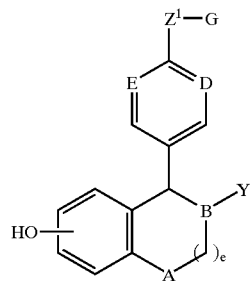

wherein:

A is selected from $CH_2$ and NR;

B, D and E are independently selected from CH and N;

Y is
  (a) phenyl, optionally substituted with 1–3 substituents independently selected from $R^4$;
  (b) naphthyl, optionally substituted with 1–3 substituents independently selected from $R^4$;
  (c) $C_3$–$C_8$ cycloalkyl, optionally substituted with 1–2 substituents independently selected from $R^4$;
  (d) $C_3$–$C_8$ cycloalkenyl, optionally substituted with 1–2 substituents independently selected from $R^4$;
  (e) a five membered heterocycle containing up to two heteroatoms selected from the group consisting of —O—, —$NR^2$— and —$S(O)_n$—, optionally substituted with 1–3 substituents independently selected from $R^4$;
  (f) a six membered heterocycle containing up to two heteroatoms selected from the group consisting of —O—, —$NR^2$— and —$S(O)_n$— optionally substituted with 1–3 substituents independently selected from $R^4$; or
  (g) a bicyclic ring system consisting of a five or six membered heterocyclic ring fused to a phenyl ring, said heterocyclic ring containing up to two heteroatoms selected from the group consisting of —O—, —$NR^2$— and —$S(O)_n$—, optionally substituted with 1–3 substituents independently selected from $R^4$;

$Z^1$ is
  (a) —$(CH_2)_p W(CH_2)_q$—;
  (b) —$O(CH_2)_p CR^5 R^6$—;
  (c) —$O(CH_2)_p W(CH_2)_q$—;
  (d) —$OCHR^2 CHR^3$—; or
  (e) —$SCHR^2 CHR^3$—;

G is
  (a) —$NR^7 R^8$;
  (b)

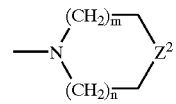

wherein n is 0, 1 or 2; m is 1, 2 or 3; $Z^2$ is —NH—, —O—, —S—, or —$CH_2$—; optionally fused on adjacent carbon atoms with one or two phenyl rings and, optionally independently substituted on carbon with one to three substituents and, optionally, independently on nitrogen with a chemically suitable substituent selected from $R^4$; or
  (c) a bicyclic amine containing five to twelve carbon atoms, either bridged or fused and optionally substituted with 1–3 substituents independently selected from $R^4$; or $Z^1$ and G in combination may be

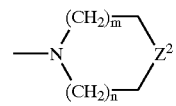

W is
  (a) —$CH_2$—;
  (b) —CH=CH—;
  (c) —O—;
  (d) —$NR^2$—;
  (e) —$S(O)_n$—;
  (f)

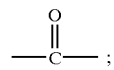

(g) —$CR^2(OH)$—;
  (h) —$CONR^2$;
  (i) —$NR^2CO$—;
  (j)

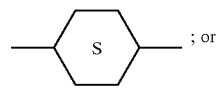

(k) —C≡C—;

R is hydrogen or $C_1$–$C_6$ alkyl;

$R^2$ and $R^3$ are independently
(a) hydrogen; or
(b) $C_1$–$C_4$ alkyl;

$R^4$ is
(a) hydrogen;
(b) halogen;
(c) $C_1$–$C_6$ alkyl;
(d) $C_1$–$C_4$ alkoxy;
(e) $C_1$–$C_4$ acyloxy;
(f) $C_1$–$C_4$ alkylthio;
(g) $C_1$–$C_4$ alkylsulfinyl;
(h) $C_1$–$C_4$ alkylsulfonyl;
(i) hydroxy ($C_1$–$C_4$)alkyl;
(j) aryl ($C_1$–$C_4$)alkyl;
(k) —$CO_2H$;
(l) —CN;
(m) —CONHOR;
(n) —$SO_2$NHR;
(o) —$NH_2$;
(p) $C_1$–$C_4$ alkylamino;
(q) $C_1$–$C_4$ dialkylamino;
(r) —$NHSO_2R$;
(s) —$NO_2$;
(t) -aryl; or
(u) —OH;

$R^5$ and $R^6$ are independently $C_1$–$C_8$ alkyl or together form a $C_3$–$C_{10}$ carbocyclic ring;

$R^7$ and $R^8$ are independently
(a) phenyl;
(b) a $C_3$–$C_{10}$ carbocyclic ring, saturated or unsaturated;
(c) a $C_3$–$C_{10}$ heterocyclic ring containing up to two heteroatoms, selected from —O—, —N— and —S—;
(d) H;
(e) $C_1$–$C_6$ alkyl; or
(f) form a 3 to 8 membered nitrogen containing ring with $R^5$ or $R^6$;

$R^7$ and $R^8$ in either linear or ring form may optionally be substituted with up to three substituents independently selected from $C_1$–$C_6$ alkyl, halogen, alkoxy, hydroxy and carboxy;

a ring formed by $R^7$ and $R^8$ may be optionally fused to a phenyl ring;

e is 0, 1 or 2;
m is 1, 2 or 3;
n is 0, 1 or 2;
p is 0, 1, 2 or 3;
q is 0, 1, 2 or 3;

or an optical or geometric isomer thereof; or a pharmaceutically acceptable salt, N-oxide, ester, quaternary ammonium salt or prodrug thereof.

3. The method of claim 1 wherein the estrogen agonist/antagonist is a compound of formula (IA)

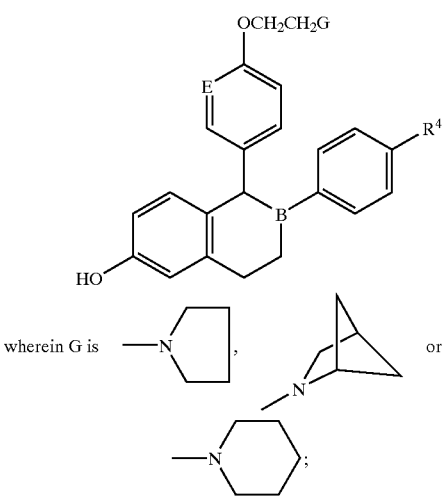

(IA)

wherein G is $R^4$ is H, OH, F, or Cl; and B and E are independently selected from CH and N or an optical or geometric isomer thereof; or a pharmaceutically acceptable salt, N-oxide, ester, quaternary ammonium salt, or a prodrug thereof.

4. The method of claim 3 wherein the estrogen agonist/antagonist is (–)-cis-6-phenyl-5-[4-(2-pyrrolidin-1-yl-ethoxy)-phenyl]-5,6,7,8-tetrahydro-naphthalene-2-ol or an optical or geometric isomer thereof; a pharmaceutically acceptable salt, N-oxide, ester, quaternary ammonium salt, or a prodrug thereof.

5. The method of claim 4 wherein the estrogen agonist/antagonist is in the form of a D-tartrate salt.

6. The method of claim 1 wherein said estrogen agonist/antagonist is a compound selected from the formulas V or VI:

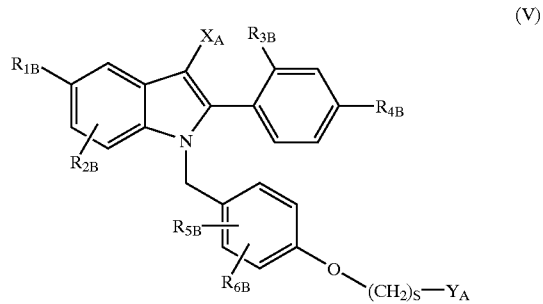

(V)

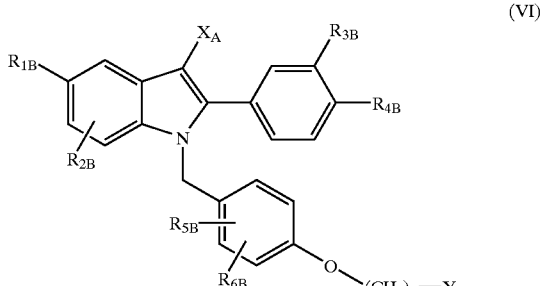

(VI)

wherein:
$R_{1B}$ is selected from H, OH, —O—C(O)—$C_1$–$C_{12}$ alkyl (straight chain or branched), —O—$C_1$–$C_{12}$ alkyl (straight chain or branched or cyclic), or halogens or $C_1$–$C_4$ halogenated ethers;

$R_{2B}$, $R_{3B}$, $R_{4B}$, $R_{5B}$, and $R_{6B}$ are independently selected from H, OH, —O—C(O)—$C_1$-$C_{12}$ (straight chain or branched), —O—$C_1$-$C_{12}$ (straight chain or branched or cyclic), halogens, or $C_1$-$C_4$ halogenated ethers, cyano, $C_1$-$C_6$ alkyl (straight chain or branched), or trifluoromethyl;

$X_A$ is selected from H, $C_1$-$C_8$ alkyl, cyano, nitro, trifluoromethyl, and halogen;

s is 2 or 3;

$Y_A$ is the moiety:

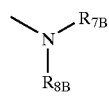

wherein:

a) $R_{7B}$ and $R_{8B}$ are independently selected from the group of H, $C_1$-$C_6$ alkyl, or phenyl optionally substituted by CN, $C_1$-$C_6$ alkyl (straight chain or branched), $C_1$-$C_6$ alkoxy (straight chain or branched), halogen, —OH, —$CF_3$, or —$OCF_3$; or b) $R_{7B}$ and $R_{8B}$ are concatenated to form a five-membered saturated heterocycle containing one nitrogen heteroatom, the heterocycle being optionally substituted with 1–3 substituents independently selected from the group consisting of hydrogen, hydroxyl, halo, $C_1$-$C_4$ alkyl, trihalomethyl, $C_1$-$C_4$ alkoxy, trihalomethoxy, $C_1$-$C_4$ acyloxy, $C_1$-$C_4$ alkylthio, $C_1$-$C_4$ alkylsulfinyl, $C_1$-C4 alkylsulfonyl, hydroxy ($C_1$-$C_4$)alkyl, —$CO_2H$, —CN, —$CONHR_{1B}$, —$NH_2$, —NH($C_1$-$C_4$ alkyl), —N($C_1$-$C_4$ alkyl)$_2$, —$NHSO_2R_{1B}$, —$NHCOR_{1B}$, —$NO_2$, or phenyl optionally substituted with 1–3 ($C_1$-$C_4$)alkyl; or c) $R_{7B}$ and $R_{8B}$ are concatenated to form a six-membered saturated heterocycle containing one nitrogen heteroatom, the heterocycle being optionally substituted with 1–3 substituents independently selected from the group consisting of hydrogen, hydroxyl, halo, $C_1$-$C_4$ alkyl, trihalomethyl, $C_1$-$C_4$ alkoxy, trihalomethoxy, $C_1$-$C_4$ acyloxy, $C_1$-$C_4$ alkylthio, $C_1$-$C_4$alkylsulfinyl, $C_1$-$C_4$ alkylsulfonyl, hydroxy ($C_1$-$C_4$)alkyl, —$CO_2H$, —CN, —$CONHR_{1B}$, —$NH_2$, —NH($C_1$-$C_4$ alkyl), —N($C_1$-$C_4$ alkyl)$_2$, —$NHSO_2R_{1B}$, —$NHCOR_{1B}$, —$NO_2$, or phenyl optionally substituted with 1–3 ($C_1$-$C_4$)alkyl; or d) $R_{7B}$ and $R_{8B}$ are concatenated to form a seven-membered saturated heterocycle containing one nitrogen heteroatom, the heterocycle being optionally substituted with 1–3 substituents independently selected from the group consisting of hydrogen, hydroxyl, halo, $C_1$-$C_4$ alkyl, trihalomethyl, $C_1$-$C_4$ alkoxy, trihalomethoxy, $C_1$-$C_4$ acyloxy, $C_1$-$C_4$ alkylthio, $C_1$-$C_4$ alkylsulfinyl, $C_1$-$C_4$ alkylsulfonyl, hydroxy ($C_1$—$C_4$)alkyl, —$CO_2H$, —CN, —$CONHR_{1B}$, —$NH_2$, —NH($C_1$-$C_4$ alkyl), —N($C_1$-$C_4$ alkyl)$_2$, —$NHSO_2R_{1B}$, —$NHCOR_{1B}$, —$NO_2$, or phenyl optionally substituted with 1–3 ($C_1$-$C_4$)alkyl; or e) $R_{7B}$ and $R_{8B}$ are concatenated to form an eight-membered saturated heterocycle containing one nitrogen heteroatom, the heterocycle being optionally substituted with 1–3 substituents independently selected from the group consisting of hydrogen, hydroxyl, halo, $C_1$-$C_4$ alkyl, trihalomethyl, $C_1$-$C_4$ alkoxy, trihalomethoxy, $C_1$-$C_4$ acyloxy, $C_1$-$C_4$ alkylthio, $C_1$-$C_4$ alkylsulfinyl, $C_1$-$C_4$ alkylsulfonyl, hydroxy ($C_1$-$C_4$)alkyl, —$CO_2H$, —CN, —$CONHR_{1B}$, —$NH_2$, —NH($C_1$-$C_4$ alkyl), —N($C_1$-$C_4$alkyl)$_2$, —$NHSO_2R_{1B}$, —$NHCOR_{1B}$, —$NO_2$, or phenyl optionally substituted with 1–3 ($C_1$-$C_4$)alkyl; or f) $R_{7B}$ and $R_{8B}$ are concatenated to form a saturated bicyclic heterocycle containing from 6–12 carbon atoms either bridged or fused and containing one nitrogen heteroatom, the heterocycle being optionally substituted with 1–3 substituents independently selected from the group consisting of hydrogen, hydroxyl, halo, $C_1$-$C_4$ alkyl, trihalomethyl, $C_1$-$C_4$ alkoxy, trihalomethoxy, $C_1$-$C_4$ acyloxy, $C_1$-$C_4$ alkylthio, $C_1$-$C_4$ alkylsulfinyl, $C_1$-$C_4$ alkylsulfonyl, hydroxy ($C_1$-$C_4$)alkyl, —$CO_2H$, —CN, —$CONHR_{1B}$, —$NH_2$, —NH($C_1$-$C_4$ alkyl), —N($C_1$-$C_4$ alkyl)$_2$, —$NHSO_2R_{1B}$, —$NHCOR_{1B}$, —$NO_2$, or phenyl optionally substituted with 1–3 ($C_1$-$C_4$) alkyl;

or an optical or geometric isomer thereof; or a pharmaceutically acceptable salt, N-oxide, ester, quaternary ammonium salt or prodrug thereof.

7. The method of claim 1 wherein the estrogen agonist/antagonist is the compound TSE-424 of formula Va below:

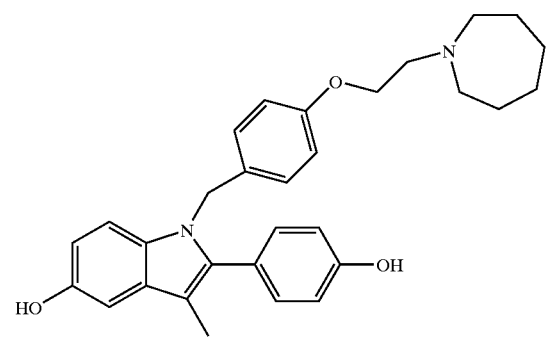

(Va)

or an optical or geometric isomer thereof; or a pharmaceutically acceptable salt, N-oxide, ester, quaternary ammonium salt or prodrug thereof.

8. The method of claim 1 wherein the estrogen agonist/antagonist is EM-652 of formula III below or is EM-800 of formula IV below:

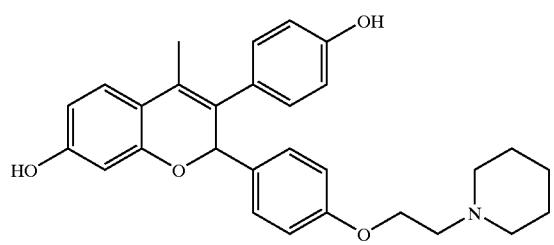

(III)

-continued (IV)

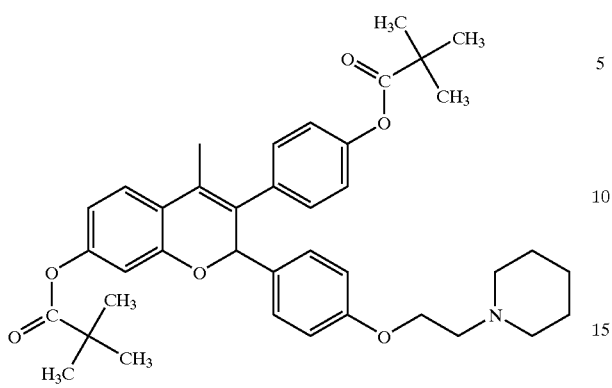

or an optical or geometric isomer thereof; or a pharmaceutically acceptable salt, N-oxide, ester, quaternary ammonium salt or prodrug thereof.

9. The method of claim 1 wherein a second compound that is useful to prevent myocardial infarction or stroke; maintain or improving vascular reactivity; or treat acute or chronic renal failure, peripheral arterial occlusive disease, coronary artery disease, or Raynaud's phenomenon, is administered to the patient.

10. A method of lowering the plasma concentration of Lp(a), the method comprising administering to a patient in need of plasma Lp(a) lowering a therapeutically effective amount of an estrogen agonist/antagonist.

11. The method of claim 10 wherein the estrogen agonist/antagonist is a compound of formula (I):

(I)

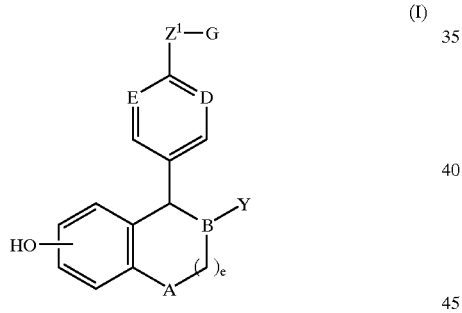

wherein:
A is selected from $CH_2$ and NR;
B, D and E are independently selected from CH and N;
Y is
  (a) phenyl, optionally substituted with 1–3 substituents independently selected from $R^4$;
  (b) naphthyl, optionally substituted with 1–3 substituents independently selected from $R^4$;
  (c) $C_3$–$C_8$ cycloalkyl, optionally substituted with 1–2 substituents independently selected from $R^4$;
  (d) $C_3$–$C_8$ cycloalkenyl, optionally substituted with 1–2 substituents independently selected from $R^4$;
  (e) a five membered heterocycle containing up to two heteroatoms selected from the group consisting of —O—, —$NR^2$— and —$S(O)_n$—, optionally substituted with 1–3 substituents independently selected from $R^4$;
  (f) a six membered heterocycle containing up to two heteroatoms selected from the group consisting of —O—, —$NR^2$— and —$S(O)_n$— optionally substituted with 1–3 substituents independently selected from $R^4$; or
  (g) a bicyclic ring system consisting of a five or six membered heterocyclic ring fused to a phenyl ring, said heterocyclic ring containing up to two heteroatoms selected from the group consisting of —O—, —$NR^2$— and —$S(O)_n$—, optionally substituted with 1–3 substituents independently selected from $R^4$;

$Z^1$ is
  (a) —$(CH_2)_pW(CH_2)_q$—;
  (b) —$O(CH_2)_pCR^5R^6$—;
  (c) —$O(CH_2)_pW(CH_2)_q$—;
  (d) —$OCHR^2CHR^3$—; or
  (e) —$SCHR^2CHR^3$—;

G is
  (a) —$NR^7R^8$;
  (b)

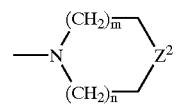

wherein n is 0, 1 or 2; m is 1, 2 or 3; $Z^2$ is —NH—, —O—, —S—, or —$CH_2$—; optionally fused on adjacent carbon atoms with one or two phenyl rings and, optionally independently substituted on carbon with one to three substituents and, optionally, independently on nitrogen with a chemically suitable substituent selected from $R^4$; or
  (c) a bicyclic amine containing five to twelve carbon atoms, either bridged or fused and optionally substituted with 1–3 substituents independently selected from $R^4$; or $Z^1$ and G in combination may be

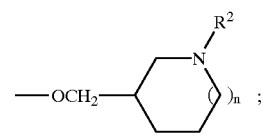

W is
  (a) —$CH_2$—;
  (b) —CH=CH—;
  (c) —O—;
  (d) —$NR^2$—;
  (e) —$S(O)_n$—;
  (f)

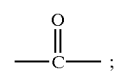

(g) —$CR^2(OH)$—;
  (h) —$CONR^2$—;
  (i) —$NR^2CO$—;
  (j)

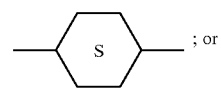

(k) —C≡C—;

R is hydrogen or $C_1$–$C_6$ alkyl;
$R^2$ and $R^3$ are independently
  (a) hydrogen; or (b) $C_1$–$C_4$ alkyl;

$R^4$ is
(a) hydrogen;
(b) halogen;
(c) $C_1$–$C_6$ alkyl;
(d) $C_1$–$C_4$ alkoxy;
(e) $C_1$–$C_4$ acyloxy;
(f) $C_1$–$C_4$ alkylthio;
(g) $C_1$–$C_4$ alkylsulfinyl;
(h) $C_1$–$C_4$ alkylsulfonyl;
(i) hydroxy ($C_1$–$C_4$)alkyl;
(j) aryl ($C_1$–$C_4$)alkyl;
(k) —$CO_2H$;
(l) —CN;
(m) —CONHOR;
(n) —$SO_2$NHR;
(o) —$NH_2$;
(p) $C_1$–$C_4$ alkylamino;
(q) $C_1$–$C_4$ dialkylamino;
(r) —$NHSO_2R$;
(p) $C_1$–$C_4$ alkylamino;
(q) $C_1$–$C_4$ dialkylamino;
(r) —$NHSO_2R$;
(s) —$NO_2$;
(t) -aryl; or
(u) —OH;

$R^5$ and $R^6$ are independently $C_1$–$C_8$ alkyl or together form a $C_3$–$C_{10}$ carbocyclic ring;

$R^7$ and $R^8$ are independently
(a) phenyl;
(b) a $C_3$–$C_{10}$ carbocyclic ring, saturated or unsaturated;
(c) a $C_3$–$C_{10}$ heterocyclic ring containing up to two heteroatoms, selected from —O—, —N— and —S—;
(d) H;
(e) $C_1$–$C_6$ alkyl; or
(f) form a 3 to 8 membered nitrogen containing ring with $R^5$ or $R^6$;

$R^7$ and $R^8$ in either linear or ring form may optionally be substituted with up to three substituents independently selected from $C_1$–$C_6$ alkyl, halogen, alkoxy, hydroxy and carboxy;

a ring formed by $R^7$ and $R^8$ may be optionally fused to a phenyl ring;

e is 0, 1 or 2;
m is 1, 2 or 3;
n is 0, 1 or 2;
p is 0, 1, 2 or 3;
q is 0, 1, 2 or 3;

or an optical or geometric isomer thereof; or a pharmaceutically acceptable salt, N-oxide, ester, quaternary ammonium salt or prodrug thereof.

12. The method of claim 10 wherein the estrogen agonist/antagonist is a compound of formula (IA):

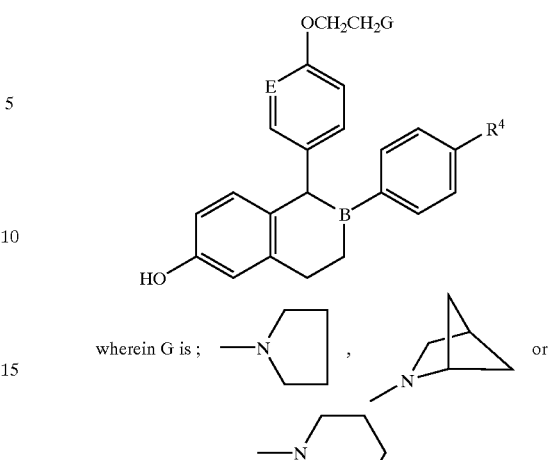

wherein G is:

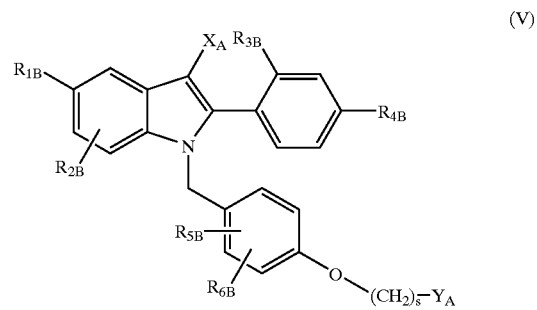

$R^4$ is H, OH, F, or Cl; and B and E are independently selected from CH and N or an optical or geometric isomer thereof; or a pharmaceutically acceptable salt, N-oxide, ester, quaternary ammonium salt, or a prodrug thereof.

13. The method of claim 12 wherein the estrogen agonist/antagonist is (−)-cis-6-phenyl-5-[4-(2-pyrrolidin-1-yl-ethoxy)-phenyl]-5,6,7,8-tetrahydro-naphthalene-2-ol or an optical or geometric isomer thereof; a pharmaceutically acceptable salt, N-oxide, ester, quaternary ammonium salt, or a prodrug thereof.

14. The method of claim 13 wherein the estrogen agonist/antagonist is in the form of a D-tartrate salt.

15. The method of claim 10 wherein said estrogen agonist/antagonist is a compound selected from the formulas V or VI:

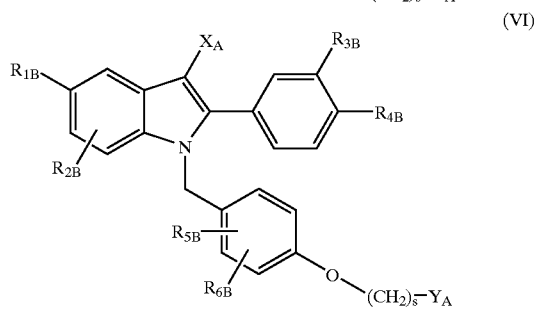

wherein:
$R_{1B}$ is selected from H, OH, —O—C(O)—$C_1$–$C_{12}$ alkyl (straight chain or branched), —O—$C_1$–$C_{12}$ alkyl (straight chain or branched or cyclic), or halogens or C—$C_4$ halogenated ethers;

$R_{2B}$, $R_{3B}$, $R_{4B}$, $R_{5B}$, and $R_{6B}$ are independently selected from H, OH, —O—C(O)—$C_1$-$C_{12}$ (straight chain or branched), —O—$C_1$-$C_{12}$ (straight chain or branched or cyclic), halogens, or $C_1$-$C_4$ halogenated ethers, cyano, $C_1$-$C_6$ alkyl (straight chain or branched), or trifluoromethyl;

$X_A$ is selected from H, $C_1$-$C_6$ alkyl, cyano, nitro, trifluoromethyl, and halogen;

s is 2 or 3;

$Y_A$ is the moiety:

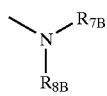

wherein:
a) $R_{7B}$ and $R_{8B}$ are independently selected from the group of H, $C_1$-$C_6$ alkyl, or phenyl optionally substituted by CN, $C_1$-$C_6$ alkyl (straight chain or branched), $C_1$-$C_6$ alkoxy (straight chain or branched), halogen, —OH, —$CF_3$, or —$OCF_3$; or b) $R_{7B}$ and $R_{8B}$ are concatenated to form a five-membered saturated heterocycle containing one nitrogen heteroatom, the heterocycle being optionally substituted with 1–3 substituents independently selected from the group consisting of hydrogen, hydroxyl, halo, $C_1$-$C_4$ alkyl, trihalomethyl, $C_1$-$C_4$ alkoxy, trihalomethoxy, $C_1$-$C_4$ acyloxy, $C_1$-$C_4$ alkylthio, $C_1$-$C_4$ alkylsulfinyl, $C_1$-$C_4$ alkylsulfonyl, hydroxy ($C_1$-$C_4$)alkyl, —$CO_2H$, —CN, —$CONHR_{1B}$, —$NH_2$, —NH($C_1$-$C_4$ alkyl), —N($C_1$-$C_4$ alkyl)$_2$, —$NHSO_2R_{1B}$, —$NHCOR_{1B}$, —$NO_2$, or phenyl optionally substituted with 1–3 ($C_1$-$C_4$)alkyl; or c) $R_{7B}$ and $R_{8B}$ are concatenated to form a six-membered saturated heterocycle containing one nitrogen heteroatom, the heterocycle being optionally substituted with 1–3 substituents independently selected from the group consisting of hydrogen, hydroxyl, halo, $C_1$-$C_4$ alkyl, trihalomethyl, $C_1$-$C_4$ alkoxy, trihalomethoxy, $C_1$-$C_4$ acyloxy, $C_1$-$C_4$ alkylthio, $C_1$-$C_4$ alkylsulfinyl, $C_1$-$C_4$ alkylsulfonyl, hydroxy ($C_1$-$C_4$)alkyl, —$CO_2H$, —CN, —$CONHR_{1B}$, —$NH_2$, —NH($C_1$-$C_4$ alkyl), —N($C_1$-$C_4$ alkyl)$_2$, —$NHSO_2R_{1B}$, —$NHCOR_{1B}$, —$NO_2$, or phenyl optionally substituted with 1–3 ($C_1$-$C_4$)alkyl; or d) $R_{7B}$ and $R_{8B}$ are concatenated to form a seven-membered saturated heterocycle containing one nitrogen heteroatom, the heterocycle being optionally substituted with 1–3 substituents independently selected from the group consisting of hydrogen, hydroxyl, halo, $C_1$-$C_4$ alkyl, trihalomethyl, $C_1$-$C_4$ alkoxy, trihalomethoxy, $C_1$-$C_4$ acyloxy, $C_1$-$C_4$ alkylthio, $C_1$-$C_4$ alkylsulfinyl, $C_1$-$C_4$ alkylsulfonyl, hydroxy ($C_1$-$C_4$)alkyl, —$CO_2H$, —CN, —$CONHR_{1B}$, —$NH_2$, —NH($C_1$-$C_4$ alkyl), —N($C_1$-$C_4$ alkyl)$_2$, —$NHSO_2R_{1B}$, —$NHCOR_{1B}$, —$NO_2$, or phenyl optionally substituted with 1–3 ($C_1$-$C_4$)alkyl; or e) $R_{7B}$ and $R_{8B}$ are concatenated to form an eight-membered saturated heterocycle containing one nitrogen heteroatom, the heterocycle being optionally substituted with 1–3 substituents independently selected from the group consisting of hydrogen, hydroxyl, halo, $C_1$-$C_4$ alkyl, trihalomethyl, $C_1$-$C_4$ alkoxy, trihalomethoxy, $C_1$-$C_4$ acyloxy, $C_1$-$C_4$ alkylthio, $C_1$-$C_4$ alkylsulfinyl, Cl—$C_4$ alkylsulfonyl, hydroxy ($C_1$-$C_4$)alkyl, —$CO_2H$, —CN, —$CONHR_{1B}$, —$NH_2$, —NH($C_1$-$C_4$ alkyl), —N($C_1$-$C_4$ alkyl)$_2$, —$NHSO_2R_{1B}$, —$NHCOR_{1B}$, —$NO_2$, or phenyl optionally substituted with 1–3 ($C_1$-$C_4$)alkyl; or f) $R_{7B}$ and $R_{8B}$ are concatenated to form a saturated bicyclic heterocycle containing from 6–12 carbon atoms either bridged or fused and containing one nitrogen heteroatom, the heterocycle being optionally substituted with 1–3 substituents independently selected from the group consisting of hydrogen, hydroxyl, halo, $C_1$-$C_4$ alkyl, trihalomethyl, $C_1$-$C_4$ alkoxy, trihalomethoxy, $C_1$-$C_4$ acyloxy, Cl—$C_4$ alkylthio, $C_1$-$C_4$ alkylsulfinyl, $C_1$-$C_4$ alkylsulfonyl, hydroxy ($C_1$-$C_4$)alkyl, —$CO_2H$, —CN, —$CONHR_{1B}$, —$NH_2$, —NH($C_1$-$C_4$ alkyl), —N($C_1$-$C_4$ alkyl)$_2$, —$NHSO_2R_1B$, —$NHCOR_{1B}$, —$NO_2$, or phenyl optionally substituted with 1–3 ($C_1$-$C_4$) alkyl;

or an optical or geometric isomer thereof; or a pharmaceutically acceptable salt, N-oxide, ester, quaternary ammonium salt or prodrug thereof.

16. The method of claim 10 wherein the estrogen agonist/antagonist is the compound TSE-424 of formula Va below:

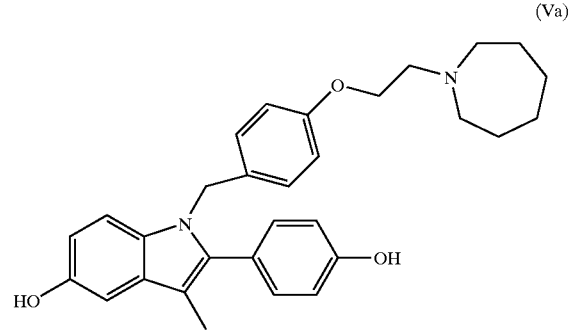

(Va)

or an optical or geometric isomer thereof; or a pharmaceutically acceptable salt, N-oxide, ester, quaternary ammonium salt or prodrug thereof.

17. The method of claim 10 wherein the estrogen agonist/antagonist is EM-652 of formula III below or is EM-800 of formula IV below:

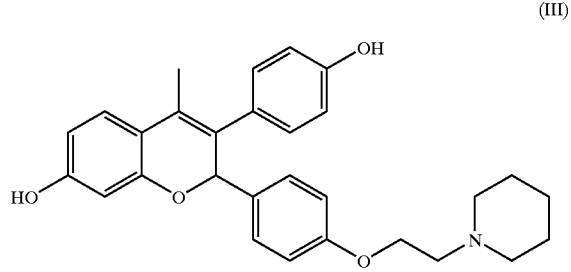

(III)

-continued (IV)

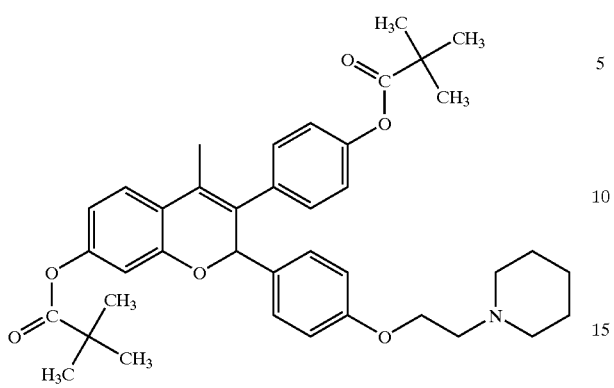

or an optical or geometric isomer thereof; or a pharmaceutically acceptable salt, N-oxide, ester, quaternary ammonium salt or prodrug thereof.

18. The method of claim 10 wherein a second compound that is useful to prevent myocardial infarction or stroke; maintain or improving vascular reactivity; treat acute or chronic renal failure, peripheral arterial occlusive disease, coronary artery disease, or Raynaud's phenomenon; or lower plasma levels of Lp(a) is administered to the patient.

19. A kit for use by a consumer to maintain or improve vascular reactivity; treat acute or chronic renal failure, peripheral arterial occlusive disease, coronary artery disease, or Raynaud's phenomenon; or lower plasma levels of Lp(a), the kit comprising:
   (a) a pharmaceutical composition comprising an estrogen agonist/antagonist and a pharmaceutically acceptable carrier, vehicle or diluent; and
   (b) instructions describing a method of using the pharmaceutical composition to maintain or improve vascular reactivity; treat acute or chronic renal failure, peripheral arterial occlusive disease, coronary artery disease or Raynaud's phenomenon; or lower plasma levels of Lp(a).

20. The kit of claim 19 wherein the estrogen agonist/antagonist is a compound of formula (I):

(I)

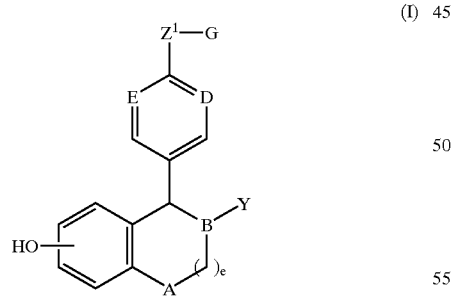

wherein:
A is selected from $CH_2$ and NR;
B, D and E are independently selected from CH and N;
Y is
   (a) phenyl, optionally substituted with 1–3 substituents independently selected from $R^4$;
   (b) naphthyl, optionally substituted with 1–3 substituents independently selected from $R^4$;
   (c) $C_3$–$C_8$ cycloalkyl, optionally substituted with 1–2 substituents independently selected from $R^4$;
   (d) $C_3$–$C_8$ cycloalkenyl, optionally substituted with 1–2 substituents independently selected from $R^4$;
   (e) a five membered heterocycle containing up to two heteroatoms selected from the group consisting of —O—, —$NR^2$— and —$S(O)_n$—, optionally substituted with 1–3 substituents independently selected from $R^4$;
   (f) a six membered heterocycle containing up to two heteroatoms selected from the group consisting of —O—, —$NR^2$— and —$S(O)_n$— optionally substituted with 1–3 substituents independently selected from $R^4$; or
   (g) a bicyclic ring system consisting of a five or six membered heterocyclic ring fused to a phenyl ring, said heterocyclic ring containing up to two heteroatoms selected from the group consisting of —O—, —$NR^2$— and —$S(O)_n$—, optionally substituted with 1–3 substituents independently selected from $R^4$;

$Z^1$ is
   (a) —$(CH_2)_p W(CH_2)_q$—;
   (b) —$O(CH_2)_p CR^5 R^6$—;
   (c) —$O(CH_2)_p W(CH_2)_q$—;
   (d) —$OCHR^2 CHR^3$—; or
   (e) —$SCHR^2 CHR^3$—;

G is
   (a) —$NR^7 R^8$;
   (b)

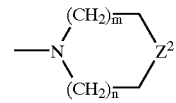

wherein n is 0, 1 or 2; m is 1, 2 or 3; $Z^2$ is —NH—, —O—, —S—, or —$CH_2$—; optionally fused on adjacent carbon atoms with one or two phenyl rings and, optionally independently substituted on carbon with one to three substituents and, optionally, independently on nitrogen with a chemically suitable substituent selected from $R^4$; or
   (c) a bicyclic amine containing five to twelve carbon atoms, either bridged or fused and optionally substituted with 1–3 substituents independently selected from $R^4$; or $Z^1$ and G in combination may be

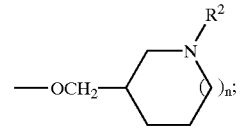

W is
   (a) —$CH_2$—;
   (b) —CH═CH—;
   (c) —O—;
   (d) —$NR^2$—;
   (e) —$S(O)_n$—;
   (f)

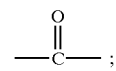

(g) —$CR^2(OH)$—;
   (h) —$CONR^2$—;

(i) —NR²CO—;
(j)

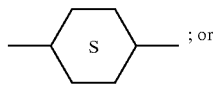

; or (k) —C≡C—;

R is hydrogen or $C_1$–$C_6$ alkyl;

R² and R³ are independently
  (a) hydrogen; or
  (b) $C_1$–$C_4$ alkyl;

R⁴ is
  (a) hydrogen;
  (b) halogen;
  (C) $C_1$–$C_6$ alkyl;
  (d) $C_1$–$C_4$ alkoxy;
  (e) $C_1$–$C_4$ acyloxy;
  (f) $C_1$–$C_4$ alkylthio;
  (g) $C_1$–$C_4$ alkylsulfinyl;
  (h) $C_1$–$C_4$ alkylsulfonyl;
  (i) hydroxy ($C_1$–$C_4$)alkyl;
  (j) aryl ($C_1$–$C_4$)alkyl;
  (k) —$CO_2$H;
  (l) —CN;
  (m) —CONHOR;
  (n) —$SO_2$NHR;
  (o) —$NH_2$;
  (p) $C_1$–$C_4$ alkylamino;
  (q) $C_1$–$C_4$ dialkylamino;
  (r) —$NHSO_2$R;
  (s) —$NO_2$;
  (t) -aryl; or
  (u) —OH;

R⁵ and R⁶ are independently $C_1$–$C_8$ alkyl or together form a $C_3$–$C_{10}$ carbocyclic ring;

R⁷ and R⁸ are independently
  (a) phenyl;
  (b) a $C_3$–$C_{10}$ carbocyclic ring, saturated or unsaturated;
  (c) a $C_3$–$C_{10}$ heterocyclic ring containing up to two heteroatoms, selected from —O—, —N— and —S—;
  (d) H;
  (e) $C_1$–$C_6$ alkyl; or
  (f) form a 3 to 8 membered nitrogen containing ring with R⁵ or R⁶;

R⁷ and R⁸ in either linear or ring form may optionally be substituted with up to three substituents independently selected from $C_1$–$C_6$ alkyl, halogen, alkoxy, hydroxy and carboxy;

a ring formed by R⁷ and R⁸ may be optionally fused to a phenyl ring;

e is 0, 1 or 2;
m is 1, 2 or 3;
n is 0, 1 or 2;
p is 0, 1, 2 or 3;
q is 0, 1, 2 or 3;

or an optical or geometric isomer thereof; or a pharmaceutically acceptable salt, N-oxide, ester, quaternary ammonium salt or prodrug thereof.

21. The kit of claim 19 wherein the estrogen agonist/antagonist is a compound of formula (IA):

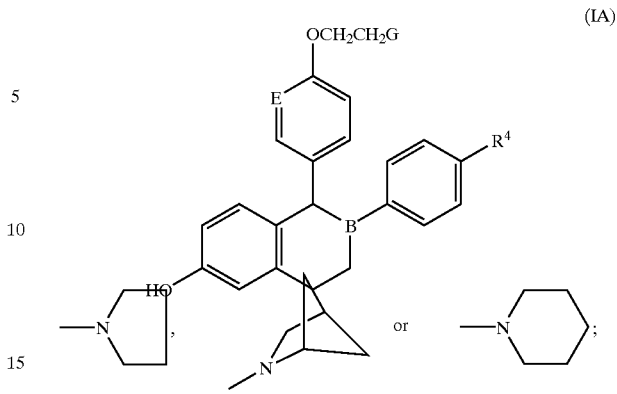

(IA)

R⁴ is H, OH, F, or Cl; and B and E are independently selected from CH and N or an optical or geometric isomer thereof; or a pharmaceutically acceptable salt, N-oxide, ester, quaternary ammonium salt, or a prodrug thereof.

22. The kit of claim 21 wherein the estrogen agonist/antagonist is (−)-cis-6-phenyl-5-[4-(2-pyrrolidin-1-yl-ethoxy)-phenyl]-5,6,7,8-tetrahydro-naphthalene-2-ol or an optical or geometric isomer thereof; or a pharmaceutically acceptable salt, N-oxide, ester, quaternary ammonium salt, or a prodrug thereof.

23. The kit of claim 22 wherein the estrogen agonist/antagonist is in the form of a D-tartrate salt.

24. The kit of claim 19 wherein the estrogen agonist/antagonist is a compound selected from the formulas V or VI:

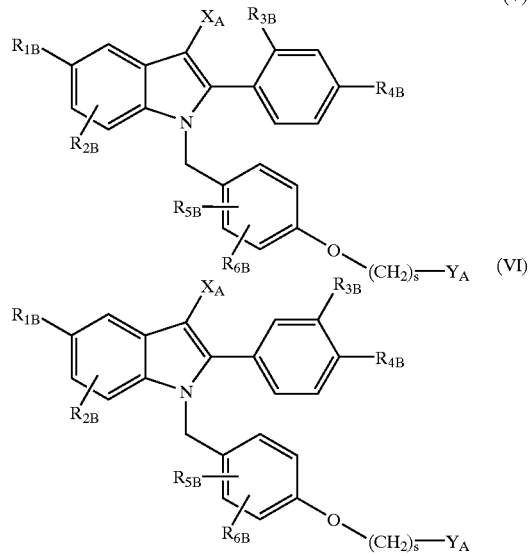

wherein:

$R_{1B}$ is selected from H, OH, —O—C(O)—$C_1$–$C_{12}$ alkyl (straight chain or branched), —O—$C_1$–$C_{12}$ alkyl (straight chain or branched or cyclic), or halogens or $C_1$–$C_4$ halogenated ethers;

$R_{2B}$, $R_{3B}$, $R_{4B}$, $R_{5B}$, and $R_{6B}$ are independently selected from H, OH, —O—C(O)—$C_1$–$C_{12}$ (straight chain or branched), —O—$C_1$–$C_{12}$ (straight chain or branched or cyclic), halogens, or $C_1$–$C_4$ halogenated ethers, cyano, $C_1$–$C_6$ alkyl (straight chain or branched), or trifluoromethyl;

$X_A$ is selected from H, $C_{-C6}$ alkyl, cyano, nitro, trifluoromethyl, and halogen;

s is 2 or 3;

$Y_A$ is the moiety:

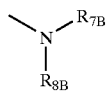

wherein:
a) $R_{7B}$ and $R_{8B}$ are independently selected from the group of H, $C_1$–$C_6$ alkyl, or phenyl optionally substituted by CN, $C_1$–$C_6$ alkyl (straight chain or branched), $C_1$–$C_6$ alkoxy (straight chain or branched), halogen, —OH, —$CF_3$, or —$OCF_3$; or
b) $R_{7B}$ and $R_{8B}$ are concatenated to form a five-membered saturated heterocycle containing one nitrogen heteroatom, the heterocycle being optionally substituted with 1–3 substituents independently selected from the group consisting of hydrogen, hydroxyl, halo, $C_1$–$C_4$ alkyl, trihalomethyl, $C$,—$C_4$ alkoxy, trihalomethoxy, $C_1$–$C_4$ acyloxy, $C_1$–$C_4$ alkylthio, $C_1$–$C_4$ alkylsulfinyl, Cl—$C_4$ alkylsulfonyl, hydroxy ($C_1$–$C_4$)alkyl, —$CO_2H$, —CN, —$CONHR_{1B}$, —$NH_2$, —NH($C_1$–$C_4$ alkyl), —N($C_1$–$C_4$ alkyl)$_2$, —$NHSO_2R_{1B}$, —$NHCOR_{1B}$, —$NO_2$, or phenyl optionally substituted with 1–3 ($C_1$–$C_4$)alkyl; or
c) $R_{7B}$ and $R_{8B}$ are concatenated to form a six-membered saturated heterocycle containing one nitrogen heteroatom, the heterocycle being optionally substituted with 1–3 substituents independently selected from the group consisting of hydrogen, hydroxyl, halo, $C_1$–$C_4$ alkyl, trihalomethyl, $C_1$–$C_4$ alkoxy, trihalomethoxy, $C_1$–$C_4$ acyloxy, $C_1$–$C_4$ alkylthio, $C_1$–$C_4$alkylsulfinyl, $C_1$–$C_4$ alkylsulfonyl, hydroxy ($C_1$–$C_4$)alkyl, —$CO_2H$, —CN, —$CONHR_{1B}$, —$NH_2$, —NH($C_1$–$C_4$ alkyl), —N($C_1$–$C_4$ alkyl)$_2$, —$NHSO_2R_{1B}$, —$NHCOR_{1B}$, —$NO_2$, or phenyl optionally substituted with 1–3 ($C_1$–$C_4$)alkyl; or
d) $R_{7B}$ and $R_{8B}$ are concatenated to form a seven-membered saturated heterocycle containing one nitrogen heteroatom, the heterocycle being optionally substituted with 1–3 substituents independently selected from the group consisting of hydrogen, hydroxyl, halo, $C_1$–$C_4$ alkyl, trihalomethyl, $C_1$–$C_4$ alkoxy, trihalomethoxy, $C_1$–$C_4$ acyloxy, $C_1$–$C_4$ alkylthio, $C_1$–$C_4$ alkylsulfinyl, $C_1$–$C_4$ alkylsulfonyl, hydroxy ($C_1$–$C_4$)alkyl, —$CO_2H$, —CN, —$CONHR_{1B}$, —$NH_2$, —NH($C_1$–$C_4$ alkyl), —N($C_1$–$C_4$ alkyl)$_2$, —$NHSO_2R_{1B}$, —$NHCOR_{1B}$, —$NO_2$, or phenyl optionally substituted with 1–3 ($C_1$–$C_4$)alkyl; or
e) $R_{7B}$ and $R_{8B}$ are concatenated to form an eight-membered saturated heterocycle containing one nitrogen heteroatom, the heterocycle being optionally substituted with 1–3 substituents independently selected from the group consisting of hydrogen, hydroxyl, halo, $C_1$–$C_4$ alkyl, trihalomethyl, $C_1$–$C_4$ alkoxy, trihalomethoxy, $C_1$–$C_4$ acyloxy, $C_1$–$C_4$ alkylthio, $C_1$–$C_4$ alkylsulfinyl, $C_1$–$C_4$ alkylsulfonyl, hydroxy ($C_1$–$C_4$)alkyl, —$CO_2H$, —CN, —$CONHR_{1B}$, —$NH_2$, —NH($C_1$–$C_4$ alkyl), —N($C_1$–$C_4$ alkyl)$_2$, —$NHSO_2R_{1B}$, —$NHCOR_{1B}$, —$NO_2$, or phenyl optionally substituted with 1–3 (Cl—$C_4$)alkyl; or
f) $R_{7B}$ and $R_{8B}$ are concatenated to form a saturated bicyclic heterocycle containing from 6–12 carbon atoms either bridged or fused and containing one nitrogen heteroatom, the heterocycle being optionally substituted with 1–3 substituents independently selected from the group consisting of hydrogen, hydroxyl, halo, $C_1$–$C_4$ alkyl, trihalomethyl, $C_1$–$C_4$ alkoxy, trihalomethoxy, $C_1$–$C_4$ acyloxy, $C_1$–$C_4$ alkylthio, $C_1$–$C_4$ alkylsulfinyl, $C_1$–$C_4$ alkylsulfonyl, hydroxy ($C_1$–$C_4$)alkyl, —$CO_2H$, —CN, —$CONHR_{1B}$, —$NH_2$, —NH($C_1$–$C_4$ alkyl), —N($C_1$–$C_4$ alkyl)$_2$, —$NHSO_2R_{1B}$, —$NHCOR_{1B}$, —$NO_2$, or phenyl optionally substituted with 1–3 ($C_1$–$C_4$) alkyl;

or an optical or geometric isomer thereof; or a pharmaceutically acceptable salt, N-oxide, ester, quaternary ammonium salt or prodrug thereof.

25. The kit of claim 19 wherein the estrogen agonist/antagonist is the compound TSE-424 of formula Va below:

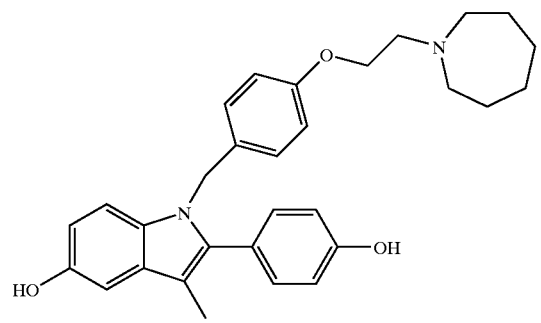

or an optical or geometric isomer thereof; or a pharmaceutically acceptable salt, N-oxide, ester, quaternary ammonium salt or prodrug thereof.

26. The kit of claim 19 wherein the estrogen agonist/antagonist is EM-652 of formula III below or EM-800 of formula IV below:

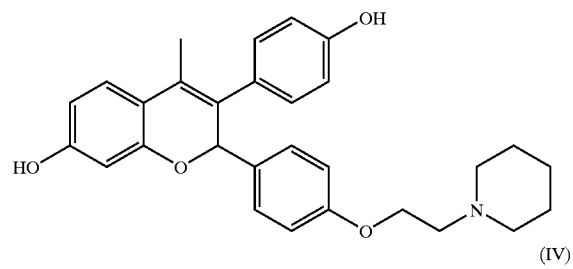

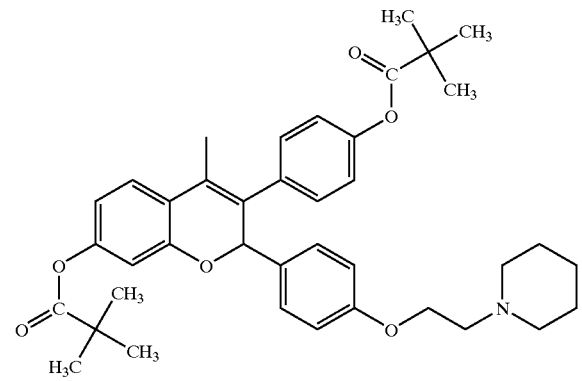

or an optical or geometric isomer thereof; or a pharmaceutically acceptable salt, N-oxide, ester, quaternary ammonium salt or prodrug thereof.

27. The kit of claim 19 wherein the kit further comprises an additional compound that is useful to prevent myocardial infarction or stroke; maintain or improve vascular reactivity; treat acute or chronic renal failure, peripheral arterial occlusive disease, coronary artery disease or Raynaud's phenomenon; or lower plasma levels of Lp(a).

* * * * *